US008202877B2

(12) United States Patent
Maechling et al.

(10) Patent No.: US 8,202,877 B2
(45) Date of Patent: Jun. 19, 2012

(54) AMINOPYRIMIDINAMIDES AS PESTICIDES

(75) Inventors: Simon Maechling, Köln (DE); Arnd Voerste, Köln (DE); Eva-Maria Franken, Lyons (FR); Angela Becker, Düsseldorf (DE); Ulrich Görgens, Ratingen (DE); Mazen Es-Sayed, Cuzon au Mont d'Or (FR); Markus Heil, Leichlingen (DE); Graham Holmwood, Leverkusen (DE); Johannes-Rudolf Jansen, Monheim (DE); Otto Schallner, Monheim (DE); Ulrich Ebbinghaus-Kintscher, Dortmund (DE); Peter Lümmen, Idstein (DE); Silvia Cerezo-Galvez, Langenfeld (DE); Sachio Kudo, Ibaraki (JP); Takashi Hashihayata, Ibaraki (JP); Eiichi Shimojo, Oyama (JP); Teruyuki Ichihara, Oyama (JP); Masashi Ataka, Tochigi (JP); Katsuhiko Shibuya, Tochigi (JP)

(73) Assignee: Bayer CropScience AG, Monheim (DE)

( * ) Notice: Subject to any disclaimer, the term of this patent is extended or adjusted under 35 U.S.C. 154(b) by 161 days.

(21) Appl. No.: 12/707,271

(22) Filed: Feb. 17, 2010

(65) Prior Publication Data
US 2010/0298267 A1 Nov. 25, 2010

(30) Foreign Application Priority Data

Feb. 17, 2009 (EP) ..................................... 09152972

(51) Int. Cl.
*C07D 239/48* (2006.01)
*C07D 401/12* (2006.01)
*A01N 43/50* (2006.01)
(52) U.S. Cl. .......................... 514/256; 544/326; 544/328
(58) Field of Classification Search .................. 544/326, 544/328; 514/256
See application file for complete search history.

(56) References Cited

U.S. PATENT DOCUMENTS
4,722,929 A    2/1988 Austel et al.
2004/0077641 A1 4/2004 Bretschneider et al.

FOREIGN PATENT DOCUMENTS
EP   0 149 200 A1    7/1985
EP   1 221 444 A1    7/2002
JP   01-316361 A    12/1989
WO   WO 98/23597 A1  6/1998
WO   WO 99/64428 A1 12/1999
WO   WO 02/067684 A1 9/2002
WO   WO 03/013484 A2 2/2003
WO   WO 2004/037823 A1 5/2004

OTHER PUBLICATIONS

Albert et al., CAPLUS Abstract 50:82103 (1956).*
Fu et al., CAPLUS Abstract 63:16870 (1965).*
Agranat et al., CAPLUS Abstract 90:204036 (1979).*
Barraclough et al., CAPLUS Abstract 125:328463 (1996).*
Fujii et al., CAPLUS Abstract 126:212045 (1997).*
Higashino et al., CAPLUS Abstract 109:170353 (1988).*
Baindur, N., et al., "Solution-Phase Synthesis of a Library of 3,5,7-Trisubstituted 3H-[1,2,3]triazolo[4,5-d]pyrimidines," *J. Comb. Chem.* 5:653-659, American Chemical Society, United States (2003).
Dang, Q., et al., "An unexpected cyclization discovered during the synthesis of 8-substituted purines from a 4,5-diaminopyrimidine," *Tetrahedron Letters* 49:2143-2145, Elsevier, Inc., England, United Kingdom (2008).
Elyutin, P., et al., "Partition Function of Nobel Gas Trimers," *Mendeleev Commun.* 3:161-163, Russian Academy of Sciences, Russian Federation (1993).
Hudson, C., et al., "Microwave-assisted three component one-pot synthesis of pyrimido-oxazepines," *Tetrahedron Letters* 48:1489-1492, Elsevier, Inc, England, United Kingdom (2007).
Liéby-Muller, F., et al., "Metal-free Michael addition initiated multicomponent oxidative cyclodehydration route to polyunsaturated pyridines from 1,3-dicarbonyls," *Chem. Commun.* 35:4207-4209, The Royal Society of Chemistry, England, United Kingdom (2008).
Patent Abstracts of Japan, English language abstract for JP 01-316361, Japanese Patent Office, Patent & Utility Model Gazette DB (1989).
International Search Report for International Application No. PCT/EP2010/000719, European Patent Office, mailed on Jun. 17, 2010.

* cited by examiner

*Primary Examiner* — Deepak Rao
(74) *Attorney, Agent, or Firm* — Sterne, Kessler, Goldstein & Fox P.L.L.C.

(57) ABSTRACT

The present application relates to novel aminopyrimidinamides, to processes for their preparation and to their use for controlling animal pests, especially arthropods, in particular insects.

9 Claims, No Drawings

AMINOPYRIMIDINAMIDES AS PESTICIDES

The present application relates to novel aminopyrimidinamides, to processes for their preparation and to their use as pesticides and in particular as insecticides and/or parasiticides.

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

WO 2002/067684 discloses certain pyridylpyrimidines as pesticides. However, they do not meet all demands in a satisfactory manner.

It was an object of the present invention to provide compounds which widen the spectrum of the pesticides under various aspects.

This object and further objects not explicitly mentioned which can be derived or deduced from the context discussed here are achieved by novel compounds of the formula (I)

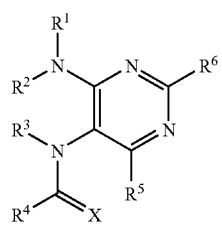

(I)

in which
$R^1$ represents a radical from the group consisting of hydrogen, alkyl, alkenyl, alkynyl, haloalkyl, cyanoalkyl, cycloalkyl, halocycloalkyl, cycloalkenyl, halocycloalkenyl, hydroxyalkyl, alkoxyalkyl, haloalkoxyalkyl, alkoxyhaloalkyl, alkylcarbonylalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, halocycloalkylalkyl, cycloalkylalkyl and in each case optionally substituted phenyl, naphthyl, phenylalkyl, heteroaryl, heteroarylalkyl, heterocyclyl and heterocyclylalkyl,
$R^2$ represents a radical from the group consisting of hydrogen, alkyl, alkenyl, alkynyl, haloalkyl, cyanoalkyl, cycloalkyl, halocycloalkyl, cycloalkenyl, halocycloalkenyl, hydroxyalkyl, alkoxyalkyl, haloalkoxyalkyl, alkoxyhaloalkyl, alkylcarbonylalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, cycloalkylalkyl and in each case optionally substituted phenyl, naphthyl, phenylalkyl, heteroaryl, heteroarylalkyl, heterocyclyl and heterocyclylalkyl,
$R^3$ represents a radical from the group consisting of hydrogen, alkyl, alkenyl, alkynyl, haloalkyl, cyanoalkyl, cycloalkyl, halocycloalkyl, cycloalkenyl, halocycloalkenyl, hydroxyalkyl, alkoxyalkyl, alkylthioalkyl, haloalkoxyalkyl, alkoxyhaloalkyl, alkylcarbonylalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, cycloalkylalkyl and in each case optionally substituted phenyl, naphthyl, phenylalkyl, heteroaryl, heteroarylalkyl, heterocyclyl and heterocyclylalkyl,
$R^4$ represents a radical from the group consisting of in each case optionally substituted phenyl, naphthyl, heteroaryl, heteroarylalkyl, heterocyclyl and heterocyclylalkyl,
$R^5$ represents a radical from the group consisting of hydrogen, halogen, cyano and in each case optionally substituted alkyl, cycloalkyl, phenyl, naphthyl, heteroaryl, heteroarylalkyl, heterocyclyl and heterocyclylalkyl,
$R^6$ represents a radical from the group consisting of hydrogen, halogen, alkyl, haloalkyl, cyanoalkyl, alkoxyalkyl, alkylcarbonyl, haloalkylcarbonyl, cycloalkyl, halocycloalkyl, cycloalkylalkyl, alkylsulphonyl, alkenyl, alkynyl, alkoxycarbonyl, alkenyloxycarbonyl, alkynyloxycarbonyl, alkoxycarbonylalkyl; optionally substituted phenyl, optionally substituted naphthyl, optionally substituted phenylalkyl, optionally substituted heterocyclylalkyl, optionally substituted heteroarylalkyl and optionally substituted phenylcarbonyl and
X represents oxygen or sulphur.

Furthermore, it has been found that compounds of the formula (I) can be prepared (Process 1) by reacting compounds of the formula (II)

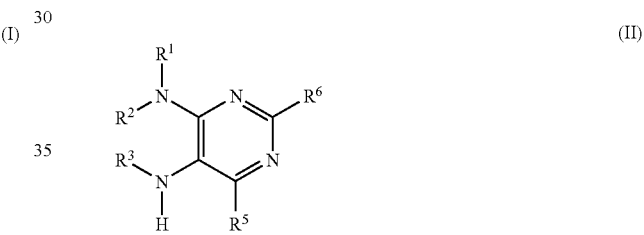

(II)

in which
$R^1$, $R^2$, $R^3$, $R^5$ and $R^6$ have the meanings given above,
with a compound of the formula (III)

$$R^4CXHal \qquad (III)$$

in which
X has the meaning given above and
Hal represents halogen, in particular chlorine,
in the presence of a diluent and in the presence of a base.

Compounds of the formula (I) can also be prepared (Process 2) by reacting compounds of the formula (IV)

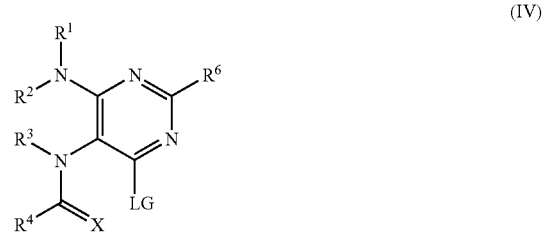

(IV)

in which
$R^1$, $R^2$, $R^3$, $R^4$ and $R^6$ have the meanings given above and
LG represents chlorine, bromine, iodine or alkylsulphonyl,
with boronic acids or boronic esters of the formula (V)

$$R^5-B(OR^a)_2$$

in which $R^5$ has the meanings given above and $R^a$ represents hydrogen or alkyl (in particular $C_1$-$C_4$-alkyl), in the presence of a diluent, a palladium catalyst and a base (Suzuki reaction).

Finally, it has been found that the novel compounds of the formula (I) have pronounced biological properties and are suitable especially for controlling animal pests, in particular insects, arachnids and nematodes, encountered in agriculture, in forests, in the protection of stored products and materials and in the hygiene sector.

If appropriate, the compounds of the formula (I) may, depending on the nature of the substituents, be present as geometrical and/or as optically active isomers or corresponding isomer mixtures or in various tautomeric forms of varying compositions. The invention relates both to the pure isomers and to the isomer mixtures.

If appropriate, the compounds of the formula (I) may be present in various polymorphic forms or as mixtures of different polymorphic forms. The invention provides both the pure polymorphs and the polymorph mixtures, and both can be used according to the invention.

The formula (I) provides a general definition of the compounds according to the invention.

Preferred substituents or ranges of the radicals listed under the formulae mentioned above and below are illustrated below.

$R^1$ preferably represents a radical from the group consisting of $C_1$-$C_6$-alkyl, $C_2$-$C_6$-alkenyl, $C_2$-$C_6$-alkynyl, $C_1$-$C_6$-haloalkyl, cyano-$C_1$-$C_6$-alkyl, $C_3$-$C_8$-cycloalkyl (in particular $C_3$-$C_6$-cycloalkyl), $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_1$-$C_6$-haloalkylsulphanyl-$C_1$-$C_6$-alkyl, $C_1$-$C_6$-haloalkylsulphinyl-$C_1$-$C_6$-alkyl, $C_1$-$C_6$-haloalkylsulphonyl-$C_1$-$C_6$-alkyl, $C_3$-$C_8$-cycloalkyl-$C_1$-$C_6$-alkyl, halogenated $C_3$-$C_8$-cycloalkyl-$C_1$-$C_6$-alkyl, phenyl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; heterocyclyl which is optionally mono- or polysubstituted by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano and heterocyclyl-$C_1$-$C_6$-alkyl which is optionally mono- or polysubstituted at the heterocycle by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano.

$R^2$ preferably represents a radical from the group consisting of hydrogen, $C_1$-$C_6$-alkyl, $C_2$-$C_6$-alkenyl, $C_2$-$C_6$-alkynyl, $C_1$-$C_6$-haloalkyl, cyano-$C_1$-$C_6$-alkyl, $C_3$-$C_8$-cycloalkyl (in particular $C_3$-$C_6$-cycloalkyl), $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_1$-$C_6$-haloalkylsulphanyl-$C_1$-$C_6$-alkyl, $C_1$-$C_6$-haloalkylsulphinyl-$C_1$-$C_6$-alkyl, $C_1$-$C_6$-haloalkylsulphonyl-$C_1$-$C_6$-alkyl, $C_3$-$C_8$-cycloalkyl-$C_1$-$C_6$-alkyl, phenyl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano; heterocyclyl which is optionally mono- or polysubstituted by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano and heterocyclyl-$C_1$-$C_6$-alkyl which is optionally mono- or polysubstituted at the heterocycle by identical or different substituents from the group consisting of —OH/═O, —SH/═S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro or cyano.

$R^3$ preferably represents a radical from the group consisting of hydrogen, $C_1$-$C_6$-alkyl, $C_2$-$C_6$-alkenyl, $C_2$-$C_6$-alkynyl, halo-$C_1$-$C_6$-alkyl, cyano-$C_1$-$C_6$-alkyl, $C_3$-$C_8$-cycloalkyl, halo-$C_3$-$C_8$-cycloalkyl, $C_3$-$C_8$-cycloalkenyl, halo-$C_3$-$C_8$-cycloalkenyl, $C_1$-$C_6$-alkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_3$-$C_8$-cycloalkyl-$C_1$-$C_6$-alkyl, phenyl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heterocyclyl which is optionally mono- or polysubstituted by identical or different substituents from the group consisting of —OH/═O, —SH/═S, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano and heterocyclyl-$C_1$-$C_6$-alkyl which is optionally mono- or polysubstituted at the heterocycle by identical or different substituents from the group consisting of —OH/═O, —SH/═S, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano.

$R^4$ preferably represents a radical from the group consisting of phenyl, 2-pyridyl, 3-pyridyl and pyrazolyl which are in each case optionally mono- or polysubstituted by identical or different radicals from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxy-$C_1$-$C_6$-alkoxy, COOH, nitro, amino, cyano, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, $C_1$-$C_6$-alkylaminocarbonyl, $C_3$-$C_6$-cycloalkylaminocarbonyl, phenyl (which for its part may be substituted by halogen), and hetaryl-$C_1$-$C_6$-alkyl (in particular pyrazolyl-$C_1$-$C_6$-alkyl (which for its part may be substituted by halogen, $C_1$-$C_6$-alkyl and $C_1$-$C_6$-haloalkyl)).

$R^5$ preferably represents a radical from the group consisting of hydrogen, halogen, cyano, $C_1$-$C_6$-alkyl, $C_1$-$C_6$-haloalkyl, $C_3$-$C_8$-cycloalkyl, $C_3$-$C_8$-halocycloalkyl and also phenyl, 2-pyridyl or 3-pyridyl which are in each case optionally mono- or polysubstituted by identical or different radicals from the group consisting of halogen, amino, cyano, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, $C_1$-$C_6$-alkoxy-$C_1$-$C_6$-alkoxy, nitro, cyano, $C_1$-$C_6$-alkylcarbonyl, $C_1$-$C_6$-alkylcarbonylamino, $C_3$-$C_6$-cycloalkylcarbonylamino, $C_1$-$C_6$-alkylaminocarbonyl, $C_3$-$C_6$-cycloalkylaminocarbonyl $C_1$-$C_6$-alkoxycarbonyl, aminocarbonyl, $C_1$-$C_6$-alkoxyimino-$C_1$-$C_6$-alkyl, $C_1$-$C_6$-alkylsulphanyl, $C_1$-$C_6$-alkylsulphinyl, $C_1$-$C_6$-alkylsulphonyl, $C_1$-$C_6$-alkylsulphonyloxy, $C_1$-$C_6$-alkylsulphonylamino, $C_1$-$C_6$-haloalkylsulphanyl, $C_1$-$C_6$-haloalkylsulphinyl, $C_1$-$C_6$-haloalkylsulphonyl, tri-$C_1$-$C_6$-alkylsilyl, S(O)(═N—CN), S(O)(═N)R (in which R represents $C_1$-$C_6$-alkyl or $C_1$-$C_6$-haloalkyl), phenyl, phenyl-$C_1$-$C_6$-alkyl, phenyl-$C_1$-$C_6$-alkyloxy, phenyloxy, pyrazolyl (where the phenyl groups or the pyrazolyl ring for their part may be substituted by halogen, $C_1$-$C_6$-alkyl, $C_3$-$C_8$-cycloalkyl, $C_1$-$C_6$-alkoxy, $C_1$-$C_6$-haloalkoxy, nitro, cyano, $C_1$-$C_6$-alkylsulphanyl, $C_1$-$C_6$-alkylsulphinyl, $C_1$-$C_6$-alkylsulphonyl, $C_1$-$C_6$-alkylsulphonyloxy, $C_1$-$C_6$-alkylsulphonylamino, $C_1$-$C_6$-haloalkylsulphanyl, $C_1$-$C_6$-haloalkylsulphinyl, $C_1$-$C_6$-haloalkylsulphonyl, S(O)(═N—CN), S(O)(═N)R (in which R represents $C_1$-$C_6$-alkyl or $C_1$-$C_6$-haloalkyl)), hetaryloxy-$C_1$-$C_6$-alkyl, hetaryloxy and hetaryl-$C_1$-$C_6$-alkyl, (where the hetaryl radical is in each case selected from the group consisting of pyrrolyl, imidazolyl, pyrazolyl, triazolyl, pyridyl, pyrimidinyl and tetrazolyl and may for its part be substituted by halogen, cyano, $C_1$-$C_6$-alkyl, $C_1$-$C_6$-haloalkyl, $C_3$-$C_8$-cycloalkyl, $C_3$-$C_8$-halocycloalkyl) and where two adjacent substituents together may also represent —OCH$_2$O—, —OCF$_2$O— or —OCH$_2$CH$_2$O— (cf. Ex. No. 1-12).

$R^6$ preferably represents a radical from the group consisting of hydrogen, halogen, $C_1$-$C_6$-alkyl, $C_1$-$C_6$-haloalkyl, cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-haloalkylcarbonyl, $C_3$-$C_8$-cycloalkyl, $C_3$-$C_8$-halocycloalkyl, $C_3$-$C_8$-cycloalkyl-$C_1$-$C_6$-alkyl, $C_1$-$C_6$-alkylsulphanyl, $C_1$-$C_6$-alkylsulphonyl, $C_2$-$C_6$-alkenyl, $C_2$-$C_6$-alkynyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkoxycarbonyl-$C_1$-$C_6$-alkyl; phenyl, phenyl-$C_1$-$C_6$-alkyl which are in each case optionally mono- or polysubstituted at the phenyl ring by identical or different radicals from the group consisting of halogen, $C_1$-$C_6$-alkyl, $C_1$-$C_6$-haloalkyl, $C_1$-$C_6$-alkoxy, nitro or cyano; heterocyclyl-$C_1$-$C_6$-alkyl which is optionally mono- or polysubstituted at the heterocycle by identical or different substituents from the group consisting of halogen, $C_1$-$C_6$-alkyl, $C_1$-$C_6$-haloalkyl, $C_1$-$C_6$-alkoxy, nitro or cyano; heteroaryl-$C_1$-$C_6$-alkyl which is optionally mono- or polysubstituted at the heteroaromatic moiety by identical or different radicals from the group consisting of halogen, $C_1$-$C_6$-alkyl, $C_1$-$C_6$-haloalkyl, $C_1$-$C_6$-alkoxy, nitro or cyano; or phenylcarbonyl which is optionally mono- or polysubstituted at the phenyl ring by identical or different radicals from the group consisting of halogen, $C_1$-$C_6$-alkyl, $C_1$-$C_6$-haloalkyl, $C_1$-$C_6$-alkoxy, nitro or cyano.

X preferably represents oxygen or sulphur.

$R^1$ particularly preferably represents a radical from the group consisting of $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl (in particular $C_3$-$C_6$-cycloalkyl), $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylsulphanyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_3$-$C_6$-cycloalkyl-$C_1$-$C_6$-alkyl, halogenated $C_3$-$C_6$-cycloalkyl-$C_1$-$C_6$-alkyl, phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heterocyclyl-$C_1$-$C_6$-alkyl which is optionally mono- or polysubstituted at the heterocycle by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano.

$R^2$ particularly preferably represents a radical from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl (in particular $C_3$-$C_6$-cycloalkyl), $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heterocyclyl-$C_1$-$C_6$-alkyl which is optionally mono- or polysubstituted at the heterocycle by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano.

$R^3$ particularly preferably represents a radical from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl (in particular $C_3$-$C_6$-cycloalkyl), $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, phenyl-$C_1$-$C_6$-alkyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, nitro or cyano; heteroaryl which is optionally mono- or polysubstituted by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heteroaryl-$C_1$-$C_6$-alkyl which is optionally mono- or polysubstituted at the heteroaromatic moiety by identical or different substituents from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano; heterocyclyl-$C_1$-$C_6$-alkyl which is optionally mono- or polysubstituted at the heterocycle by identical or different substituents from the group consisting of —OH/=O, —SH/=S, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro or cyano.

$R^4$ particularly preferably represents 3-pyridyl or pyrazolyl which are in each case optionally mono- or polysubstituted by identical or different radicals from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, COOH, nitro, amino, mono-$C_1$-$C_6$-alkylamino, di-$C_1$-$C_6$-alkylamino, $C_1$-$C_6$-alkylaminocarbonyl and $C_3$-$C_6$-cycloalkylaminocarbonyl.

$R^4$ furthermore also particularly preferably represents phenyl which is optionally substituted by halogen, cyano, $C_1$-$C_6$-alkyl and $C_1$-$C_6$-haloalkyl.

$R^4$ furthermore also particularly preferably represents pyrazolyl which is optionally substituted by halogen or $C_1$-$C_6$-alkyl, phenyl (which for its part may be substituted by halogen) or by pyrazolylmethyl (which for its part may be substituted by $C_1$-$C_6$-haloalkyl).

$R^5$ particularly preferably represents phenyl, 2-pyridyl or 3-pyridyl (in particular phenyl) which are in each case optionally mono- or polysubstituted by identical or different radicals from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxy-$C_1$-$C_6$-alkoxy, nitro, amino, cyano, mono-$C_1$-$C_6$-alkylamino, di-$C_1$-$C_6$-alkylamino, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, hetaryloxy-$C_1$-$C_6$-alkyl, hetaryloxy and hetaryl-$C_1$-$C_6$-alkyl, where the hetaryl radical is selected from the group consisting of pyrrolyl, imidazolyl, pyrazolyl, triazolyl, pyridyl, pyrimidinyl and tetrazolyl and for its part may be substituted by substituents from the group consisting of halogen, cyano, $C_1$-$C_6$-alkyl, $C_1$-$C_6$-haloalkyl, $C_3$-$C_8$-cycloalkyl and $C_3$-$C_8$-halocycloalkyl.

$R^5$ also particularly preferably represents hydrogen, halogen, $C_1$-$C_4$-alkyl and $C_3$-$C_6$-cycloalkyl.

R⁶ particularly preferably represents a radical from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_1$-$C_6$-alkylcarbonyl, $C_1$-$C_6$-haloalkylcarbonyl, $C_3$-$C_6$-cycloalkyl, $C_3$-$C_6$-cycloalkyl-$C_1$-$C_6$-alkyl, $C_1$-$C_6$-alkylsulphanyl, $C_2$-$C_6$-alkenyl, $C_2$-$C_6$-alkynyl, $C_1$-$C_6$-alkoxycarbonyl, $C_1$-$C_6$-alkenyloxycarbonyl, $C_2$-$C_6$-alkynyloxycarbonyl, $C_1$-$C_6$-alkoxycarbonyl-$C_1$-$C_6$-alkyl, phenyl, phenyl-$C_1$-$C_6$-alkyl which are in each case optionally mono- or polysubstituted at the phenyl ring by identical or different radicals from the group consisting of halogen, $C_1$-$C_6$-alkyl, $C_1$-$C_6$-haloalkyl, $C_1$-$C_6$-alkoxy, nitro or cyano; heterocyclyl-$C_1$-$C_6$-alkyl which may optionally be mono- or polysubstituted at the heterocycle by identical or different substituents from the group consisting of halogen, $C_1$-$C_6$-alkyl, $C_1$-$C_6$-haloalkyl, $C_1$-$C_6$-alkoxy, nitro or cyano; and phenylcarbonyl which is optionally mono- or polysubstituted at the phenyl ring by identical or different substituents from the group consisting of halogen, $C_1$-$C_6$-alkyl, $C_1$-$C_6$-haloalkyl, $C_1$-$C_6$-alkoxy, nitro or cyano.

X particularly preferably represents oxygen or sulphur, in particular oxygen.

R¹ very particularly preferably represents a radical from the group consisting of $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-alkylsulphanyl-$C_1$-$C_6$-alkyl, $C_1$-$C_6$-alkoxycarbonyl-$C_1$-$C_6$-alkyl and $C_3$-$C_6$-cycloalkyl-$C_1$-$C_6$-alkyl and halogenated $C_3$-$C_6$-cycloalkyl-$C_1$-$C_6$-alkyl, in particular cyclopropyl.

R² very particularly preferably represents hydrogen,

R³ very particularly preferably represents hydrogen.

R⁴ very particularly preferably represents 3-pyridyl which is mono- or polysubstituted by radicals from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy, $C_1$-$C_6$-alkylaminocarbonyl and $C_3$-$C_6$-cycloalkylaminocarbonyl.

R⁴ furthermore very particularly preferably represents phenyl which is optionally substituted by halogen, cyano, $C_1$-$C_6$-alkyl and $C_1$-$C_6$-haloalkyl.

R⁴ furthermore very particularly preferably represents pyrazolyl (preferably 3-pyrazolyl) which may be substituted by halogen (preferably F, Cl, Br) and $C_1$-$C_6$-alkyl (preferably methyl, ethyl and propyl), phenyl (which for its part may be substituted by halogen) or by pyrazolylmethyl (which for its part may be substituted by $C_1$-$C_6$-haloalkyl, in particular fluorinated $C_1$-$C_6$-alkyl).

R⁵ very particularly preferably represents a radical from the group consisting of phenyl, 2-pyridyl and 3-pyridyl (in particular phenyl), each of which is mono- or polysubstituted by at least one radical from the group consisting of halogen, $C_1$-$C_6$-alkyl, $C_1$-$C_6$-haloalkyl, $C_1$-$C_6$-alkoxy, $C_1$-$C_6$-haloalkoxy, nitro, cyano, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, hetaryloxy-$C_1$-$C_6$-alkyl, hetaryloxy and hetaryl-$C_1$-$C_6$-alkyl, where the hetaryl radical is selected from the group consisting of pyrrolyl, imidazolyl, pyrazolyl, triazolyl, pyridyl, pyrimidinyl and tetrazolyl and may for its turn be substituted by substituents from the group consisting of halogen, cyano, $C_1$-$C_6$-alkyl, $C_1$-$C_6$-haloalkyl, $C_3$-$C_8$-cycloalkyl and $C_3$-$C_8$-halocycloalkyl.

R⁵ also very particularly preferably represents a radical from the group consisting of hydrogen, halogen, $C_1$-$C_4$-alkyl and $C_3$-$C_6$-cycloalkyl.

R⁶ very particularly preferably represents a radical from the group consisting of hydrogen, halogen, $C_1$-$C_6$-alkyl, $C_1$-$C_6$-haloalkyl, $C_3$-$C_6$-cycloalkyl, $C_1$-$C_6$-alkylsulphonyl and phenyl which may be substituted by halogen.

X very particularly preferably represents oxygen.

R¹ most preferably represents a radical from the group consisting of $CH_3$, $CH_2CH_3$, $CH(CH_3)_2$, cyclopropyl, halocyclopropyl, $C(CH_3)_3$, $CH(CH_3)CH_2SCH_3$, $CH_2CH_2CH_3$, $CH(CH_3)CH_2CH_3$, $CH_2CF_3$, $CHCH_3CF_3$, $CH(CH_3)$cyclopropyl and with particular emphasis cyclopropyl.

R² most preferably represents hydrogen.

R³ most preferably represents hydrogen.

R⁴ most preferably represents 3-pyridyl which is substituted in the 2-position by a substituent from the group consisting of F, Cl, Br, methyl, ethyl, $CF_3$, $CH_2CF_3$, $CHFCH_3$, $CHFCF_3$, cyclopropyl and cyclopropylmethyl.

R⁴ furthermore most preferably represents phenyl which may be substituted by F, Cl, CN, $CH_3$, $C_2H_5$, $CF_3$ and $C_2F_5$.

R⁴ furthermore most preferably represents pyrazolyl (preferably 3-pyrazolyl) which may be substituted by F, Cl, methyl, ethyl or by pyrazolylmethyl which for its part may be substituted by $C_1$-$C_6$-haloalkyl, in particular by $CF_3$.

R⁵ most preferably represents phenyl which is mono- or polysubstituted by a radical from the group consisting of $CH_3$, F, Cl, $CF_3$, $CF(CF_3)_2$, $OCH_3$, $OCF_3$, $NO_2$, CN, $SCF_3$, $S(O)CF_3$ and $S(O)_2CF_3$ and $CH_2$-Q.

Q represents a radical from the group consisting of

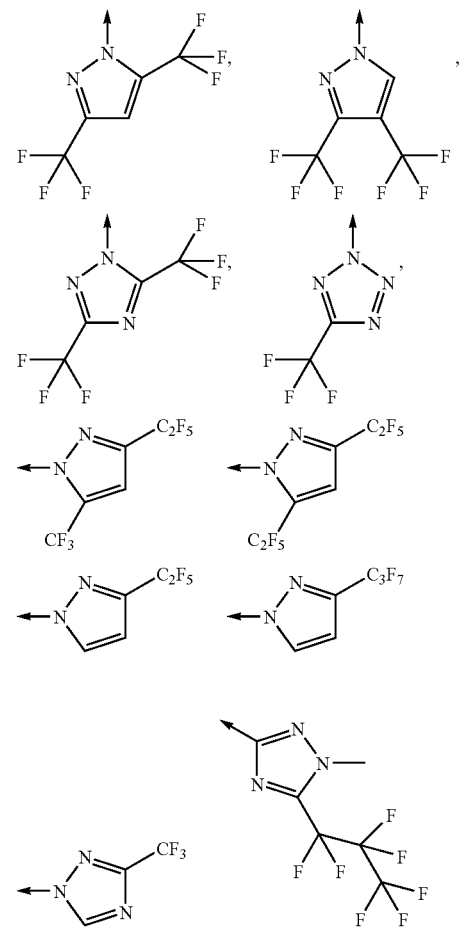

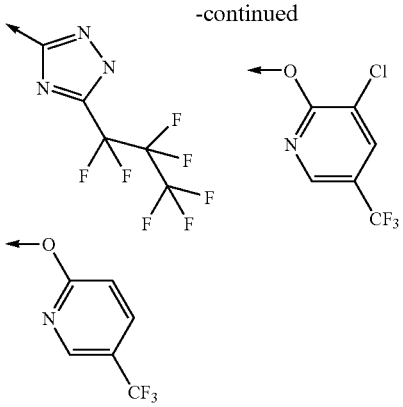

where the arrow indicates the point of attachment to the CH$_2$, group.

R$^6$ most preferably represents hydrogen.

In the preferred definitions, unless indicated otherwise, halogen (also in radicals such as, for example, haloalkyl) is selected from the group consisting of fluorine, chlorine, bromine and iodine, preferably from the group consisting of fluorine, chlorine and bromine, heteroaryl or hetaryl (also as part of a larger moiety such as, for example, heteroarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl (also as part of a larger moiety such as, for example, heterocyclylalkyl) is selected from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

In the particularly preferred definitions, unless indicated otherwise, halogen is selected from the group consisting of fluorine, chlorine, bromine and iodine, preferably from the group consisting of fluorine, chlorine and bromine, heteroaryl or hetaryl (also as part of a larger moiety such as, for example, hetarylalkyl) is selected from the group consisting of pyrimidyl, oxadiazolyl, oxazolyl, pyrazinyl, imidazolyl, thiazolyl and furanyl, pyrrolyl, pyrazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, heterocyclyl (also as part of a larger moiety such as, for example, heterocyclylalkyl) is selected from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

Halogen-substituted radicals, for example haloalkyl, are mono- or polysubstituted up to the maximum possible number of substituents. In the case of polyhalogenation, the halogen atoms can be identical or different. Here, halogen represents fluorine, chlorine, bromine and iodine, in particular fluorine, chlorine and bromine, The general or preferred radical definitions or illustrations given above apply both to the end products and, correspondingly, to starting materials and intermediates. These radical definitions can be combined with one another as desired, i.e. including combinations between the given preferred ranges.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

In a preferred group of compounds of the formula (I), $R^1$ represents cyclopropyl.

In a further preferred group of compounds of the formula (I), $R^7$ represents ethyl.

In a further preferred group of compounds of the formula (I), $R^7$ represents $CH_2CF_3$.

In a further preferred group of compounds of the formula (I), $R^5$ represents optionally substituted phenyl.

In a further preferred group of compounds of the formula (I), $R^5$ represents optionally substituted 3-pyridyl.

If, in the Process 1 according to the invention for preparing the novel compounds of the formula (I), the compound of the formula (II) used is, for example, 6-(4-chlorophenyl)-N-cyclopropylpyrimidine-4,5-diamine and the compound of the formula (III) used is 2-ethylnicotinoyl chloride, Process 1 can be represented by Reaction Scheme I below:

Reaction Scheme I

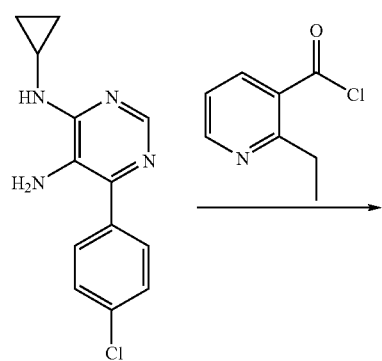

-continued

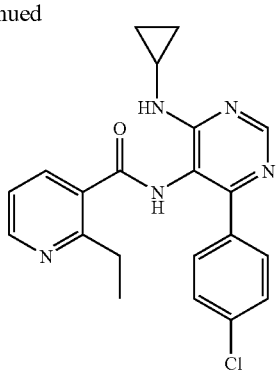

This reaction is generally carried out by reacting compounds of the formula (II) with compounds of the formula (III) in the presence of a basic auxiliary in a diluent at a temperature of from −40° C. to 120° C.

Suitable basic auxiliaries are amines, for example trialkylamines or pyridines. Pyridine may be mentioned by way of example.

In general, it is advantageous to react the compounds of the formula (II) with compounds of the foimula (III) in a diluent. If appropriate, it may also be possible to employ mixtures of diluents for this purpose. Diluents are advantageously employed in such an amount that the reaction mixture remains readily stirrable during the entire process. Suitable diluents for carrying out the Process 1 according to the invention are organic solvents which are inert under the reaction conditions.

Examples which may be mentioned are: halogenated hydrocarbons, in particular chlorinated hydrocarbons, such as tetrachloroethylene, tetrachloroethane, dichloropropane, methylene chloride (DCM), dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; ethers, such as ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide.

After the reaction has ended, the entire reaction mixture is concentrated. The products obtained after work-up can be purified in a customary manner by recrystallization, distillation under reduced pressure or column chromatography (cf. also the Preparation Examples).

Some of the compounds of the formula (II) can be obtained commercially or by methods known from the literature (cf. Journal of Combinatorial Chemistry (2003), 5(5), 653-659, and also the Preparation Examples).

The formula (III) describes the compounds furthermore to be used as starting materials for carrying out Process 1 according to the invention.

In formula (III), $R^4$ has the meanings already mentioned in connection with the description of the compounds of the formula (I) according to the invention.

Some of the compounds of the formula (III) are known and can be obtained commercially or by methods known from the literature (cf. Chemical Communications (2008), 4207-4209, and Methods of Organic Synthesis (2002) Volume E22a, Ed. Murray Goodman, JP401316361A and also Mendeleev Communications (2006) (3), 161-163).

If, in Process 2 according to the invention for preparing the compounds of the formula (I), the compound of the formula (IV) used is, for example, N-(4-chloro-6-cyclopropylaminopyrimidin-5-yl)-2-ethylnicotinamide and the compound of the formula (V) is 2,4-dichlorophenylboronic acid, the process can be represented by Reaction Scheme II below:

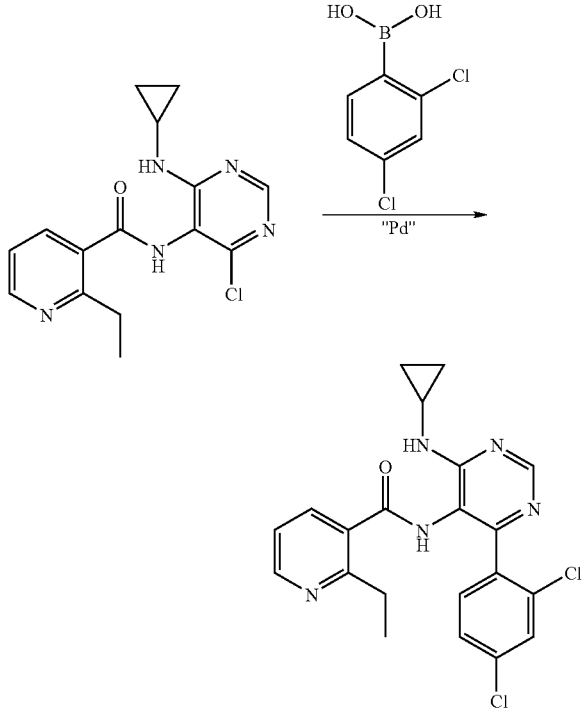

The compound of the formula (IV) is reacted in a suitable diluent, such as, for example, alcohols (for example methanol or ethanol), ethers (for example diethyl ether or dioxane) or water or a mixture of these diluents (for example dioxane/water), if appropriate in the presence of a base and in the presence of suitable palladium catalysts and bases in a temperature range of from −20° C. to 120° C. in suitable solvents (Suzuki reaction).

Suitable bases are inorganic or organic bases, in particular carbonates, such as, for example, sodium carbonate.

A large number of palladium catalysts can be employed. Preference is given to using a catalyst from the group consisting of $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $Pd(PPh_3)_4$.

Some of the compounds of the formula (IV) are known and can be prepared by known methods described, for example, in Tetrahedron Letters, 49(13), 2143-2145; 2008.

Some of the boronic acids or boronic esters of the formula (V) are commercially available, or they can be prepared by known methods. This is described, for example, in WO 1999/64428.

After the reaction has ended, the entire reaction mixture is concentrated. The products obtained after work-up can be purified in a customary manner by recrystallization, distillation under reduced pressure or column chromatography (cf. also the Preparation Examples).

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp.,

*Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control Protozoa, such as *Eimeria*.

From the order of the Heteroptera, for example, *Anasa tristis*, *Antestiopsis* spp., *Blissus* spp., *Cabocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips Havens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with foimaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights.

Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The compounds according to the invention are particularly suitable for the treatment of seed. Thus, most of the damage to crop plants which is caused by pests occurs as early as when the seed is infested during storage and after the seed is introduced into the soil, and during and immediately after germination of the plants. This phase is particularly critical since the roots and shoots of the growing plants are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after planting or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection products being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the germinating plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

Furthermore, it must be considered as advantageous that the compounds according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and, in addition, the seed can be protected from damage by the composition according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potato or vegetables (e.g. tomatoes or brassicas). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

Within the scope of the present invention, the active compounds according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of (transgenic) plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the formula (I). The preferred ranges stated above for the active compounds also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongyles* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combination with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example 1

Precursor

6-Chloro-N-methylpyrimidine-4,5-diamine

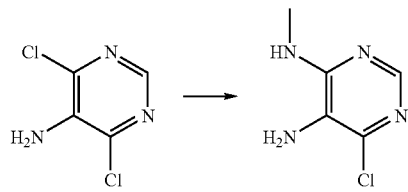

5-Amino-4,6-dichloropyrimidine (15.0 g, 91.4 mmol) and methylamine (2M solution in THF, 5 eq) were initially charged, and triethylamine (27.76 g, 274 mmol) was added. The mixture was stirred under reflux until the conversion was complete (about 3 hours). The reaction mixture was then concentrated, and water was added to the residue. The pH was adjusted to 7-8 using saturated Na—HCO₃ solution. The mixture was extracted 3× with methylene chloride, the combined organic phases were dried over sodium sulphate and filtered and the solvent was removed under reduced pressure.

Yield: 12.0 g (82%)

LC-MS: M+(ES+)159(100%)

NMR DMSO 2.89 (3H, m), 4.77 (2H, s), 6.71 (1H, s), 7.75 (1H, s).

Example 2

Precursor

N-(4-Chloro-6-cyclopropylaminopyrimidin-5-yl)-2-ethylnicotinamide

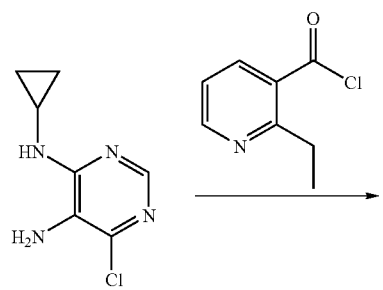

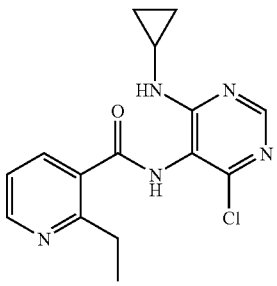

6-Chloro-N-cyclopropylpyrimidine-4,5-diamine (cf. Journal of Combinatorial Chemistry (2003), 5(5), 653-659) (3.0 g, 16.2 mmol) was initially charged in a mixture of methylene chloride (12.20 ml) and pyridine (3.94 ml). The suspension was cooled to 0° C., and solid 2-ethylnicotinoyl chloride (1.2 eq) was added. The reaction mixture was allowed to warm to room temperature and stirred until the reaction had gone to completion. 10 ml of methylene chloride were then added, the suspension turning into a solution. About 10 ml of semisaturated NaHCO₃ solution were added to the organic phase whilst the mixture was stirred vigorously in a flask using a magnetic stirrer; poorly soluble crystals (product) precipitated and were filtered off with suction, washed 3× with a little water and 3× with n-heptane and dried.

Fraction 1: 3.41 g, 66%

LC/MS:M+(ES+)=318 (100%)

NMR 0.56 (2H, m), 0.76 (2H, m), 1.25 (3H, t), 2.87 (1H, m), 2.96 (2H, q), 7.22 (1H, s), 7.32 (1H, m), 8.10 (1H, m), 8.30 (1H, m), 8.59 (1H, m), 9.55 (1H, m).

Example 3

End Product

N-[4-Cyclopropylamino-6-(2,4-dichlorophenyl)pyrimidin-5-yl]-2-ethylnicotinamide

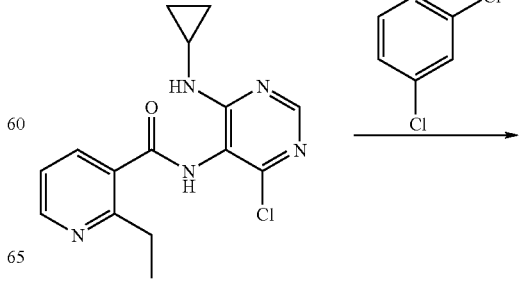

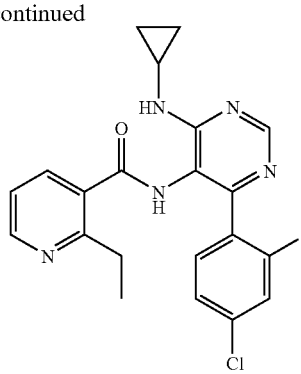

In a test tube which had been dried by heating and preheated to 100° C., the degassed diluent mixture dioxane (2 ml)/water (0.7 ml) was added to N-(4-chloro-6-cyclopropylaminopyrimidin-5-yl)-2-ethylnicotinamide (0.41 mmol), sodium carbonate (3 eq) and 2,4-dichlorophenylboronic acid (2 eq). 5 mol % of tetrakis(triphenylphosphine)palladium(0) were added, and the reaction mixture was stirred at 90° C. for 3 hours. The mixture was then diluted with water and extracted 3× with methylene chloride, and the combined organic phases were washed with aqueous NaHCO$_3$ solution, dried 20 over Na$_2$SO$_4$, filtered and concentrated under reduced pressure.

LC/MS: M+(ES+)=430 (50%) NMR DMSO 0.57 (2H, m), 0.79 (2H, m), 1.03 (3H, t), 2.91 (1H, m), 6.86 (1H, m), 7.263 (1H, m), 7.44 (2H, m), 7.61 (1H, m), 7.72 (1H, m), 8.50 (2H, m), 9.33 (1H, s).

The residue was separated on a Companion using a Chromabond Flash RS 70 SiOH cartrige and methylene chloride/MeOH.

LC/MS: M+(ES+)=428 (100%)

Example 4

Precursor 6-(4-Chlorophenyl)-N-cyclopropylpyrimidine-4,5-diamine

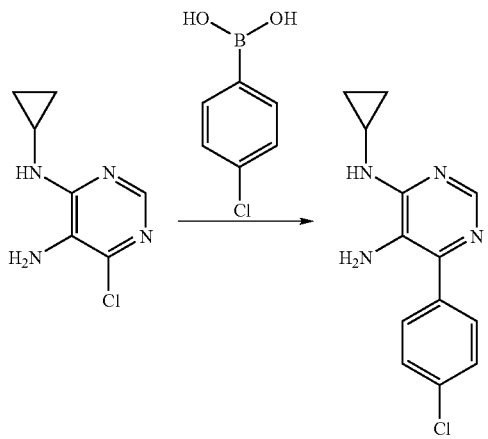

In a reactor carousel test tube which had been dried by heating and preheated to 100° C., the degassed diluent mixture dioxane (20 ml)/water (7 ml) was added to 6-chloro-N-cyclopropylpyrimidine-4,5-diamine (10 g, 54.1 mmol) and sodium carbonate (17.22 g, 162 mmol). 5 mol % of tetrakis (triphenylphosphine)palladium(0) and 4-chlorophenylboronic acid (108.2 mmol) were added, and the reaction mixture was stirred at 90° C. overnight. The solution was cooled, filtered and concentrated and the residue was recrystallised from acetonitrile.

Yield: 8193 mg; 58%

LC-MS: M+(ES)=261 (100%)

NMR DMSO 0.52 (2H, m), 0.53 (2H, m), 2.89 (1H, m), 4.52 (1H, s), 6.76 (1H, s), 7.47 (2H, m), 7.65 (2H, m), 8.04 1H, s).

Example 5

End Product

N-[4-(4-Chlorophenyl)-6-cyclopropylaminopyrimidin-5-yl]-2-ethylnicotinamide

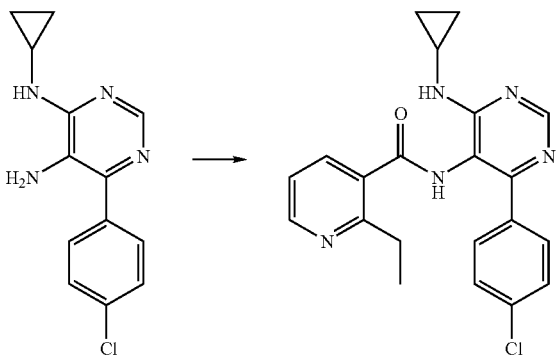

6-(4-Chlorophenyl)-N-cyclopropylpyrimidine-4,5-diamine (1.00 g, 3.83 mmol) was initially charged in a mixture of DCM (3.20 ml) and pyridine (0.93 ml) and cooled to 0° C. Solid 2-ethylnicotinoyl chloride (780 mg, 4.60 mmol) was added, and the reaction mixture was warmed to room temperature and stirred for another hour. After addition of semi-saturated NaHCO$_3$ solution, the organic phase was separated off and concentrated under reduced pressure.

The residue was separated on a Companion using a Chromabond Flash RS 120 SiOH cartrige and DCM/MeOH.

Fraction 1: 394 mg; 25%

LC/MS: M+(ES+)=394 (98%) NMR DMSO 0.55 (2H, m), 0.78 (2H, m), 1.063 (3H, t), 2.89 (1H, m), 6.94 (1H, s), 7.28 (1H, m), 7.45 (2H, d), 7.67 (2H, d), 7.88 (1H, d), 8.52 (2H, m), 9.37 (1H, s).

Example 6

6-Chloro-N$^4$-[4-(trifluoromethyl)phenyl]pyrimidine-4,5-diamine (cf. also Tetrahedron Letters., 48, 1489 (2007))

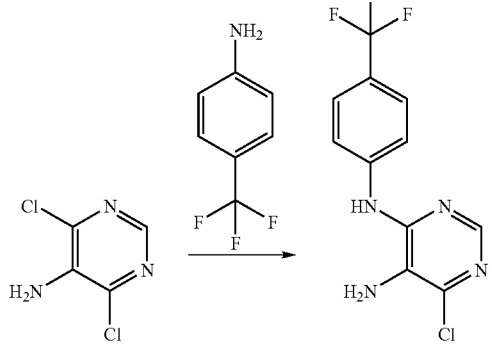

A mixture of 4,6-dichloroaminopyrimidine (1.5 g), isopropanol (20 ml), 4-trifluoromethylaniline (1.47 g) and a drop of conc. aqueous hydrochloric acid was heated in a microwave vessel at 150° C. for 10 min. After cooling, the precipitate obtained was filtered off.

Yield 580 mg.

Example 7

N-(4-Chloro-6-{[4-(trifluoromethyl)phenyl]amino}pyrimidin-5-yl)-2-ethylnicotinamide

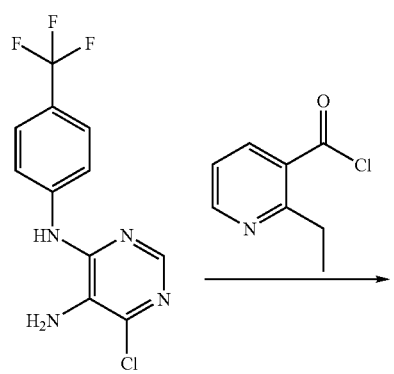

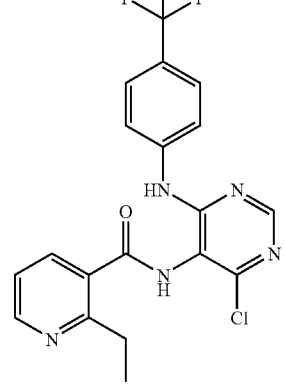

The compound from Example 6 (349 mg) was initially charged in a mixture of methylene chloride (3 ml) and pyridine (0.35 ml). The suspension was cooled to 0° C., and solid 2-ethylnicotinoyl chloride (1.2 eq) was added. The reaction mixture was allowed to warm to room temperature and stirred until the reaction had gone to completion. 10 ml of methylene chloride were then added, the suspension turning into a solution. After addition of semisaturated $NaHCO_3$ solution, the mixture was stirred and the organic phase was separated off and concentrated under reduced pressure.

The residue was separated on a Companion using a Chromabond Flash RS 120 SiOH cartrige and hexane/ethyl acetate.

Fraction 1: 240 mg; 38%

Other compounds according to the invention are listed in the table below.

The following abbreviations are used:

Ph=Phenyl=Ar

R in column $R^1$ (cf., for example, Ex. Nos. 1-222, 1-229, 1-230, 1-250, 3-7 etc.) denotes the point of attachment to the remainder of the molecule.

TABLE 1

Compounds of the formula

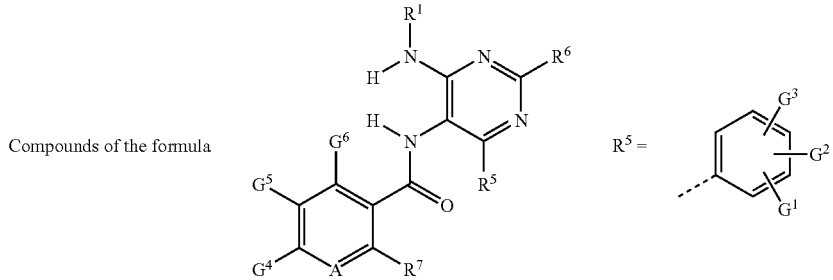

$R^5 =$ 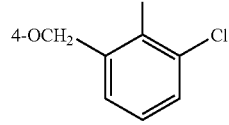

| Ex. No. | $R^1$ | $R^7$ | $G^1$ | $G^2$ | $G^3$ | $R^6$ | A | $G^4$ | $G^5$ | $G^6$ |
|---|---|---|---|---|---|---|---|---|---|---|
| 1-1 | cyclopropyl | $CH_3$ | 4-F | H | H | H | N | H | H | H |
| 1-2 | cyclopropyl | $CH_3$ | 4-OCH$_2$-(2,4-dichlorophenyl) | H | H | H | N | H | H | H |
| 1-3 | cyclopropyl | $CH_3$ | 4-OCH$_2$-(2,3-dichlorophenyl) | H | H | H | N | H | H | H |

TABLE 1-continued

Compounds of the formula

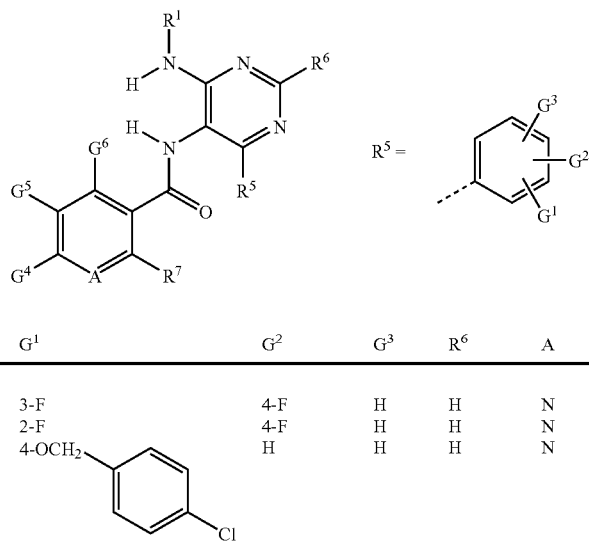

| Ex. No. | R¹ | R⁷ | G¹ | G² | G³ | R⁶ | A | G⁴ | G⁵ | G⁶ |
|---|---|---|---|---|---|---|---|---|---|---|
| 1-4 | cyclopropyl | CH$_2$CH$_3$ | 3-F | 4-F | H | H | N | H | H | H |
| 1-5 | cyclopropyl | CH$_2$CH$_3$ | 2-F | 4-F | H | H | N | H | H | H |
| 1-6 | cyclopropyl | CH$_2$CH$_3$ | 4-OCH$_2$(4-Cl-C$_6$H$_4$) | H | H | H | N | H | H | H |
| 1-7 | cyclopropyl | CH$_2$CH$_3$ | 4-OCH$_3$ | H | H | H | N | H | H | H |
| 1-8 | cyclopropyl | CH$_2$CH$_3$ | 4-CH$_3$ | H | H | H | N | H | H | H |
| 1-9 | cyclopropyl | CH$_2$CH$_3$ | 2-F | 3-F | H | H | N | H | H | H |
| 1-10 | cyclopropyl | CH$_2$CH$_3$ | 4-SCH$_3$ | H | H | H | N | H | H | H |
| 1-11 | cyclopropyl | CH$_2$CH$_3$ | 2-F | H | H | H | N | H | H | H |
| 1-12 | cyclopropyl | CH$_2$CH$_3$ | 3,4-OCH$_2$CH$_2$—O— | | H | H | N | H | H | H |
| 1-13 | cyclopropyl | CH$_2$CH$_3$ | 3-Cl | H | H | H | N | H | H | H |
| 1-14 | cyclopropyl | CH$_2$CH$_3$ | 3-NH$_2$ | H | H | H | N | H | H | H |
| 1-15 | cyclopropyl | CH$_2$CH$_3$ | 3-F | 4-F | 5-F | H | N | H | H | H |
| 1-16 | cyclopropyl | CH$_2$CH$_3$ | 2-F | 3-F | 4-F | H | N | H | H | H |
| 1-17 | cyclopropyl | CH$_2$CH$_3$ | 4-COCH$_3$ | H | H | H | N | H | H | H |
| 1-18 | cyclopropyl | CH$_2$CH$_3$ | 4-C(CH$_3$)$_3$ | H | H | H | N | H | H | H |
| 1-19 | cyclopropyl | CH$_2$CH$_3$ | 4-N(CH$_3$)$_2$ | H | H | H | N | H | H | H |
| 1-20 | cyclopropyl | CH$_2$CH$_3$ | 3-Cl | 4-F | H | H | N | H | H | H |
| 1-21 | CH(CH$_3$)$_2$ | CH$_2$CH$_3$ | 4-F | H | H | H | N | H | H | H |
| 1-22 | CH(CH$_3$)$_2$ | CH$_2$CH$_3$ | 4-OCF$_3$ | H | H | H | N | H | H | H |
| 1-23 | CH(CH$_3$)CH$_2$SCH$_3$ | CH$_2$CH$_3$ | 4-OCF$_3$ | H | H | H | N | H | H | H |
| 1-24 | CH(CH$_3$)CH$_2$SCH$_3$ | CH$_2$CH$_3$ | 4-F | H | H | H | N | H | H | H |
| 1-25 | cyclopropyl | CH$_2$CH$_3$ | 2-F | 3-Cl | H | H | N | H | H | H |
| 1-26 | cyclopropyl | CH$_2$CH$_3$ | 3,4-OCF$_2$O | | H | H | N | H | H | H |
| 1-27 | cyclopropyl | CH$_2$CH$_3$ | 3-CH$_3$ | 4-F | H | H | N | H | H | H |
| 1-28 | cyclopropyl | CH$_2$CH$_3$ | 3-C(CH$_3$)NOCH$_3$ | H | H | H | N | H | H | H |
| 1-29 | cyclopropyl | CH$_2$CH$_3$ | 3-CHNOCH$_3$ | H | H | H | N | H | H | H |
| 1-30 | cyclopropyl | CH$_2$CH$_3$ | 2-F | 5-CF$_3$ | H | H | N | H | H | H |
| 1-31 | cyclopropyl | CH$_2$CH$_3$ | CONH$_2$ | H | H | H | N | H | H | H |
| 1-32 | cyclopropyl | CH$_2$CH$_3$ | 3,4-OCH$_2$O— | | H | H | N | H | H | H |
| 1-33 | cyclopropyl | CH$_2$CH$_3$ | 3-NH$_2$ | OCH$_3$ | 5-NH$_2$ | H | N | H | H | H |
| 1-34 | cyclopropyl | CH$_2$CH$_3$ | 4-CO$_2$CH$_3$ | H | H | H | N | H | H | H |
| 1-35 | cyclopropyl | CH$_2$CH$_3$ | 3-SCH$_3$ | H | H | H | N | H | H | H |
| 1-36 | cyclopropyl | CH$_2$CH$_3$ | 4-CH$_2$OCH$_3$ | H | H | H | N | H | H | H |
| 1-37 | cyclopropyl | CH$_2$CH$_3$ | 2-F | 4-F | 5-Cl | H | N | H | H | H |
| 1-38 | cyclopropyl | CH$_2$CH$_3$ | 3-CH$_2$OCH$_3$ | H | H | H | N | H | H | H |
| 1-39 | cyclopropyl | CH$_2$CH$_3$ | 4-NHCOCH$_3$ | H | H | H | N | H | H | H |
| 1-40 | cyclopropyl | CH$_2$CH$_3$ | 3-F | 4-NH$_2$ | H | H | N | H | H | H |
| 1-41 | cyclopropyl | CH$_2$CH$_3$ | 3-F | 4-OCH$_3$ | H | H | N | H | H | H |
| 1-42 | cyclopropyl | CH$_2$CH$_3$ | 3-F | 4-CH$_3$ | H | H | N | H | H | H |
| 1-43 | cyclopropyl | CH$_2$CH$_3$ | 2-F | 4-CF$_3$ | H | H | N | H | H | H |
| 1-44 | cyclopropyl | CH$_2$CH$_3$ | 3-F | 4-Cl | H | H | N | H | H | H |
| 1-45 | cyclopropyl | CH$_2$CH$_3$ | 2-F | 5-COCH$_3$ | H | H | N | H | H | H |
| 1-46 | cyclopropyl | CH$_2$CH$_3$ | 3-F | 5-OCH$_3$ | H | H | N | H | H | H |
| 1-47 | cyclopropyl | CH$_2$CH$_3$ | 2-F | 5-CH$_3$ | H | H | N | H | H | H |
| 1-48 | cyclopropyl | CH$_2$CH$_3$ | 2-F | 4-OCH$_3$ | H | H | N | H | H | H |
| 1-49 | cyclopropyl | CH$_2$CH$_3$ | 3-F | 5-Cl | H | H | N | H | H | H |
| 1-50 | cyclopropyl | CH$_2$CH$_3$ | 3-S(O)$_2$CH$_3$ | H | H | H | N | H | H | H |
| 1-51 | cyclopropyl | CH$_2$CH$_3$ | 3-CN | 4-F | H | H | N | H | H | H |
| 1-52 | cyclopropyl | CH$_2$CH$_3$ | 2-F | 3-OCH$_3$ | H | H | N | H | H | H |
| 1-53 | cyclopropyl | CH$_2$CH$_3$ | 3-Si(CH$_3$)$_3$ | H | H | H | N | H | H | H |
| 1-54 | cyclopropyl | CH$_2$CH$_3$ | 2-OCH$_3$ | 4-F | H | H | N | H | H | H |
| 1-55 | cyclopropyl | CH$_2$CH$_3$ | 3-NO$_2$ | H | H | H | N | H | H | H |
| 1-56 | cyclopropyl | CH$_2$CH$_3$ | 2-Cl | 5-Cl | H | H | N | H | H | H |
| 1-57 | cyclopropyl | CH$_2$CH$_3$ | 3-CH$_3$ | 5-CH$_3$ | H | H | N | H | H | H |
| 1-58 | cyclopropyl | CH$_2$CH$_3$ | 3-Ar | H | H | H | N | H | H | H |
| 1-59 | cyclopropyl | CH$_2$CH$_3$ | 2-Cl | 5-Cl | H | H | N | H | H | H |

TABLE 1-continued

Compounds of the formula 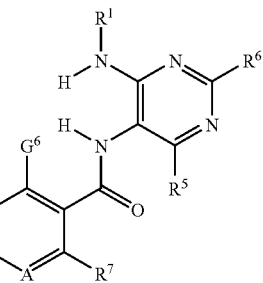  R⁵ = 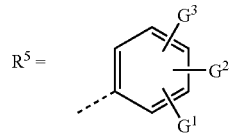

| Ex. No. | R¹ | R⁷ | G¹ | G² | G³ | R⁶ | A | G⁴ | G⁵ | G⁶ |
|---|---|---|---|---|---|---|---|---|---|---|
| 1-60 | cyclopropyl | CH₂CH₃ | 4-CH₂CH₃ | H | H | H | N | H | H | H |
| 1-61 | cyclopropyl | CH₂CH₃ | 2-Cl | 3-Cl | H | H | N | H | H | H |
| 1-62 | cyclopropyl | CH₂CH₃ | 4-Ar | H | H | H | N | H | H | H |
| 1-63 | cyclopropyl | CH₂CH₃ | 3-CH₃ | 4-CH₃ | H | H | N | H | H | H |
| 1-64 | cyclopropyl | CH₂CH₃ | 4-O-phenyl | | | H | N | H | H | H |
| 1-65 | cyclopropyl | CH₂CH₃ | 2-F | 4-OCH₃ | 5-F | H | N | H | H | H |
| 1-66 | cyclopropyl | CH₂CH₃ | 3-NH(SO₂)CH₃ | H | H | H | N | H | H | H |
| 1-67 | cyclopropyl | CH₂CH₃ | CH₂CH₂-phenyl | H | H | H | N | H | H | H |
| 1-68 | cyclopropyl | CH₂CH₃ | 4-OCH(CH₃) | H | H | H | N | H | H | H |
| 1-69 | cyclopropyl | CH₂CH₃ | 3-Cl | 4-Cl | 5-Cl | H | N | H | H | H |
| 1-70 | cyclopropyl | CH₂CH₃ | 4-NO₂ | H | H | H | N | H | H | H |
| 1-71 | cyclopropyl | CH₂CH₃ | 3-F | 5-NH₂ | H | H | N | H | H | H |
| 1-72 | cyclopropyl | CH₃ | 4-OCF₃ | H | H | H | CH | H | H | H |
| 1-73 | cyclopropyl | CH₂CH₃ | 4-OCF₃ | H | H | H | N | H | H | H |
| 1-74 | CH(CH₃)₂ | CH₃ | 4-OCF₃ | H | H | H | N | H | H | H |
| 1-75 | cyclopropyl | Cl | 4-OCF₃ | H | H | H | N | H | H | H |
| 1-76 | CH(CH₃)₂ | Cl | 4-OCF₃ | H | H | H | N | H | H | H |
| 1-77 | CH(CH₃)₂ | CH₃ | 4-OCF₃ | H | H | H | CH | H | H | H |
| 1-78 | CH(CH₃)₂ | H | OCF₃ | H | H | H | CH | H | H | H |
| 1-79 | CH(CH₃)₂ | Cl | 4-OCF₃ | H | H | H | CH | H | H | H |
| 1-80 | cyclopropyl | Cl | 4-CF₃ | H | H | H | CH | H | H | H |
| 1-81 | cyclopropyl | CH₃ | 4-CF₃ | H | H | H | CH | H | H | H |
| 1-82 | cyclopropyl | Cl | 4-CF₃ | H | H | H | N | H | H | H |
| 1-83 | cyclopropyl | CH₃ | 4-CF₃ | H | H | H | N | H | H | H |
| 1-84 | cyclopropyl | CF₃ | 4-CF₃ | H | H | H | N | H | H | H |
| 1-85 | cyclopropyl | CH(CH₃)₂ | 4-CF₃ | H | H | H | N | H | H | H |
| 1-86 | cyclopropyl | CH₂CH₃ | 4-CF₃ | H | H | H | CH | H | H | H |
| 1-87 | cyclopropyl | CH₃ | 4-CF₃ | H | H | CH₃ | N | H | H | H |
| 1-88 | cyclopropyl | Cl | 4-CF₃ | H | H | CH₃ | CH | H | H | H |
| 1-89 | cyclopropyl | CH₃ | 4-CF₃ | H | H | cyclopropyl | N | H | H | H |
| 1-90 | CH(CH₃)₂ | CH₃ | 4-OCF₃ | H | H | H | N | H | H | H |
| 1-91 | CH(CH₃)—cyclopropyl | CH₃ | 4-OCF₃ | H | H | H | N | H | H | H |
| 1-92 | CH(CH₃)CH₂CH₃ | CH₃ | 4-OCF₃ | H | H | H | N | H | H | H |
| 1-93 | cyclopropyl | CH₃ | 4-OCF₃ | H | H | H | N | H | H | H |
| 1-94 | CH(CH₃)₂ | CH₃ | 4-OCF₃ | H | H | H | N | H | H | H |
| 1-95 | CH(CH₃)—cyclopropyl | CH₃ | 4-OCF₃ | H | H | H | N | H | H | H |
| 1-96 | cyclopropyl | CH₃ | 4-OCF₃ | H | H | H | N | H | H | H |
| 1-97 | cyclopropyl | CH₃ | 4-OCF₃ | H | H | C(CH₃) | N | H | H | H |
| 1-98 | cyclopropyl | CH₃ | 4-OCF₃ | H | H | 4-Cl—Ph | N | H | H | H |
| 1-99 | CH(CH₃)—cyclopropyl | Cl | 4-OCF₃ | H | H | H | N | H | H | H |

TABLE 1-continued

Compounds of the formula 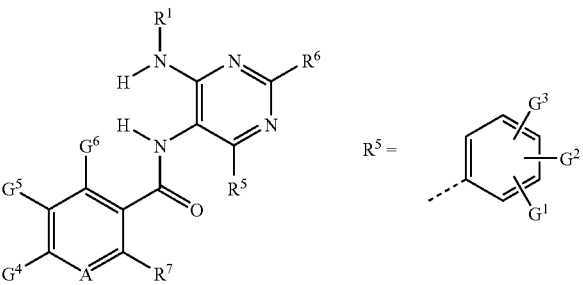 R⁵ = 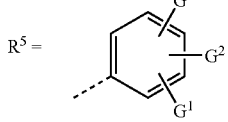

| Ex. No. | R¹ | R⁷ | G¹ | G² | G³ | R⁶ | A | G⁴ | G⁵ | G⁶ |
|---|---|---|---|---|---|---|---|---|---|---|
| 1-100 | C(CH₃)₂-cyclopropyl | CH₃ | 4-OCF₃ | H | H | H | N | H | H | H |
| 1-101 | CH(CH₃)CH₂CH₃ | CH₃ | 4-OCF₃ | H | H | H | N | H | H | H |
| 1-102 | CH(CH₃)CH₂CH₃ | Cl | 4-OCF₃ | H | H | H | N | H | H | H |
| 1-103 | CH₂-cyclopropyl | CH₃ | 4-OCF₃ | H | H | H | N | H | H | H |
| 1-104 | CH₂-cyclopropyl | Cl | 4-OCF₃ | H | H | H | N | H | H | H |
| 1-105 | C(CH₃)₃ | Cl | 4-OCF₃ | H | H | H | N | H | H | H |
| 1-106 | CH(CH₂CH₃)₂ | CH₃ | 4-OCF₃ | H | H | H | N | H | H | H |
| 1-107 | CH(CH₂CH₃)₃ | Cl | 4-OCF₃ | H | H | H | N | H | H | H |
| 1-108 | CH(CH₃)CH(CH₃)₂ | CH₃ | 4-OCF₃ | H | H | H | N | H | H | H |
| 1-109 | CH(CH₃)CH(CH₃)₃ | Cl | 4-OCF₃ | H | H | H | N | H | H | H |
| 1-110 | CH(-cyclopropyl)₂ | CH₃ | 4-OCF₃ | H | H | H | N | H | H | H |
| 1-111 | CH(-cyclopropyl)₂ | Cl | 4-OCF₃ | H | H | H | N | H | H | H |
| 1-112 | cyclopropyl | H | 4-OCF₃ | H | H | H | CH | H | H | H |
| 1-113 | cyclopropyl | Cl | 4-OCF₃ | H | H | H | CH | H | H | H |
| 1-114 | cyclopropyl | CH₂CH₃ | 4-SCF₃ | H | H | H | N | H | H | H |
| 1-115 | cyclopropyl | CH₂CH₃ | 3-NH₂ | 4-OCH(CH₃)₂ | H | H | N | H | H | H |
| 1-116 | cyclopropyl | CH₃ | 4-SCF₃ | H | H | H | N | H | H | H |
| 1-117 | cyclopropyl | CH₃ | S(O)CF₃ | H | H | H | N | H | H | H |
| 1-118 | cyclopropyl | CH₃ | S(O)CHF₂ | H | H | H | N | H | H | H |
| 1-119 | cyclopropyl | CH₃ | OCH₂-(4-Cl-phenyl) | H | H | H | H | N | H | H |
| 1-120 | cyclopropyl | CH₃ | OCF₃ | CH₃ | H | H | N | H | H | H |
| 1-121 | cyclopropyl | CH₃ | 4-OSO₂CH(CH₃)₂ | H | H | H | N | H | H | H |
| 1-122 | cyclopropyl | CH₃ | 3-F | 4-CF₃ | 5-F | H | N | H | H | H |
| 1-123 | cyclopropyl | CH₃ | 4-OCF₂CHFCF₃ | 4-CF₃ | H | H | N | H | H | H |
| 1-124 | cyclopropyl | CH₂CH₃ | 4-F | H | H | H | N | H | H | H |
| 1-125 | CH₃ | CH₂CH₃ | 4-F | H | H | H | N | H | H | H |
| 1-126 | cyclopropyl | CH₂CH₃ | 2-Cl | 4-Cl | H | H | N | H | H | H |
| 1-127 | cyclopropyl | CH₂CH₃ | H | H | H | H | N | H | H | H |
| 1-128 | cyclopropyl | H | H | H | H | H | N | H | H | H |
| 1-129 | cyclopropyl | Cl | 4-F | H | H | H | N | H | H | H |
| 1-130 | cyclopropyl | Cl | 4-Cl | H | H | H | N | H | H | H |
| 1-131 | cyclopropyl | Br | 4-Cl | H | H | H | N | H | H | H |
| 1-132 | cyclopropyl | Br | 4-F | H | H | H | N | H | H | H |
| 1-133 | cyclopropyl | CH₂CH₃ | 4-CN | H | H | H | N | H | H | H |
| 1-134 | C(CH₃)₃ | CH₂CH₃ | 4-F | H | H | H | N | H | H | H |
| 1-135 | C(CH₃)₃ | CH₂CH₃ | 4-Cl | H | H | H | N | H | H | H |
| 1-136 | C(CH₃)₃ | CH₂CH₃ | 4-CN | H | H | H | N | H | H | H |
| 1-137 | C(CH₃)₃ | CH₂CH₃ | 4-CF₃ | H | H | H | N | H | H | H |
| 1-138 | C(CH₃)₃ | CH₂CH₃ | OCF₃ | H | H | H | N | H | H | H |
| 1-139 | cyclopropyl | CH₂CH₃ | 2-Cl | 4-F | H | H | N | H | H | H |
| 1-140 | cyclopropyl | CH₂CH₃ | 2-Cl | H | H | H | N | H | H | H |

TABLE 1-continued

Compounds of the formula 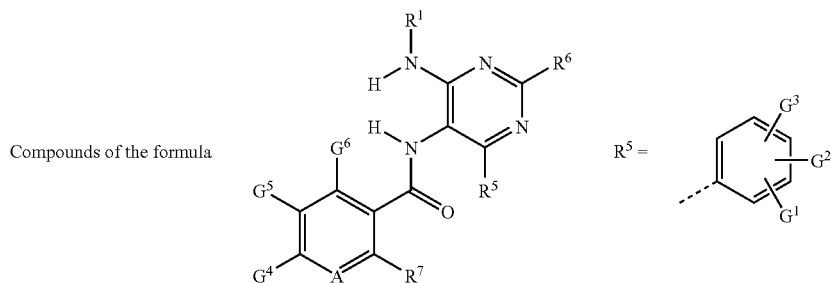

| Ex. No. | R¹ | R⁷ | G¹ | G² | G³ | R⁶ | A | G⁴ | G⁵ | G⁶ |
|---|---|---|---|---|---|---|---|---|---|---|
| 1-141 | C(CH$_3$)$_3$ | CH$_2$CH$_3$ | 3-NH$_2$ | 4-F | H | H | N | H | H | H |
| 1-142 | C(CH$_3$)$_3$ | CH$_2$CH$_3$ | 2-Cl | 4-Cl | H | H | N | H | H | H |
| 1-143 | CH(CH$_3$)-cyclopropyl | CH$_2$CH$_3$ | 4-F | H | H | H | N | H | H | H |
| 1-144 | CH(CH$_3$)-cyclopropyl | CH$_2$CH$_3$ | 4-Cl | H | H | H | N | H | H | H |
| 1-145 | CH(CH$_3$)-cyclopropyl | CH$_2$CH$_3$ | 4-CN | H | H | H | N | H | H | H |
| 1-146 | CH(CH$_3$)-cyclopropyl | CH$_2$CH$_3$ | 4-OCF$_3$ | H | H | H | N | H | H | H |
| 1-147 | CH(CH$_3$)-(1-Cl-cyclopropyl) | CH$_2$CH$_3$ | 4-F | H | H | H | N | H | H | H |
| 1-148 | CH(CH$_3$)-(1-Cl-cyclopropyl) | CH$_2$CH$_3$ | 2-Cl | 4-Cl | H | H | N | H | H | H |
| 1-149 | CH(CH$_3$)-(1-Cl-cyclopropyl) | CH$_2$CH$_3$ | 4-Cl | H | H | H | N | H | H | H |
| 1-150 | CH(CH$_3$)-(1-Cl-cyclopropyl) | CH$_2$CH$_3$ | 4-CN | H | H | H | N | H | H | H |
| 1-151 | C(CH$_3$)$_2$-cyclopropyl | CH$_2$CH$_3$ | 4-Cl | H | H | H | N | H | H | H |
| 1-152 | CH(CH$_3$)-cyclopropyl | CH$_2$CH$_3$ | H | H | H | H | N | H | H | H |
| 1-153 | cyclopropyl | CH$_2$CH$_3$ | 3-CONH-cyclopropyl | H | H | H | N | H | H | H |
| 1-154 | cyclopropyl | OCH$_3$ | 4-Cl | H | H | H | N | H | H | H |
| 1-155 | cyclopropyl | OCH$_3$ | 4-F | H | H | H | N | H | H | H |
| 1-156 | cyclopropyl | OCH$_3$ | 4-CN | H | H | H | N | H | H | H |
| 1-157 | cyclopropyl | OCH$_3$ | 4-OCF$_3$ | H | H | H | N | H | H | H |
| 1-158 | cyclopropyl | OCH$_2$CH$_3$ | 4-Cl | H | H | H | N | H | H | H |
| 1-159 | cyclopropyl | OCH$_2$CH$_3$ | 4-F | H | H | H | N | H | H | H |
| 1-160 | cyclopropyl | OCH$_2$CH$_3$ | 4-CN | H | H | H | N | H | H | H |
| 1-161 | cyclopropyl | OCH$_2$CH$_3$ | 4-OCF$_3$ | H | H | H | N | H | H | H |
| 1-162 | cyclopropyl | O(CH$_3$)$_2$ | 4-Cl | H | H | H | N | H | H | H |
| 1-163 | cyclopropyl | OCH(CH$_3$)$_2$ | 4-F | H | H | H | N | H | H | H |
| 1-164 | cyclopropyl | OCH(CH$_3$)$_2$ | 4-CN | H | H | H | N | H | H | H |
| 1-165 | cyclopropyl | OCH(CH$_3$)$_2$ | 4-OCF$_3$ | H | H | H | N | H | H | H |
| 1-166 | cyclopropyl | OCH$_2$CF$_3$ | 4-Cl | H | H | H | N | H | H | H |
| 1-167 | cyclopropyl | OCH$_2$CF$_3$ | 4-F | H | H | H | N | H | H | H |
| 1-168 | cyclopropyl | OCH$_2$CF$_3$ | 4-CN | H | H | H | N | H | H | H |
| 1-169 | cyclopropyl | OCH$_2$CF$_3$ | 4-OCF$_3$ | H | H | H | N | H | H | H |

TABLE 1-continued

Compounds of the formula 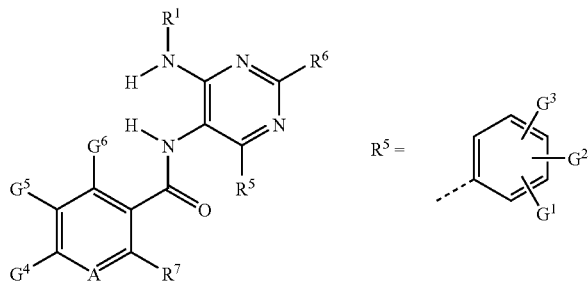 R$^5$ = 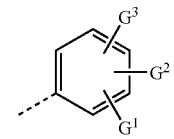

| Ex. No. | R$^1$ | R$^7$ | G$^1$ | G$^2$ | G$^3$ | R$^6$ | A | G$^4$ | G$^5$ | G$^6$ |
|---|---|---|---|---|---|---|---|---|---|---|
| 1-170 | cyclopropyl | CF$_3$ | 4-F | H | H | H | N | H | H | H |
| 1-171 | cyclopropyl | CN | 4-F | H | H | H | N | H | H | H |
| 1-172 | cyclopropyl | CH$_2$—◁ | 4-H | | | | | | | |
| 1-173 | cyclopropyl | CH$_2$—◁ | 4-Cl | H | H | H | N | H | H | H |
| 1-174 | cyclopropyl | CHFCH$_3$ | 4-Cl | H | H | H | N | H | H | H |
| 1-175 | cyclopropyl | CH$_2$CH$_3$ | 3-CONH—◁ | H | H | H | N | H | H | H |
| 1-176 | cyclopropyl | CH$_2$CF$_3$ | 4-Cl | H | H | H | N | H | H | H |
| 1-177 | cyclopropyl | CH$_2$CH$_3$ | 4-Cl | H | H | H | N | H | H | H |
| 1-178 | cyclopropyl | CF$_3$ | 4-Cl | H | H | H | N | H | H | H |
| 1-179 | cyclopropyl | CF$_2$H | 4-Cl | H | H | H | N | H | H | H |
| 1-180 | cyclopropyl | CH$_2$CH$_3$ | 2-CH$_3$ | 4-F | H | H | N | H | H | H |
| 1-181 | cyclopropyl | CH$_2$CH$_3$ | 2-CH$_3$ | 4-CN | H | H | N | H | H | H |
| 1-182 | cyclopropyl | CH$_2$CH$_3$ | 2-CH$_3$ | H | H | H | N | H | H | H |
| 1-183 | cyclopropyl | CH$_2$CH$_3$ | 2-CH$_3$ | 3-NH$_2$ | 4-F | H | N | H | H | H |
| 1-184 | cyclopropyl | CH$_2$CH$_3$ | 2-CH$_3$ | 5-F | H | H | N | H | H | H |
| 1-185 | cyclopropyl | CH$_2$CH$_3$ | 4-OCF$_3$ | H | H | H | N | H | H | H |
| 1-186 | cyclopropyl | CH$_2$CH$_3$ | 4-CF$_3$ | H | H | H | N | H | H | H |
| 1-187 | cyclopropyl | CH$_2$CH$_3$ | 2-F | 4-Cl | H | H | N | H | H | H |
| 1-188 | cyclopropyl | CH$_2$CH$_3$ | 2-CH$_3$ | 4-Cl | H | H | N | H | H | H |
| 1-189 | cyclopropyl | CH$_2$CH$_3$ | 2-CH$_3$ | 4-CF$_3$ | H | H | N | H | H | H |
| 1-190 | cyclopropyl | CH$_2$CH$_3$ | 4-CH$_2$-(1-pyrazolyl-3,5-bis-CF$_3$) | H | H | H | N | H | H | H |
| 1-191 | cyclopropyl | CH$_2$CH$_3$ | 2-CH$_3$ | 4-OCF$_3$ | H | H | N | H | H | H |
| 1-192 | cyclopropyl | CH$_2$CH$_3$ | 4-Cl | H | H | H | N | H | Cl | H |
| 1-193 | cyclopropyl | CH$_3$ | 4-OCF$_3$ | H | H | H | N | CF$_3$ | H | H |
| 1-194 | cyclopropyl | CHFCH$_3$ | 4-Cl | H | H | H | N | H | Cl | H |
| 1-195 | cyclopropyl | CH$_3$ | 4-Cl | H | H | H | N | CH$_3$ | H | CH$_3$ |
| 1-196 | cyclopropyl | CH$_2$CH$_3$ | 4-F | H | H | H | N | CF$_3$ | H | H |
| 1-197 | cyclopropyl | cyclopropyl | 4-Cl | H | H | H | N | H | Cl | H |
| 1-198 | cyclopropyl | cyclopropyl | 4-F | H | H | H | N | H | Cl | H |
| 1-199 | cyclopropyl | CH$_3$ | 4-Cl | H | H | H | N | CF$_3$ | H | H |
| 1-200 | cyclopropyl | CH$_2$CH$_3$ | 4-Cl | H | H | H | N | H | H | CF$_3$ |
| 1-201 | cyclopropyl | CH$_2$CH$_3$ | 4-F | H | H | H | N | H | H | CF$_3$ |
| 1-202 | cyclopropyl | CH$_2$CH$_3$ | 4-CN | H | H | H | N | H | H | CF$_3$ |
| 1-203 | cyclopropyl | CH$_2$CH$_3$ | 4-CF$_3$ | H | H | H | N | H | H | CF$_3$ |
| 1-204 | cyclopropyl | CH$_2$CH$_3$ | 4-OCF$_3$ | H | H | H | N | H | H | CF$_3$ |
| 1-205 | cyclopropyl | CH$_2$CH$_3$ | 2-F | 4-F | H | H | N | H | H | CF$_3$ |
| 1-206 | cyclopropyl | CH$_2$CH$_3$ | 2-Cl | 4-Cl | H | H | N | H | H | CF$_3$ |
| 1-207 | cyclopropyl | CH$_3$ | 4-Cl | H | H | H | N | H | H | CF$_3$ |
| 1-208 | cyclopropyl | CH$_3$ | 4-F | H | H | H | N | H | H | CF$_3$ |
| 1-209 | cyclopropyl | CH$_3$ | 4-CN | H | H | H | N | H | H | CF$_3$ |
| 1-210 | cyclopropyl | CH$_3$ | 4-CF$_3$ | H | H | H | N | H | H | CF$_3$ |
| 1-211 | cyclopropyl | CH$_3$ | 4-OCF$_3$ | H | H | H | N | H | H | CF$_3$ |
| 1-212 | cyclopropyl | CH$_3$ | 2-F | 4-F | H | H | N | H | H | CF$_3$ |
| 1-213 | cyclopropyl | CH$_3$ | 2-Cl | 4-Cl | H | H | N | H | H | CF$_3$ |
| 1-214 | cyclopropyl | cyclopropyl | 4-Cl | H | H | H | N | H | H | CF$_3$ |

TABLE 1-continued

Compounds of the formula    R⁵ = 

| Ex. No. | R¹ | R⁷ | G¹ | G² | G³ | R⁶ | A | G⁴ | G⁵ | G⁶ |
|---|---|---|---|---|---|---|---|---|---|---|
| 1-215 | cyclopropyl | cyclopropyl | 4-F | H | H | H | N | H | H | CF₃ |
| 1-216 | cyclopropyl | cyclopropyl | 4-CN | H | H | H | N | H | H | CF₃ |
| 1-217 | cyclopropyl | cyclopropyl | 4-CF₃ | H | H | H | N | H | H | CF₃ |
| 1-218 | cyclopropyl | cyclopropyl | 4-OCF₃ | H | H | H | N | H | H | CF₃ |
| 1-219 | cyclopropyl | cyclopropyl | 2-F | 4-F | H | H | N | H | H | CF₃ |
| 1-220 | cyclopropyl | cyclopropyl | 2-Cl | 4-Cl | H | H | N | H | H | CF₃ |
| 1-221 | CH(CH₃)₂ | CH₂CH₃ | 4-Cl | H | H | H | N | H | H | H |
| 1-222 |  | CH₂CH₃ | 2-F | 4-F | H | H | N | H | H | H |
| 1-223 | CH(CH₃)CH₂SCH₃ | CH₂CH₃ | 4-Cl | H | H | H | N | H | H | H |
| 1-224 | cyclobutyl | CH₂CH₃ | 4-F | H | H | H | N | H | H | H |
| 1-225 | cyclobutyl | CH₂CH₃ | 2-F | 4-F | H | H | N | H | H | H |
| 1-226 | cyclobutyl | CH₂CH₃ | 4-Cl | H | H | H | N | H | H | H |
| 1-227 | cyclopentyl | CH₂CH₃ | 4-F | H | H | H | N | H | H | H |
| 1-228 | cyclopentyl | CH₂CH₃ | 2-F | 4-F | H | H | N | H | H | H |
| 1-229 | 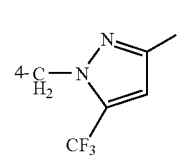 | CH₂CH₃ | 4-F | H | H | H | N | H | H | H |
| 1-230 | 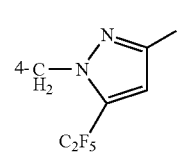 | CH₂CH₃ | 2-F | 4-Cl | H | H | N | H | H | H |
| 1-231 | cyclobutyl | CH₂CH₃ | 2-F | 4-Cl | H | H | N | H | H | H |
| 1-232 | cyclopropyl | CH₂CH₃ | 4-iC₃F₇ | H | H | H | N | H | H | H |
| 1-233 | cyclopropyl | cyclopropyl | 4-iC₃F₇ | H | H | H | N | H | H | H |
| 1-234 | cyclopropyl | cyclopropyl | H | H | H | H | N | H | H | H |
| 1-235 | cyclopropyl | cyclopropyl | 4-F | H | H | H | N | H | H | H |
| 1-236 | cyclopropyl | cyclopropyl | 4-Cl | H | H | H | N | H | H | H |
| 1-237 | cyclopropyl | propyl | H | H | H | H | N | H | H | H |
| 1-238 | cyclopropyl | propyl | 4-F | H | H | H | N | H | H | H |
| 1-239 | cyclopropyl | propyl | 4-Cl | H | H | H | N | H | H | H |
| 1-240 | cyclopropyl | cyclopropyl | 2-F | 4-F | H | H | N | H | H | H |
| 1-241 | cyclopropyl | C₂F₅ | 4-Cl | H | H | H | N | H | H | H |
| 1-242 | cyclopropyl | cyclopropyl | 4-CN | H | H | H | N | H | H | H |
| 1-243 | cyclopropyl | cyclopropyl | 4-OCF₃ | H | H | H | N | H | H | H |
| 1-244 | cyclopropyl | propyl | 2-Cl | 4-Cl | H | H | N | H | H | H |
| 1-245 | cyclopropyl | propyl | 2-F | 4-F | H | H | N | H | H | H |
| 1-246 | cyclopropyl | propyl | 4-CN | H | H | H | N | H | H | H |
| 1-247 | cyclopropyl | CH₂CH₃ | 4-CH₂-pyrazole(N-CF₃, C₂F₅) | H | H | H | N | H | H | H |
| 1-248 | cyclopropyl | CH₂CH₃ | 4-CH₂-pyrazole(N-C₂F₅, C₂F₅) | H | H | H | N | H | H | H |

TABLE 1-continued

Compounds of the formula

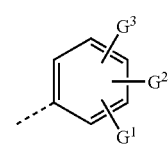

| Ex. No. | R¹ | R⁷ | G¹ | G² | G³ | R⁶ | A | G⁴ | G⁵ | G⁶ |
|---|---|---|---|---|---|---|---|---|---|---|
| 1-249 | cyclopropyl | $C_3F_7$ | 4-Cl | H | H | H | N | H | H | H |
| 1-250 | (cyclopropyl, R-substituted) | $CH_2CH_3$ | 4-Cl | H | H | H | N | H | H | H |
| 1-251 | cyclopropyl | $C_3F_7$ | 4-F | H | H | H | N | H | H | H |
| 1-252 | cyclopropyl | cyclopropyl | 4-CH₂-(3,5-bis(CF₃)pyrazol-1-yl) | H | H | H | N | H | H | H |
| 1-253 | cyclopropyl | cyclopropyl | 4-CH₂-(3-$C_2F_5$-5-$CF_3$-pyrazol-1-yl) | H | H | H | N | H | H | H |
| 1-254 | cyclopropyl | $CH_2CF_3$ | 2-F | 4-F | H | H | N | H | H | H |
| 1-255 | cyclopropyl | $CH_2CH_3$ | 4-F | H | H | H | CH | H | H | H |
| 1-256 | cyclopropyl | $CH_2CH_3$ | 4-Cl | H | H | H | CH | H | H | H |
| 1-257 | cyclopropyl | $CH_2CH_3$ | 4-$OCF_3$ | H | H | H | CH | H | H | H |
| 1-258 | cyclopropyl | $CH_2CH_3$ | 4-CH₂-(3,5-bis(CF₃)-1,2,4-triazol-1-yl) | H | H | H | N | H | H | H |
| 1-259 | cyclopropyl | cyclopropyl | 4-CH₂-(3,5-bis(CF₃)-1,2,4-triazol-1-yl) | H | H | H | N | H | H | H |
| 1-260 | cyclopropyl | $C_2F_5$ | 2-F | 4-F | H | H | N | H | H | H |
| 1-261 | cyclopropyl | $C_2F_5$ | 4-F | H | H | H | N | H | H | H |
| 1-262 | cyclopropyl | C(=O)NHCH(CH2)2 | 4-F | H | H | H | N | H | H | H |
| 1-263 | cyclopropyl | Cl | 4-Cl | H | H | H | CH | H | H | F |
| 1-264 | cyclopropyl | $CH_2CH_2CH_3$ | 4-CH₂-(3,5-bis(CF₃)-1,2,4-triazol-1-yl) | H | H | H | N | H | H | H |

TABLE 1-continued

Compounds of the formula (structure shown with substituents R¹, R⁵, R⁶, R⁷, G⁴, G⁵, G⁶, A)

R⁵ = phenyl with G¹, G², G³ substituents

| Ex. No. | R¹ | R⁷ | G¹ | G² | G³ | R⁶ | A | G⁴ | G⁵ | G⁶ |
|---|---|---|---|---|---|---|---|---|---|---|
| 1-265 | cyclopropyl | CH₂CH₃ | 4-CH₂-[1,2,4-triazol-1-yl, 3-CF₃, 5-CF₃] | H | H | H | CH | H | H | H |
| 1-266 | cyclopropyl | CH₂CH₃ | 4-CH₂-[pyrazol-1-yl, 3-C₂F₅] | H | H | H | N | H | H | H |
| 1-267 | cyclopropyl | CH₂CH₃ | 4-CH₂-[pyrazol-1-yl, 3-C₃F₇] | H | H | H | N | H | H | H |
| 1-268 | cyclopropyl | CH₂CH₃ | 4-CH₂-[1,2,4-triazol-1-yl, 3-CF₃, 5-CF₃] | H | H | H | N | H | H | H |
| 1-269 | cyclopropyl | CH₂CH₃ | 4-CH₂-[pyrazol-1-yl, 3-C₂F₅, 5-C₂F₅] | H | H | H | N | H | H | H |
| 1-270 | cyclopropyl | CH₂CH₃ | 2-F | 4-F | H | SCH₃ | N | H | H | H |
| 1-271 | cyclopropyl | OCF₃ | 2-F | 4-F | H | H | N | H | H | H |
| 1-272 | cyclopropyl | CH₂CH₃ | 4-CH₂-[1,2,4-triazol-1-yl, 3-CF₃, 5-CF₃] | H | H | H | N | H | H | H |
| 1-273 | cyclopropyl | CH₂CH₃ | 4-CH₂-[1,2,4-triazol-1-yl, 3-CF₃] | H | H | H | N | H | H | H |
| 1-274 | CH(CF₃)CH₃ | CH₂CH₃ | 2-F | 4-F | H | H | N | H | H | H |
| 1-275 | cyclopropyl | CH₂CH₃ | H | H | H | CH₃ | N | H | H | H |
| 1-276 | cyclopropyl | CH₂CH₃ | 4-F | H | H | CH₃ | N | H | H | H |
| 1-277 | cyclopropyl | CH₂CH₃ | 2-Cl | 4-Cl | H | CH₃ | N | H | H | H |
| 1-278 | cyclopropyl | CH₂CH₃ | 2-F | 4-F | H | CH₃ | N | H | H | H |
| 1-279 | cyclopropyl | CH₂CH₃ | 4-OCF₃ | H | H | CH₃ | N | H | H | H |
| 1-280 | cyclopropyl | CH₂CH₃ | H | H | H | CH₃ | CH | H | H | H |
| 1-281 | cyclopropyl | CH₂CH₃ | 4-F | H | H | CH₃ | N | H | H | H |
| 1-282 | cyclopropyl | CH₂CH₃ | 4-Cl | H | H | CH₃ | N | H | H | H |
| 1-283 | cyclopropyl | CH₂CH₃ | 2-Cl | 4-Cl | H | CH₃ | N | H | H | H |
| 1-284 | cyclopropyl | CH₂CH₃ | 2-Cl | 4-Cl | H | CH₃ | N | H | H | H |
| 1-285 | cyclopropyl | CH₂CH₃ | 2-Cl | 4-Cl | H | CH₃ | N | H | H | H |

TABLE 1-continued

Compounds of the formula 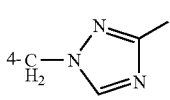  R⁵ = 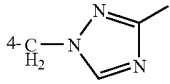

| Ex. No. | R¹ | R⁷ | G¹ | G² | G³ | R⁶ | A | G⁴ | G⁵ | G⁶ |
|---|---|---|---|---|---|---|---|---|---|---|
| 1-286 | cyclopropyl | CH₂CH₃ | 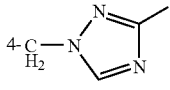 | H | H | H | CH | H | H | H |
| 1-287 | cyclopropyl | cyclopropyl | 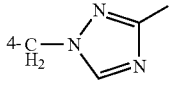 | H | H | H | N | H | H | H |
| 1-288 | cyclopropyl | CH₂CH₃ | 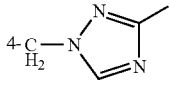 | H | H | H | N | H | H | H |
| 1-289 | cyclopropyl | CH₂CH₃ | 4-CN | H | H | CH₃ | N | H | H | H |
| 1-290 | cyclopropyl | CH₂CH₃ | 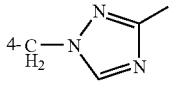 | H | H | SCH₃ | N | H | H | H |
| 1-291 | cyclopropyl | CH₂CH₃ | | H | H | H | CH | H | H | H |
| 1-292 | cyclopropyl | cyclopropyl | | H | H | H | N | H | H | H |
| 1-293 | cyclopropyl | CH₂CH₃ | 4-CN | H | H | H | CH | H | H | H |
| 1-294 | CH(CH₃)₂ | CH₂CH₃ | 2-F | 4-F | H | H | CH | H | H | H |
| 1-295 | cyclopropyl | CH₂CH₃ | 2-F | 4-F | H | H | CH | H | H | H |
| 1-296 | cyclopropyl | CH₂CH₃ | H | H | H | H | CH | H | H | H |
| 1-297 | CH(CH₃)₂ | CH₂CH₃ | 4-OCF₃ | H | H | H | CH | H | H | H |
| 1-298 | cyclopropyl | CH₂CH₃ | 2-Cl | 4-Cl | H | H | CH | H | H | H |
| 1-299 | CH(CF₃)CH₃ | CH₂CH₃ | 4-F | H | H | H | N | H | H | H |
| 1-300 | cyclopropyl | CH₂CH₃ | 2-Cl | 4-Cl | H | CH₃ | CH | H | H | H |
| 1-301 | cyclopropyl | CH₂CH₃ | 4-Cl | H | H | CH₃ | N | H | H | H |
| 1-302 | cyclopropyl | CF₃ | 4-Cl | H | H | CH₃ | CH | Cl | H | H |
| 1-303 | cyclopropyl | CH₃ | 4-F | H | H | CH₃ | CH | Cl | H | H |
| 1-304 | cyclopropyl | CH₃ | 4-Cl | H | H | CH₃ | CH | Cl | H | H |
| 1-305 | cyclopropyl | CH₂CH₃ | 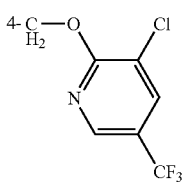 | H | H | H | N | H | H | H |

TABLE 1-continued

Compounds of the formula 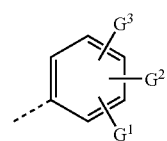

| Ex. No. | $R^1$ | $R^7$ | $G^1$ | $G^2$ | $G^3$ | $R^6$ | A | $G^4$ | $G^5$ | $G^6$ |
|---|---|---|---|---|---|---|---|---|---|---|
| 1-306 | cyclopropyl | $CH_2CH_3$ | 4-$CH_2$-O-(3-Cl-5-CF$_3$-pyridin-2-yl) | H | H | H | N | H | H | H |
| 1-307 | cyclopropyl | $CH_2CF_3$ | 4-F | H | H | H | N | H | H | H |
| 1-308 | cyclopropyl | $CHFCF_3$ | 4-F | H | H | H | N | H | H | H |
| 1-309 | cyclopropyl | $CH_2CH_3$ | 4-$CH_2$-O-(5-CF$_3$-pyridin-2-yl) | H | H | H | N | H | H | H |
| 1-310 | cyclopropyl | $CH_2CH_3$ | 4-O-(3-Cl-5-CF$_3$-pyridin-2-yl) | H | H | H | N | H | H | H |
| 1-311 | cyclopropyl | $CH_2CH_3$ | 4-O-(3-CF$_3$-pyridin-2-yl) | H | H | H | N | H | H | H |
| 1-312 | cyclopropyl | $CH_2CH_3$ | 4-O-(6-CF$_3$-pyridin-2-yl) | H | H | H | N | H | H | H |
| 1-313 | cyclopropyl | $CH_2CH_3$ | 4-F | H | H | $CF_3$ | N | H | H | H |
| 1-314 | cyclopropyl | $CH_2CH_3$ | 2-F | 4-F | H | $CF_3$ | N | H | H | H |
| 1-315 | cyclopropyl | $CH_2CH_3$ | 4-F | H | H | H | N | H | H | Cl |
| 1-316 | cyclopropyl | $CH_2CH_3$ | 4-Cl | H | H | H | N | H | H | Cl |
| 1-317 | cyclopropyl | $CH_2CH_3$ | 4-O-(4-CF$_2$CF$_3$-6-CF$_3$-pyrimidin-2-yl) | H | H | H | N | H | H | H |

TABLE 1-continued

Compounds of the formula (structure shown with substituents R¹, R⁶, R⁵, R⁷, G¹-G⁶, A)

| Ex. No. | R¹ | R⁷ | G¹ | G² | G³ | R⁶ | A | G⁴ | G⁵ | G⁶ |
|---|---|---|---|---|---|---|---|---|---|---|
| 1-318 | cyclopropyl | CH₂CH₃ | 4-CH₂-(1-methyl-3-heptafluoropropyl-1,2,4-triazol-5-yl) | H | H | H | N | H | H | H |
| 1-319 | cyclopropyl | CH₂CH₃ | 4-CH₂-(3-heptafluoropropyl-1,2,4-triazol-5-yl) | H | H | H | N | H | H | H |
| 1-320 | cyclopropyl | CH₂CH₃ | 4-F | H | H | H | CH | H | H | CH₃ |
| 1-321 | cyclopropyl | CH₂CH₃ | 4-CN | H | H | H | CH | H | H | Cl |
| 1-322 | cyclopropyl | CH₂CH₃ | 4-F | H | H | H | N | H | F | H |
| 1-323 | cyclopropyl | CH₂CH₃ | 4-F | H | H | H | N | H | Cl | H |
| 1-324 | cyclopropyl | CH₂CF₃ | 4-F | H | H | CF₃ | N | H | H | H |
| 1-325 | cyclopropyl | CH₂CF₃ | 4-F | H | H | Cl | N | H | H | H |
| 1-326 | cyclopropyl | CH₂CH₃ | 4-F | H | H | Cl | N | H | H | H |
| 1-327 | cyclopropyl | CH₃ | 4-Cl | H | H | H | C—Cl | H | H | CH₃ |
| 1-328 | cyclopropyl | CH₃ | 4-F | H | H | H | C—Cl | H | H | CH₃ |
| 1-329 | cyclopropyl | CH₃ | 4-F | H | H | H | CH | Br | H | CH₃ |
| 1-330 | cyclopropyl | CH₃ | 4-Cl | H | H | H | CH | H | Cl | CH₃ |
| 1-331 | cyclopropyl | CH₂CH₃ | 4-Cl | H | H | H | C—CN | H | H | H |
| 1-332 | cyclopropyl | CH₂CH₃ | 2-F | 4-F | H | H | C—CN | H | H | H |

TABLE 2

Physicochemical characterization

| Ex. No. | MH+ | logP (HCOOH) | NMR (400 MHz, DMSO-d6, unless indicated otherwise) |
|---|---|---|---|
| 1-1 | 364.2 | 0.71 | (MeOH d4); 0.68 (2H, m), 0.90 (2H, m), 2.38 (3H, s), 2.94 (1H, m), 7.22 (2H, t), 7.35 (1H, m), 7.61 (2H, m), 7.95 (1H, m), 8.49 (1H, m), 8.59 (1H, s). |
| 1-2 | 538.1 | 2.31 | |
| 1-3 | 538.1 | 2.27 | |
| 1-4 | 396.2 | 1.34 | |
| 1-5 | 396.0 | | 0.56 (2H, m), 0.78 (2H, m), 1.06 (3H, t), 2.90 (1H, m), 6.88 (1H, s), 7.11 (1H, m), 7.22 (2H, m), 7.50 (1H, m), 7.74 (1H, m), 8.52 (2H, m), 9.36 (1H, s). |
| 1-8 | 374.2 | | |
| 1-9 | 396.1 | | |
| 1-10 | 406.1 | | |
| 1-11 | 378.1 | | |
| 1-12 | 404.1 | | |
| 1-13 | 394.1 | | |
| 1-14 | 361.1 | | (MeCN d3); 0.56 (2H, m), 0.80 (2H, m), 1.13 (3H, t), 2.67 (2H, q), 2.89 (1H, m), 6.12 (1H, m), 7.22 (1H, m), 7.41 (1H, m), 7.69 (1H, m), 7.97 (1H, m), 8.08 (1H, s), 8.58 (3H, m), 8.81 (1H, m). |
| 1-72 | 429.2 | 2.35 | |

TABLE 2-continued

Physicochemical characterization

| Ex. No. | MH+ | logP (HCOOH) | NMR (400 MHz, DMSO-d6, unless indicated otherwise) |
|---|---|---|---|
| 1-73 | 430.0 | 1.45 | 0.60 (m, 2H), 0.78 (m, 2H), 2.24 (s, 3H), 2.91 (m, 1H), 7.29 (m, 1H), 7.39 (d, 2H), 7.76 (d, 2H), 7.95 (d, 2H), 8.49 (m, 1H), 8.56 (m, 1H), 9.56 (s, 1H). |
| 1-74 | 432.1 | 1.55 | 1.26 (d, 6H), 2.36 (s, 3H), 4.41 (m, 1H), 5.75 (m, 1H), 7.31 (m, 1H), 7.40 (m, 2H), 7.78 (m, 2H), 7.99 (m, 1H), 8.01 (m, 1H), 8.49 (m, 1H). |
| 1-75 | 450.1 | 1.99 | 0.78 (m, 2H), 0.89 (m, 2H), 3.15 (m, 1H), 7.34 (m, 3H), 7.76 (m, 2H), 7.95 (m, 1H), 8.40 (m, 1H), 8.60 (m, 1H), 9.42 (m, 1H). |
| 1-76 | 452.1 | 2.05 | 1.27 (d, 6H), 4.40 (m, 1H), 7.13 (m, 1H), 7.48 (m, 3H), 7.77 (m, 2H), 7.90 (m, 1H), 8.48 (m, 1H), 8.64 (m, 1H), 10.02 (m, 1H). |
| 1-78 | 451.1 | 2.55 | 1.20 (d, 6H), 4.38 (m, 1H), 6.85 (m, 1H), 7.28 (d, 2H), 7.53 (d, 2H), 7.73 (d, 2H), 7.84 (d, 2H), 8.48 (s, 1H), 9.56 (s, 1H). |
| 1-80 | 433.1 | 2.33 | 0.61 (m, 2H), 0.77 (m, 2H), 2.93 (m, 1H), 6.66 (m, 1H), 7.40 (m, 2H), 7.46 (m, 2H), 7.78 (m, 2H), 7.84 (m, 2H), 8.54 (s, 1H), 9.60 (s, 1H). |
| 1-81 | 413.1 | 2.33 | 0.58 (m, 2H), 0.77 (m, 2H), 2.07 (s, 3H), 2.91 (m, 1H), 6.97 (m, 1H), 7.22 (m, 2H), 7.48 (m, 2H), 7.73 (m, 2H), 7.83 (m, 2H), 8.55 (s, 1H), 9.24 (s, 1H). |
| 1-82 | 434.0 | 1.94 | 0.54 (m, 2H), 0.80 (m, 2H), 2.91 (m, 1H), 6.81 (m, 1H), 7.50 (m, 1H), 7.78 (d, 2H), 7.99 (d, 1H), 8.06 (m, 1H), 8.46 (m, 1H), 8.56 (m, 1H), 8.57 (m, 1H), 9.72 (s, 1H). |
| 1-83 | 414.1 | 1.43 | 0.58 (m, 2H), 0.77 (m, 2H), 2.21 (s, 3H), 2.90 (m, 1H), 7.14 (m, 1H), 7.28 (m, 1H), 7.76 (d, 2H), 7.84 (d, 2H), 8.11 (m, 1H), 8.47 (m, 1H), 8.54 (m, 1H), 9.45 (s, 1H). |
| 1-84 | 468.1 | 2.19 | |
| 1-85 | 442.1 | 2.02 | 0.57 (m, 2H), 0.78 (m, 2H), 1.01 (d, 6H), 2.89 (m, 1H), 7.05 (m, 1H), 7.23 (m, 1H), 7.76 (d, 2H), 7.83 (d, 2H), 7.85 (d, 2H), 8.54 (s, 1H), 9.70 (s, 1H). |
| 1-86 | 427.1 | 2.68 | 0.55 (m, 2H), 0.78 (m, 2H), 0.91 (t, 3H), 2.38 (q, 2H), 2.91 (m, 1H), 6.85 (m, 1H), 7.24 (m, 1H), 7.36 (m, 1H), 7.45 (m, 1H), 7.76 (m, 3H), 7.84 (m, 2H), 8.55 (m, 1H), 9.28 (s, 1H). |
| 1-87 | 428.2 | 1.27 | |
| 1-88 | 447.0 | 1.93 | 0.53 (m, 2H), 0.73 (m, 2H), 2.34 (s, 3H), 2.94 (m, 1H), 6.43 (m, 1H), 7.44 (m, 4H), 7.72 (m, 4H), 9.51 (s, 1H). |
| 1-89 | 455.1 | 1.72 | 0.62 (m, 2H), 0.78 (m, 2H), 1.07 (m, 2H), 1.15 (m, 2H), 1.25 (m, 2H), 2.21 (s, 3H), 2.95 (m, 1H), 7.33 (m, 1H), 7.80 (m, 5H), 7.86 (m, 1H), 8.49 (m, 1H), 9.70 (s, 1H). |
| 1-99 | 478.0 | 2.44 | 0.31 (m, 1H), 0.36 (m, 1H), 0.45 (, 1H), 0.50 (m, 1H), 1.00 (m, 1H), 1.20 (d, 3H), 3.76 (m, 1H), 5.81 (m, 1H), 7.39 (m, 3H), 7.70 (m, 3H), 8.24 (s, 1H), 8.45 (s, 2H). |
| 1-100 | 458.1 | 1.80 | 0.31 (m, 1H), 0.36 (m, 1H), 0.45 (m, 1H), 0.50 (m, 1H), 1.10 (m, 1H), 1.28 (d, 3H), 3.80 (m, 1H), 6.59 (m, 1H), 7.30 (m, 2H), 7.41 (m, 2H), 7.79 (m, 2H), 8.44 (s, 1H), 8.50 (s, 1H), 9.49 (s, 1H). |
| 1-111 | 504.1 | 2.65 | 0.36 (m, 4H), 0.50 (m, 4H), 1.11 (m, 2H), 3.56 (m, 1H), 6.21 (m, 1H), 7.44 (m, 2H), 7.53 (m, 2H), 7.79 (m, 2H), 8.42 (s, 1H), 8.50 (s, 1H), 9.91 (s, 1H). |
| 1-112 | 415.2 | 2.12 | |
| 1-113 | 449.0 | 2.41 | 0.55 (m, 2H), 0.88 (m, 2H), 2.96 (m, 1H), 5.87 (m, 1H), 7.33 (m, 3H), 7.45 (m, 3H), 7.70 (m, 1H), 7.62 (m, 1H), 7.98 (m, 1H), 8.40 (m, 1H), 8.56 (m, 1H) |
| 1-114 | 460 | 1.4 | 0.56 (2H, m), 0.78 (2H, m), 1.04 (3H, t), 2.91 (1H, m), 7.00 (1H, m), 7.26 (1H, m), 7.74 (4H, m), 7.85 (1H, 9), 8.54 (2H, m), 9.42 (1H, s). |
| 1-115 | 419 | 1.40 | 0.55 (2H, m), 0.77 (2H, m), 1.04 (3H, t), 2.55 (2H, q), 2.89 (1H, m), 6.74 (1H, d), 6.96 (1H, m), 7.28 (1H, m), 7.92 (2H, m), 8.44 (1H, m), 8.55 (2H, m), 9.41 (1H, s). |
| 1-116 | 446 | 1.81 | 0.58 (2H, m), 0.79 (2H, m), 2.23 (3H, s), 2.90 (1H, m), 7.10 (1H, s), 7.25 (1H, m), 7.75 (4H, m), 7.85 (1H, m), 8.48 (1H, m), 8.54 (1H, s), 9.41 (1H, s). |
| 1-117 | 477 | 1.65 | |
| 1-119 | 485 | 1.80 | 0.55 (2H, m), 0.76 (2H, m), 2.32 (3H, s), 2.88 (1H, m), 5.13 (2H, s), 6.87 (1H, m), 7.01 (2H, d), 7.25 (1H, m), 7.42 (4H, m), 7.64 (2H, d), 7.88 (1H, m), 8.49 (1H, m), 9.34 (1H, s). |
| 1-120 | 444 | 1.52 | |
| 1-121 | 467 | 1.15 | |
| 1-122 | 450 | 1.95 | 0.58 (2H, m), 0.78 (2H, m), 2.91 (1H, m), 7.33 (2H, m), 7.61 (2H, m), 7.95 (1H, m), 8.52 (1H, m), 8.57 (1H, s), 9.41 (1H, s). |
| 1-123 | 512 | 1.79 | 0.58 (2H, m), 0.77 (2H, m), 2.25 (3H, s), 6.33 (1H, m), 7.04 (1H, m), 7.29 (3H, m), 7.74 (2H, m), 7.90 (1H, m), 8.48 (1H, m), 8.83 (1H, s), 9.39 (1H, s). |
| 1-124 | 378 | 1.03 | |
| 1-126 | 329 | 1.60 | 0.57 (2H, m), 0.79 (2H, m), 1.03 (3H, t), 2.91 (1H, m), 6.86 (1H, m), 7.263 (1H, m), 7.44 (2H, m), 7.61 (1H, m), 7.72 (1H, m), 8.50 (2H, m), 9.33 (1H, s). |
| 1-127 | 360 | 1.01 | 0.55 (2H, m), 0.76 (2H, m), 1.06 (3H, t), 2.55 (2H, q), 2.89 (1H, m), 6.86 (1H, m), 7.25 (1H, m), 7.37 (3H, m), 7.62 (2H, m), 7.84 (1H, m), 8.52 (2H, m), 9.38 (1H, s). |
| 1-128 | 332 | 0.63 | 0.56 (2H, m), 0.73 (2H, m), 2.86 (1H, m), 7.17 (1H, s), 7.30 (3H, m), 7.46 (1H, m), 7.62 (2H, m), 8.10 (1H, m), 8.52 (1H, s), 8.67 (1H, m), 8.96 (1H, m), 9.65 (1H, s). |
| 1-129 | 384 | 1.27 | 0.54 (2H, m), 0.79 (2H, m), 2.90 (1H, m), 6.64 (1H, m), 7.23 (1H, m), 7.51 (1H, m), 7.70 (2H, m), 7.94 (1H, m), 8.47 (1H, m), 8.53 (1H, s), 9.69 (1H, s). |
| 1-130 | 401 | 1.55 | 0.61 (2H, m), 0.85 (2H, m), 3.00 (1H, m), 7.47 (1H, m), 7.53 (1H, m), 7.69 (1H, m), 8.02 (1H, m), 8.48 (1H, m), 8.65 (1H, s). |
| 1-133 | 385.2 | 1.10 | 0.56 (2H, m), 0.78 (2H, m), 1.04 (3H, t), 2.89 (1H, m), 7.07 (1H, m), 7.27 (1H, m), 7.84 (6H, m), 8.55 (2H, m), 9.40 (1H, s). |
| 1-134 | 394.2 | 1.53 | 1.34 (3H, t), 1.48 (9H, s), 2.67 (2H, q), 5.78 (1H, s), 7.29 (3H, m), 7.60 (1H, m), 7.68 (2H, m), 8.48 (1H, s), 8.56 (1H, m), 9.61 (1H, s). |
| 1-135 | 410.1 | 1.86 | 1.31 (3H, t), 1.48 (9H, s), 2.65 (1H, s), 5.81 (1H, s), 7.30 (1H, m), 7.50 (2H, m), 7.64 (3H, m), 8.48 (1H, s), 8.55 (1H, m), 9.61 (1H, s). |
| 1-136 | 401.2 | 1.81 | 1.11 (3H, t), 1.48 (9H, s), 2.61 (2H, q), 5.93 (1H, s), 7.30 (1H, m), 7.61 (1H, m), 7.81 (2H, d), 7.88 (1H, d), 8.51 (1H, s), 8.55 (1H, m), 9.64 (1H, s). |
| 1-137 | 444.2 | 2.34 | 1.08 (3H, t), 1.49 (9H, s), 2.57 (2H, q), 5.88 (1H, s), 7.30 (1H, m), 7.61 (1H, m), 7.82 (4H, m), 8.51 (1H, s), 8.54 (1H, s), 9.65 (1H, s). |
| 1-138 | 460.2 | 2.32 | 1.11 (2H, q), 1.48 (9H, s), 2.63 (2H, q), 5.82 (1H, s), 7.29 (1H, m), 7.39 (2H, m), 7.58 (1H, m), 7.75 (2H, m), 8.49 (1H, s), 8.55 (1H, m), 9.63 (1H, s). |
| 1-139 | 412.1 | 0.79 | 0.56 (2H, m), 0.78 (2H, m), 1.04 (3H, t), 2.90 (1H, m), 6.82 (1H, m), 7.23 (1H, m), 7.44 (2H, m), 7.67 (2H, m), 8.50 (2H, m), 9.30 (1H, m). |
| 1-140 | 394.1 | 1.07 | 1.19 (2H, m) 0.78 (2H, m), 1.03 (3H, t), 2.91 (1H, m), 6.80 (1H, m), 7.37 (1H, m), 7.37 (3H, m), 7.49 (1H, m), 7.48 (1H, m), 8.53 (1H, m), 9.28 (1H, m). |
| 1-141 | 395.2 | 1.65 | 1.12 (3H, t), 1.48 (9H, s), 2.66 (2H, q), 5.97 (1H, s), 7.24 (1H, m), 7.30 (1H, m), 7.62 (1H, m), 8.20 (1H, m), 8.50 (2H, m), 8.55 (1H, m), 9.64 (1H, s). |

TABLE 2-continued

Physicochemical characterization

| Ex. No. | MH+ | logP (HCOOH) | NMR (400 MHz, DMSO-d6, unless indicated otherwise) |
|---|---|---|---|
| 1-142 | 444.1 | 1.89 | 1.08 (3H, t), 1.48 (9H, m), 5.84 (1H, s), 7.26 (1H, m), 7.42 (3H, m), 7.64 (1H, m), 8.48 (1H, s), 8.52 (1H, m), 9.56 (1H, s). |
| 1-143 | 406.2 | 1.47 | 0.41 (4H, m), 1.03 (1H, m), 1.12 (3H, t), 1.25 (3H, d), 2.67 (2H, q), 3.79 (1H, m), 6.40 (1H, d), 7.23 (2H, t), 7.29 (2H, m), 7.72 (3H, m), 8.42 (1H, s), 8.55 (1H, m), 9.48 (1H, s). |
| 1-144 | 422.1 | 1.62 | 0.45 (4H, m), 1.05 (1H, m), 1.13 (3H, t), 1.24 (3H, d), 2.65 (2H, q), 3.77 (1H, m), 6.43 (1H, d), 7.30 (1H, m), 7.48 (2H, d), 7.67 (2H, d), 7.76 (1H, d), 8.42 (1H, s), 8.56 (1H, d), 9.49 (1H, s). |
| 1-145 | 413.2 | 1.67 | 0.40 (4H, m), 1.10 (4H, m), 1.24 (3H, d), 2.61 (2H, q), 3.79 (1H, m), 6.59 (1H, d), 7.31 (1H, m), 7.76 (1H, m), 7.84 (4H, m), 8.45 (1H, s), 8.56 (1H, m), 9.51 (1H, s). |
| 1-146 | 472.2 | 2.18 | 0.47 (4H, m) 1.09 (3H, t), 1.26 (3H, d), 2.62 (2H, q), 3.79 (1H, m), 6.45 (1H, d), 7.29 (1H, m), 7.40 (2H, d), 7.76 (3H, m), 8.43 (1H, s), 8.55 (1H, m), 9.51 (1H, s). |
| 1-147 | 441.1 | 1.95 | 1.13 (4H, m), 1.35 (3H, d), 2.71 (2H, q), 4.25 (1H, m), 6.26 (1H, d), 7.26 (3H, m), 7.63 (1H, m), 7.72 (2H, m), 8.48 (1H, s), 8.55 (1H, m), 9.68 (1H, s). |
| 1-148 | 490.1 | 2.67 | 1.09 (4H, m), 1.37 (2H, d), 2.59 (1H, m), 4.22 (1H, m), 6.25 (1H, d), 7.27 (1H, m), 7.44 (1H, m), 7.50 (2H, m), 7.66 (1H, m), 8.50 (1H, s), 8.54 (1H, m), 9.67 (1H, s). |
| 1-149 | 458.1 | 2.26 | 1.16 (4H, m); 1.35 (3H, d), 2.70 (2H, q), 4.25 (1H, m) 6.30 (1H, m), 7.32 (1H, m), 7.51 (2H, d), 7.68 (3H, m), 8.49 (1H, s), 8.56 (1H, m), 9.69 (1H, s). |
| 1-150 | 449.1 | 2.08 | 1.19 (4H, m), 1.35 (3H, d), 2.66 (1H, m), 4.3 (1H, m), 6.43 (1H, d), 7.32 (1H, m), 7.69 (4H, m), 8.52 (1H, s), 8.57 (1H, m), 9.71 (1H, s). |
| 1-151 | 436.2 | 2.22 | 0.41 (6H, m), 1.13 (3H, t), 1.37 (4H, m), 1.50 (1H, m), 2.69 (2H, q), 5.73 (1H, s), 7.30 (1H, m), 7.50 (2H, s), 7.57 (1H, d), 7.63 (2H, d), 8.47 (1H, s), 8.55 (1H, m), 9.73 (1H, s). |
| 1-152 | 386.2 | 1.32 | |
| 1-154 | 396.1 | 1.83 | 0.54 (2H, m), 0.75 (2H, m), 2.87 (1H, m), 3.99 (3H, s), 6.86 (1H, s), 7.10 (1H, m), 7.42 (2H, d), 7.70 (2H, d), 8.01 (1H, m), 8.30 (1H, m), 8.52 (1H, s), 9.37 (1H, s). |
| 1-155 | 360.2 | 1.49 | 0.54 (2H, m); 0.75 (2H, m), 2.88 (1H, m), 3.99 (3H, s), 6.81 (1H, s), 7.14 (1H, m), 7.16 (2H, t), 7.74 (2H, m), 8.00 (1H, m), 8.29 (1H, m), 8.51 (1H, s), 9.37 (1H, s). |
| 1-156 | 387.3 | 1.59 | 0.55 (2H, m), 0.75 (2H, m), 2.87 (1H, m), 3.99 (3H, s), 6.96 (1H, m), 7.09 (1H, m), 7.81 (4H, m), 7.99 (1H, m), 8.29 (1H, m), 8.55 (1H, s), 9.38 (1H, s). |
| 1-157 | 446.1 | 2.21 | 0.54 (2H, m), 0.75 (2H, m), 2.88 (1H, m), 3.97 (3H, s), 6.86 (1H, s), 7.08 (1H, m), 7.33 (2H, m), 7.79 (2H, m), 7.99 (1H, m), 8.28 (1H, m), 8.53 (1H, s), 9.38 (1H, s). |
| 1-158 | 410.0 | 2.54 | 0.53 (2H, m), 0.75 (2H, m), 1.31 (3H, t), 2.87 (1H, m), 4.47 (2H, q), 6.83 (1H, s), 7.09 (1H, m), 7.40 (2H, d), 7.69 (2H, d), 8.03 (1H, m), 8.28 (1H, m), 8.52 (1H, s), 9.28 (1H, s). |
| 1-159 | 394.2 | 1.84 | 0.53 (2H, m), 0.74 (2H, m), 1.30 (3H, t), 2.86 (1H, m), 4.49 (2H, q), 6.79 (1H, m), 7.07 (1H, m), 7.16 (2H, t), 7.72 (2H, m), 8.01 (1H, m), 8.28 (1H, m), 8.51 (1H, m), 9.29 (1H, s). |
| 1-160 | 401.2 | 1.80 | 0.54 (2H, m), 0.77 (2H, m), 1.31 (3H, t), 2.89 (1H, m), 4.49 (2H, q), 6.95 (1H, s), 7.07 (1H, m), 7.81 (4H, m), 8.01 (1H, m), 8.23 (1H, m), 8.55 (1H, s), 9.30 (1H, s). |
| 1-161 | 460.1 | 2.64 | 0.53 (2H, m), 0.75 (2H, m), 1.27 (3H, t), 2.88 (1H, m), 4.45 (2H, q), 6.83 (1H, s), 7.07 (1H, m), 7.33 (2H, m), 7.77 (2H, m), 8.03 (1H, m), 8.27 (1H, m), 8.53 (1H, s), 9.30 (1H, s). |
| 1-162 | 424.1 | 2.31 | 0.53 (2H, m), 0.75 (2H, m), 1.28 (6H, d), 2.86 (1H, m), 5.40 (1H, m), 6.82 (1H, m), 7.08 (1H, m), 7.42 (2H, d), 7.63 (2H, d), 8.06 (1H, m), 8.28 (1H, m), 8.52 (1H, s), 9.15 (1H, s). |
| 1-163 | 408.2 | 2.19 | 0.54 (2H, m), 0.76 (2H, m), 1.28 (6H, d), 2.86 (1H, m), 5.40 (1H, m), 6.78 (1H, s), 7.06 (1H, m), 7.17 (2H, t), 7.67 (2H, m), 8.06 (1H, m), 8.28 (1H, m), 8.52 (1H, s) 9.16 (1H, s). |
| 1-164 | 415.1 | 2.27 | 0.55 (2H, m), 0.75 (2H, m), 1.27 (6H, d), 2.87 (1H, m), 5.40 (1H, m), 6.93 (1H, m), 7.06 (1H, m), 7.80 (4H, m), 8.02 (1H, m), 8.27 (1H, m), 8.55 (1H, s), 9.16 (1H, s). |
| 1-165 | 474.1 | 2.32 | 0.54 (2H, m), 0.75 (2H, m), 1.24 (6H, d), 2.86 (1H, m), 5.39 (1H, m), 6.82 (1H, m), 7.07 (1H, m), 7.34 (2H, m), 7.73 (2H, m), 8.05 (1H, m), 8.28 (1H, m), 8.53 (1H, s), 9.18 (1H, s). |
| 1-166 | 464.1 | 2.48 | 0.52 (2H, m), 0.76 (2H, m), 2.86 (1H, m), 5.10 (2H, q), 6.78 (1H, s), 7.22 (1H, m), 7.38 (2H, m), 7.70 (2H, d), 8.04 (1H, m), 8.32 (1H, m), 8.53 (1H, s), 9.26 (1H, s). |
| 1-167 | 448.1 | 2.12 | 0.52 (2H, m), 0.75 (2H, m), 2.86 (1H, m), 5.10 (2H, q), 6.72 (1H, m), 7.14 (2H, q), 7.21 (1H, m), 7.71 (2H, m), 8.02 (1H, m), 8.31 (1H, m), 8.52 (1H, s), 9.26 (1H, s). |
| 1-168 | 455.2 | 2.11 | 0.53 (2H, m), 0.76 (2H, m), 2.89 (1H, m), 5.11 (2H, q), 6.89 (1H, m), 7.22 (1H, m), 7.83 (4H, m), 8.01 (1H, m), 8.31 (1H, m), 8.56 (1H, s), 9.28 (1H, s). |
| 1-169 | 514.0 | 2.84 | 0.52 (2H, m), 0.75 (2H, m), 2.8 (1H, m), 5.11 (2H, q), 6.78 (1H, m), 7.21 (1H, m), 7.31 (2H, m), 7.77 (2H, m), 8.03 (1H, m), 8.32 (1H, m), 8.54 (1H, m), 9.28 (1H, s). |
| 1-170 | 418.3 | 1.59 | 0.50 (2H, m), 0.79 (3H, m), 2.91 (1H, m), 6.50 (1H, m), 7.26 (2H, t), 7.33 (2H, m), 7.93 (1H, m), 8.54 (1H, s), 8.80 (1H, m), 9.72 (1H, s). |
| 1-177 | 394.1 | 1.31 | 0.55 (2H, m), 0.78 (2H, m), 1.063 (3H, t), 2.89 (1H, m), 6.94 (1H, s), 7.28 (1H, m), 7.45 (2H, d), 7.67 (2H, d), 7.88 (1H, d), 8.52 (2H, m), 9.37 (1H, s). |
| 1-178 | 434.2 | 1.76 | 0.49 (2H, m), 0.80 (2H, m), 2.93 (1H, m), 6.56 (1H, m), 7.51 (2H, m), 7.70 (2H, m), 7.82 (1H, m), 7.96 (1H, m), 8.54 (1H, s), 8.81 (1H, m), 9.7 (1H, s). |
| 1-179 | 416.1 | 1.58 | |
| 1-180 | 390.1 | 1.10 | 0.57 (2H, m), 0.78 (2H, m), 1.02 (3H, t), 2.20 (3H, s), 2.42 (2H, q), 2.89 (1H, m), 6.82 (1H, s), 6.96 (1H, m), 7.07 (1H, m), 7.20 (2H, m), 7.68 (2H, m), 8.50 (2H, m), 9.21 (1H, s). |
| 1-181 | 397.2 | 1.22 | 0.58 (2H, m), 0.79 (2H, m), 1.00 (3H, t), 2.25 (3H, s), 2.38 (2H, q), 2.90 (1H, m), 6.97 (1H, m), 7.21 (1H, m), 7.38 (1H, m), 7.61 (1H, m), 7.71 (3H, m), 8.49 (1H, m), 8.52 (1H, s), 9.28 (1H, s). |
| 1-182 | 374.2 | 0.94 | |
| 1-183 | 393.1 | 0.94 | |
| 1-184 | | | (MeOH d4); (0.66 (2H, m), 0.89 (2H, m), 1.10 (3H, t), 2.21 (3H, s), 2.50 (2H, q), 2.88 (1H, m), 7.01 (1H, m), 7.07 (1H, m), 7.27 (1H, m), 7.32 (1H, m), 7.72 (1H, d), 8.49 (1H, m), 8.53 (1H, s). |
| 1-185 | | | (MeOH d4); 0.63 (2H, m), 0.89 (2H, m), 1.10 (3H, t), 2.55 (2H, q), 7.30 (1H, m), 7.36 (2H, d), 7.68 (2H, d), 7.91 (1H, m), 8.52 (2H, m). |
| 1-186 | | | (MeOH d4); 0.65 (2H, m); 0.89 (2H, m), 1.06 (3H, t), 2.49 (2H, q), 2.86 (1H, m), 7.31 (1H, m), 7.76 (4H, s), 7.94 (1H, m), 8.52 (1H, m), 8.56 (1H, s). |
| 1-187 | 412.1 | 1.46 | 0.56 (2H, m), 0.78 (2H, m), 1.05 (3H, t), 2.89 (1H, m), 6.90 (1H, s), 7.25 (1H, m), 7.33 (1H, m), 7.44 (2H, m), 7.76 (1H, m), 8.5 (2H, m), 9.38 (1H, s). |

TABLE 2-continued

Physicochemical characterization

| Ex. No. | MH+ | logP (HCOOH) | NMR (400 MHz, DMSO-d6, unless indicated otherwise) |
|---|---|---|---|
| 1-188 | 408.2 | 1.40 | 0.58 (2H, m), 0.78 (2H, m), 1.02 (3H, t), 2.20 (3H, s), 2.90 (1H, m), 6.86 (1H, m), 7.20 (3H, m), 7.32 (1H, m), 7.73 (1H, m), 8.50 (2H, m), 9.23 (1H, s). |
| 1-189 | 442.0 | 1.77 | 0.59 (2H, m), 0.78 (2H, m), 0.95 (3H, t), 2.28 (3H, s), 2.91 (1H, m), 6.93 (1H, m), 7.19 (1H, m), 7.40 (1H, m), 7.51 (1H, m), 7.60 (1H, m), 7.73 (1H, m), 8.47 (1H, m), 8.53 (1H, s), 9.28 (1H, s). |
| 1-196 | 446.2 | 2.43 | 0.56 (2H, m), 0.79 (2H, m), 1.07 (2H, q), 2.89 (1H, m), 7.04 (1H, m), 7.20 (2H, t), 7.68 (2H, m), 7.80 (1H, d), 8.18 (1H, d), 8.53 (1H, s), 9.56 (1H, s). |
| 1-197 | 440.1 | 2.52 | 0.58 (2H, m); 0.76 (4H, m), 0.86 (2H, m), 1.77 (1H, m); 2.86 (1H, m), 7.18 (1H, m), 7.42 (1H, m), 7.58 (2H, d), 8.14 (1H, m), 8.46 (1H, m), 8.52 (1H, s), 9.62 (1H, s). |
| 1-198 | 424.1 | 2.16 | 0.58 (2H, m), 0.73 (2H, m), 0.79 (2H, m), 0.86 (2H, m), 1.83 (1H, m), 2.87 (1H, m), 7.20 (1H, m), 7.61 (2H, m), 8.11 (1H, m), 8.45 (1H, m), 8.51 (1H, s), 9.61 (1H, s). |
| 1-199 | 448.1 | 2.35 | 0.57 (2H, m), 1.12 (2H, m), 2.47 (3H, s), (2.89 (1H, m), 7.15 (1H, s), 7.47 (2H, d), 7.65 (2H, d), 7.82 (1H, d), 8.16 (1H, d), 8.53 (1H, s), 9.57 (1H, s). |
| 1-224 | 392.1 | 1.36 | |
| 1-229 | 408.1 | 1.58 | |
| 1-230 | 426.1 | 1.72 | |
| 1-254 | 450.1 | 1.83 | |
| 1-258 | 577.3 | 2.07 | |
| 1-262 | 433 | 1.45 | (d7-DMF): 0.87 (8H, m), 3.03 (1H, m), 3.18 (1H, m), 7.39 (2H, t), 7.70 (m, 1H), 7.80 (3H, m), 8.19 (1H, d), 8.55 (1H, s), 8.68 (1H, dd), 9.11 (1H, bd), 9.72 (1H, bd) |
| 1-263 | 417 | 2.20 | 0.48 (2H, m), 0.84 (2H, m), 2.95 (1H, m), 6.01 (1H, bs), 7.35 (2H, m), 7.47 (3H, m), 7.68 (2H, m), 8.57 (1H, s), 10.06 (1H, s) |
| 1-264 | 591.2 | 1.9 | |
| 1-273 | 509.2 | 1.11 | |
| 1-275 | 374 | 0.76 | 0.55 (2 H, m), 0.76 (2 H, m), 1.05 (3 H, t), 2.53 (2 H, q), 2.92 (1 H, m), 6.63 (1 H, m), 7.24 (1 H, m), 7.38 (3 H, m), 7.60 (2 H, m), 7.80 (1 H, m), 8.51 (1 H, m), 9.27 (1 H, m). |
| 1-276 | 392 | 0.88 | 0.55 (2 H, m), 0.76 (2 H, m), 1.06 (3 H, t), 2.53 (2 H, q), 2.92 (1 H, m), 3.13 (3 H, s), 6.69 (1 H, m), 7.20 (2 H, m), 7.25 (1 H, m), 7.65 (2 H, m), 7.83 (1 H, m), 8.52 (1 H, m), 9.28 (1 H, m). |
| 1-277 | 442/444 | 1.34 | 0.55 (2 H, m), 0.77 (2 H, m), 1.03 (3 H, t), 2.45 (2 H, q), 2.93 (1 H, m), 6.66 (1 H, m), 7.21 (1 H, m), 7.43 (2 H, m), 7.60 (1 H, m), 7.68 (1 H, m), 8.49 (1 H, m), 9.22 (1 H, m). |
| 1-278 | 410 | 1 | 0.55 (2 H, m), 0.77 (2 H, m), 1.05 (3 H, t), 2.47 (3 H, s), 2.50 (2 H, q), 2.93 (1 H, m), 6.66 (1 H, m), 7.10 (1 H, m), 7.21 (2 H, m), 7.47 (1 H, m), 7.71 (1 H, m), 8.50 (1 H, m), 9.25 (1 H, m). |
| 1-279 | 458 | 1.44 | 0.55 (2 H, m), 0.76 (2 H, m), 1.03 (3 H, t), 2.92 (1 H, m), 6.75 (1 H, m), 7.24 (1 H, m), 7.35 (2 H, m), 7.73 (2 H, m), 7.85 (1 H, m), 8.52 (1 H, m), 9.31 (1 H, m). |
| 1-287 | 521.2 | 1.45 | |
| 1-290 | 605.2 | 2.47 | |
| 1-299 | 433.1 | 1.85 | 1.17 (3H, CH3), 1.40 (3H, CH3, s), 2.75 (2H, CH2), 5.23 (1H, m), 6.08 (1H, d), 7.20 (3H, m), 7.66 (3H, m), 8.14 (1H, s), 8.55 (2H, m) |
| 1-302 | 467 | 2.76 | 0.49 (2H, m), 0.80 (2H, m), 2.91 (1H, m), 6.48 (1H, m), 7.49 (2H, m), 7.57 (1H, d), 7.70 (2H, m), 7.87 (1H, m), 8.54 (1H, m), 9.65 (1H, bs) |
| 1-303 | 397 | 2.16 | 0.56 (2H, m), 0.76 (2H, m), 2.11 (3H, s), 2.88 (1H, m), 6.94 (1H, m), 7.19 (2H, m), 7.30 (2H, m), 7.54 (1H, d), 7.67 (2H, m), 8.50 (1H, s), 9.26 (1H, bs) |
| 1-304 | 413 | 2.44 | 0.56 (2H, m), 0.76 (2H, m), 2.11 (3H, s), 2.88 (1H, m), 6.97 (1H, m), 7.31 (2H, m), 7.44 (2H, m), 7.55 (1H, d), 7.66 (2H, m), 8.51 (1H, s), 9.27 (1H, bs) |
| 1-305 | 589.1 | 2.04 | |
| 1-306 | 535.1 | 1.84 | |
| 1-308 | 450 | 1.83 | 0.55 (2 H, m), 0.77 (2 H, m), 2.88 (1 H, m), 6.13 (1 H, dq), 7.18 (3 H, m), 7.67 (3 H, m), 8.23 (1 H, m), 8.54 (1 H, m), 8.80 (1 H, m), 8.89 (1 H, m). |
| 1-309 | 535.2 | 1.77 | |
| 1-310 | 555.1 | 1.84 | |
| 1-315 | 411 | 2.18 | (d3-MeCN): 0.53 (2H, m), 0.83 (2H, m), 0.92 (3H, t), 2.02 (2H, q), 2.95 (1H, m), 6.03 (1H, m), 7.19 (3H, m), 7.31 (2H, m), 7.55 (2H, m), 8.11 (1H, bs), 8.55 (1H, s) |
| 1-316 | 427 | 2.54 | (d3-MeCN): 0.53 (2H, m), 0.83 (2H, m), 0.93 (3H, t), 2.01 (2H, q), 2.94 (1H, m), 6.03 (1H, bs), 7.20 (1H, m), 7.30 (2H, m), 7.48 (3H, m), 7.63 (1H, m), 8.09 (1H, bs), 8.56 (1H, s) |
| 1-320 | 391 | 2.39 | 0.47 (2H, m), 0.82 (2H, m), 0.98 (3H, t), 2.03 (3H, s), 2.20 (2H, q), 2.91 (1H, m), 6.48 (1H, m), 7.03 (2H, m), 7.25 (3H, m), 7.61 (2H, dd), 8.53 (1H, s), 9.45 (1H, bs) |
| 1-321 | 418 | 2.37 | 0.47 (2H, m), 0.85 (5H, m), 1.97 (2H, q), 2.93 (1H, m), 6.42 (1H, m), 7.24 (1H, m), 7.36 (2H, m), 7.55 (2H, d), 7.72 (2H, d), 8.59 (1H, s), 9.93 (1H, s) |
| 1-327 | 413 | 2.42 | 0.57 (2H, m), 0.77 (2H, m), 1.96 (3H, s), 2.84 (1H, m), 7.22 (1H, m), 7.42 (4H, m), 7.62 (2H, m), 7.73 (1H, m), 8.52 (1H, s), 9.50 (1H, bs) |
| 1-328 | 397 | 2.07 | 0.57 (2H, m), 0.77 (2H, m), 1.96 (3H, s), 2.84 (1H, m), 7.22 (3H, m), 7.38 (2H, m), 7.65 (2H, m), 7.73 (1H, m), 8.52 (1H, s), 9.49 (1H, bs) |
| 1-329 | 441, 443 | 2.17 | 0.56 (2H, m), 0.76 (2H, m), 2.05 (3H, s), 2.84 (1H, m), 7.24 (3H, m), 7.46 (2H, m), 7.55 (1H, d), 7.67 (2H, dd), 8.51 (1H, s), 9.38 (1H, bs) |
| 1-330 | 413 | 2.39 | 0.55 (2H, m), 0.78 (2H, m), 2.04 (3H, s), 2.86 (1H, m), 7.29 (2H, m), 7.50 (4H, m), 7.66 (2H, m), 8.54 (1H, s), 9.44 (1H, bs) |

TABLE 3

Compounds of the formula

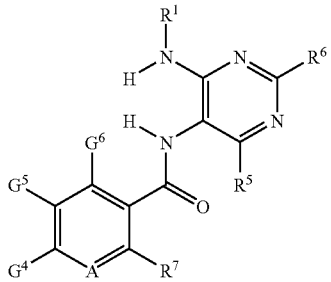

| Ex. No. | $R^1$ | $R^5$ | $R^7$ | $R^6$ | A | $G^4$ | $G^5$ | $G^6$ |
|---|---|---|---|---|---|---|---|---|
| 3-1 | cyclopropyl | Cl | $CH_2CH_3$ | H | N | H | H | H |
| 3-2 | cyclopropyl | H | $CH_2CH_3$ | H | N | H | H | H |
| 3-3 | cyclopropyl | Br | $CH_2CH_3$ | H | N | H | H | H |
| 3-4 | cyclopropyl | Cl | $OCH_2CF_3$ | H | N | H | H | H |
| 3-5 | cyclopropyl | Cl | $CH_2CF_3$ | H | N | H | H | H |
| 3-6 | cyclobutyl | Cl | $CH_2CH_3$ | H | N | H | H | H |

TABLE 3-continued

Compounds of the formula

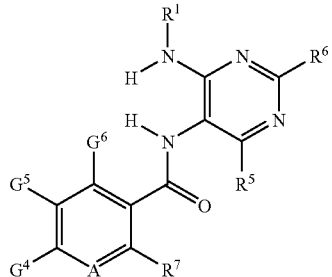

| Ex. No. | R¹ | R⁵ | R⁷ | R⁶ | A | G⁴ | G⁵ | G⁶ |
|---|---|---|---|---|---|---|---|---|
| 3-7 | R-cyclopropyl | Cl | CH₂CH₃ | H | N | H | H | H |
| 3-8 | cyclopropyl | CH₂CH₃ | CH₂CH₃ | H | N | H | H | H |
| 3-9 | cyclopropyl | Cl | CH₂CH₃ | CH₃ | N | H | H | H |
| 3-10 | CH(CF₃)CH₃ | Cl | CH₂CH₃ | CH₃ | N | H | H | H |
| 3-11 | cyclopropyl | Cl | CH₂CH₃ | CF₃ | N | H | H | H |
| 3-12 | R-(F-cyclopropyl) | Cl | CH₂CH₃ | H | N | H | H | H |
| 3-13 | cyclopropyl | cyclopropyl | CH₂CF₃ | Cl | N | H | H | H |
| 3-14 | R-CH(CH₃)phenyl | Cl | CH₂CH₃ | CH₃ | N | H | H | H |
| 3-15 | R-CH(CH₃)phenyl | Cl | CH₂CH₃ | H | N | H | H | H |
| 3-16 | R-CH₂-phenyl | Cl | CH₂CH₃ | H | N | H | H | H |

TABLE 4

Physicochemical characterization

| Ex. No. | MH+ | logP (HCOOH) |
|---|---|---|
| 3-1 | 318.2 | 0.79 |
| 3-3 | 364.1 | 0.84 |
| 3-4 | 388.0 | 2.25 |
| 3-5 | 370.1 | 1.61 |
| 3-6 | 331.1 | 1.34 |
| 3-7 | 331.1 | 1.26 |
| 3-8 | 312.2 | 1.74 |
| 3-9 | 332.2 | 1.41 |
| 3-10 | 374.0 | 1.65 |
| 3-11 | 384.1 | 2.27 |
| 3-12 | 412.1 | 2.22 |

TABLE 5

Compounds of the formula

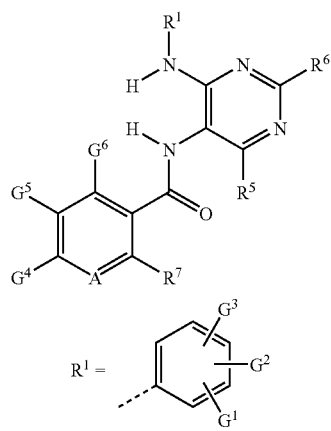

| Ex. No. | G¹ | G² | G³ | R⁵ | R⁷ | R⁶ | A | G⁴ | G⁵ | G⁶ |
|---|---|---|---|---|---|---|---|---|---|---|
| 5-1 | 4-Cl | H | H | Cl | CH₂CH₃ | H | N | H | H | H |
| 5-2 | 4-F | H | H | Cl | CH₂CH₃ | H | N | H | H | H |
| 5-3 | 2-CH₃ | 4-CH₂-(triazole-C₂F₅,CF₃) | | H | Cl | CH₂CH₃ | H | N | H | H | H |
| 5-4 | 2-CH₃ | 4-C₃F₇ | H | Cl | CH₂CH₃ | H | N | H | H | H |
| 5-5 | 4-CF₃ | H | H | Cl | CH₂CH₃ | H | N | H | H | H |
| 5-6 | 4-CN | H | H | Cl | CH₂CH₃ | H | N | H | H | H |
| 5-7 | 2-CH₃ | 4-CH₂-(triazole-C₂F₅,CF₃) | | H | Cl | CH₂CH₃ | H | N | H | H | H |
| 5-8 | 2-F | 4-F | H | Cl | CH₂CH₃ | H | N | H | H | H |

TABLE 6

Physicochemical characterization

| Ex. No. | MH+ | logP (HCOOH) |
|---|---|---|
| 5-1 | 388.1 | 1.75 |
| 5-2 | 372.1 | 1.25 |
| 5-3 | 635.1 | 3.20 |
| 5-4 | 536.1 | 3.68 |
| 5-5 | 422.1 | 2.12 |
| 5-6 | 379.1 | 1.38 |
| 5-7 | 585.1 | 2.62 |
| 5-8 | 390.1 | 1.40 |

TABLE 7

Compounds of the formula

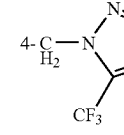

| Ex. No. | R¹ | R⁹ | R¹⁰ | R¹¹ | R⁵ | G¹ | G² | G³ | R⁶ | A |
|---|---|---|---|---|---|---|---|---|---|---|
| 7-1 | cyclopropyl | CH₂CH₃ | H | H | Ph | 4-F | H | H | H | N |
| 7-2 | cyclopropyl | CH₂CH₃ | H | Cl | Ph | 4-F | H | H | H | N |
| 7-3 | cyclopropyl | CH₂CH₃ | H | H | Ph | H | H | H | H | N |
| 7-4 | cyclopropyl | CH₂CH₃ | H | H | Ph | 4-Cl | H | H | H | N |
| 7-5 | cyclopropyl | CH₂CH₃ | H | H | Ph | 4-OCF₃ | H | H | H | N |
| 7-6 | cyclopropyl | CH₂CH₃ | H | H | Ph | 4-SCF₃ | H | H | H | N |
| 7-7 | cyclopropyl | CH₂CH₃ | H | Cl | Ph | H | H | H | H | N |
| 7-8 | cyclopropyl | CH₂CH₃ | H | Cl | Ph | 4-Cl | H | H | H | N |
| 7-9 | cyclopropyl | CH₂CH₃ | H | Cl | Ph | 4-OCF₃ | H | H | H | N |
| 7-10 | cyclopropyl | CH₂CH₃ | H | Cl | Ph | 4-SCF₃ | H | H | H | N |
| 7-11 | cyclopropyl | CH₂CH₃ | 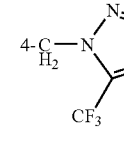 | H | Cl | H | H | H | H | N |
| 7-12 | cyclopropyl | CH₂CH₃ | H | H | Ph | 4-CN | H | H | H | N |
| 7-13 | cyclopropyl | CH₂CH₃ | 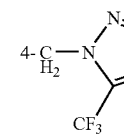 | H | Ph | H | H | H | H | N |
| 7-14 | cyclopropyl | CH₂CH₃ | 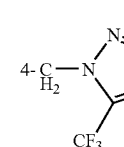 | H | Ph | 2-Cl | 4-Cl | H | H | N |
| 7-15 | cyclopropyl | CH₂CH₃ | 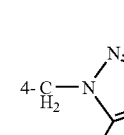 | H | Ph | 4-OCF₃ | H | H | H | N |
| 7-16 | cyclopropyl | CH₂CH₃ | | H | Ph | 4-Cl | H | H | H | N |

TABLE 7-continued

Compounds of the formula

[Structure with R¹NH, N, R⁶, R⁵, R¹¹, R¹⁰, A, R⁹, and R¹ = phenyl with G¹, G², G³ substituents]

| Ex. No. | R¹ | R⁹ | R¹⁰ | R¹¹ | R⁵ | G¹ | G² | G³ | R⁶ | A |
|---|---|---|---|---|---|---|---|---|---|---|
| 7-17 | cyclopropyl | CH₂CH₃ | [pyrazole: 4-CH₂-N-pyrazole with 3-C₂F₅ and 5-CF₃] | H | Ph | 4-F | H | H | H | N |
| 7-18 | cyclopropyl | CH₂CH₃ | H | H | Ph | 2-Cl | 4-Cl | H | H | N |
| 7-19 | cyclopropyl | CH₂CH₃ | H | Cl | Ph | 2-Cl | 4-Cl | H | H | N |
| 7-20 | cyclopropyl | CH₂CH₃ | H | Cl | Ph | 4-CN | H | H | H | N |
| 7-21 | cyclopropyl | CH(CH₃)₂ | H | Cl | Ph | 4-F | H | H | H | N |
| 7-22 | cyclopropyl | CH(CH₃)₂ | H | Cl | Ph | 4-Cl | H | H | H | N |
| 7-23 | cyclopropyl | CH₂CF₃ | H | H | Ph | 4-F | H | H | H | N |
| 7-24 | cyclopropyl | n-propyl | H | Cl | Ph | 4-F | H | H | H | N |
| 7-25 | cyclopropyl | n-propyl | H | Cl | Ph | 4-Cl | H | H | H | N |

TABLE 8

Physicochemical characterization

| Ex. No. | MH+ | logP (HCOOH) | NMR (DMSO d6. 400 MHz) |
|---|---|---|---|
| 7-1 | 367 | 1.31 | 0.52 (2 H, m), 0.77 (2 H, m), 1.22 (3 H, t), 2.91 (1 H, m), 4.12 (2 H, q), 6.86 (1 H, m), 7.18 (2 H, m), 7.59 (1 H, s), 7.71 (2 H, m), 8.53 (1 H, s), 9.19 (1 H, s) |
| 7-2 | 401/403 | 1.86 | 0.51 (2 H, m), 0.77 (2 H, m), 1.21 (3 H, t), 2.87 (1 H, m), 4.14 (2 H, q), 7.23 (2 H, m), 7.26 (1 H, m), 7.64 (1 H, s), 7.71 (2 H, m), 8.54 (1 H, s), 9.27 (1 H, s) |
| 7-3 | 349 | 1.12 | 0.56 (2 H, m), 0.73 (2 H, m), 1.18 (3 H, t), 2.87 (1 H, m), 4.30 (2 H, q), 6.84 (1 H, m), 7.12 (1H, m), 7.33 (3 H, m), 7.43 (1 H, m), 7.63 (2 H, m), 8.51 (1 H, s), 9.36 (1 H, s) |
| 7-4 | 383/385 | 1.6 | 0.55 (2 H, m), 0.74 (2 H, m), 1.16 (3 H, t), 2.84 (1 H, m), 4.31 (2 H, q), 6.85 (1 H, m), 7.42 (2 H, m), 7.48 (1 H, m), 7.65 (2 H, m), 8.52 (1 H, s), 9.55 (1 H, s) |
| 7-5 | 433 | 1.99 | 0.57 (2 H, m), 0.74 (2 H, m), 1.14 (3 H, t), 2.88 (1 H, m), 4.29 (2 H, q), 6.87 (1 H, m), 7.22 (1 H, m), 7.30 (2 H, m), 7.44 (1 H, m), 7.75 (2 H, m), 8.52 (1 H, s), 9.39 (1 H, s) |
| 7-6 | 449 | 2.29 | 0.57 (2 H, m), 0.74 (2 H, m), 1.13 (3 H, t), 2.89 (1 H, m), 4.27 (2 H, q), 6.86 (1 H, m), 7.25 (1 H, m), 7.44 (1 H, m), 7.66 (2 H, m), 7.76 (2 H, m), 8.53 (1 H, s), 9.41 (1 H, s) |
| 7-7 | 383 | 1.63 | 0.52 (2 H, m), 0.77 (2 H, m), 1.19 (3 H, t), 2.91 (1 H, m), 4.09 (2 H, q), 6.78 (1 H, m), 7.37 (3 H, m), 7.58 (1 H, m), 7.65 (2 H, m), 8.54 (1 H, s), 9.21 (1 H, s) |
| 7-8 | 417/419 | 2.20 | 0.52 (2 H, m), 0.77 (2 H, m), 1.20 (3 H, t), 2.91 (1 H, m), 4.12 (2 H, q), 6.90 (1 H, m), 7.43 (2 H, m), 7.59 (1 H, m), 7.64 (1 H, s), 7.68 (2 H, m), 8.54 (1 H, s), 9.20 (1 H, s) |
| 7-9 | 467/469 | 2.63 | 0.52 (2 H, m), 0.77 (2 H, m), 1.20 (3 H, t), 2.92 (1 H, m), 4.11 (2 H, q), 6.88 (1 H, m), 7.35 (2 H, m), 7.58 (1 H, s), 7.75 (2 H, m), 8.55 (1 H, s), 9.24 (1 H, s) |
| 7-10 | 483/485 | 2.99 | 0.52 (2 H, m), 0.77 (2 H, m), 1.19 (3 H, t), 2.92 (1 H, m), 4.10 (2 H, q), 6.88 (1 H, m), 7.58 (1 H, s), 7.74 (4 H, m), 8.56 (1 H, s), 9.25 (1 H, s) |
| 7-11 | 523/525 | 3.29 | 0.52 (2 H, m), 0.72 (2 H, m), 1.31 (3 H, t), 2.83 (1 H, m), 4.45 (2 H, q), 5.57 (2 H, s), 6.94 (1 H, m), 7.49 (2 H, m), 8.27 (1 H, s), 9.57 (1 H, s) |
| 7-12 | 374 | 1.45 | 0.58 (2 H, m), 0.74 (2 H, m), 1.15 (3 H, t), 2.88 (1 H, m), 4.28 (2 H, q), 6.86 (1 H, m), 7.31 (1 H, m), 7.45 (1 H, m), 7.79 (4 H, m), 8.54 (1 H, s), 9.40 (1 H, s) |
| 7-13 | 565 | 2.80 | 0.53 (2 H, m), 0.72 (2 H, m), 1.17 (3 H, t), 2.86 (1 H, m), 4.27 (2 H, q), 5.52 (2 H, s), 6.72 (1 H, m), 7.18 (1 H, m), 7.30 (3 H, m), 7.51 (1 H, s), 7.60 (2 H, m), 8.50 (1 H, s), 9.41 (1 H, s) |
| 7-14 | 633/635 | 3.79 | 0.54 (2 H, m), 0.73 (2 H, m), 1.14 (3 H, t), 2.87 (1 H, m), 4.23 (2 H, q), 5.50 (2 H, s), 6.62 (1 H, m), 7.21 (1 H, m), 7.28 (2 H, m), 7.49 (2 H, m), 8.49 (1 H, s), 9.29 (1 H, s) |

TABLE 8-continued

Physicochemical characterization

| Ex. No. | MH+ | logP (HCOOH) | NMR (DMSO d6. 400 MHz) |
|---|---|---|---|
| 7-15 | 649 | 3.76 | 0.54 (2 H, m), 0.73 (2 H, m), 1.14 (3 H, t), 2.86 (1 H, m), 4.26 (2 H, q), 5.53 (2 H, s), 6.74 (1 H, m), 7.26 (3 H, m), 7.50 (1 H, s), 7.71 (2 H, m), 8.50 (1 H, s), 9.43 (1 H, s) |
| 7-16 | 599/601 | 3.41 | 0.53 (2 H, m), 0.72 (2 H, m), 1.17 (3 H, t), 2.85 (1 H, m), 4.28 (2 H, q), 5.53 (2 H, s), 6.77 (1 H, m), 7.26 (1 H, m), 7.35 (2 H, m), 7.50 (1 H, m), 7.60 (2 H, m), 8.50 (1 H, s), 9.42 (1 H, s) |
| 7-17 | 583 | 3.05 | 0.52 (2 H, m), 0.73 (2 H, m), 1.17 (3 H, t), 2.85 (1 H, m), 4.28 (2 H, q), 5.54 (2 H, s), 6.74 (1 H, m), 7.11 (2 H, m), 7.23 (1 H, m), 7.51 (1 H, s), 7.66 (2 H, m), 8.49 (1 H, s), 9.41 (1 H, s) |
| 7-18 | 417/419 | 1.95 | 0.57 (2 H, m), 0.76 (2 H, m), 1.15 (3 H, t), 2.88 (1 H, m), 4.27 (2 H, q), 6.73 (1 H, m), 7.17 (1 H, m), 7.3-7.6 (4 H, m), 8.59 (1 H, s), 9.25 (1 H, s) |
| 7-19 | 451/453 | 2.57 | |
| 7-20 | 408/410 | 1.90 | 0.53 (2 H, m), 0.76 (2 H, m), 1.20 (3 H, t), 2.91 (1 H, m), 4.11 (2 H, q), 7.03 (1 H, m), 7.58 (1 H, m), 7.82 (4 H, m), 8.56 (1 H, s), 9.21 (1 H, s) |
| 7-21 | 415 | 2.18 | 0.49 (2H, m), 0.78 (2H, m), 1.27 (6H, d), 2.91 (1H, m), 4.55 (1H, m), 6.66 (1H, bs), 7.20 (2H, m), 7.61 (1H, s), 7.70 (2H, m), 8.54 (1H, s), 9.36 (1H, bs) |
| 7-22 | 431 | 2.58 | 0.49 (2H, m), 0.78 (2H, m), 1.27 (6H, d), 2.92 (1H, m), 4.54 (1H, m), 6.69 (1H, bs), 7.44 (2H, m), 7.61 (1H, s), 7.67 (2H, m), 8.54 (1H, s), 9.37 (1H, bs) |
| 7-23 | 421 | 1.68 | 0.54 (2H, m), 0.75 (2H, m), 2.86 (1H, m), 5.34 (2H, m), 7.09 (1H, s), 7.17 (2H, m), 7.39 (1H, s), 7.68 (3H, m), 8.54 (1H, s), 9.76 (1H, bs) |
| 7-24 | 415 | 2.13 | 0.49 (2H, m), 0.75 (5H, m), 1.57 (2H, m), 2.88 (1H, m), 4.06 (t, 2H), 7.07 (1H, m), 7.22 (2H, m), 7.64 (1H, m), 7.73 (2H, m), 8.54 (1H, s), 9.30 (1H, bs) |
| 7-25 | 431 | 2.51 | 0.49 (2H, m), 0.74 (5H, m), 1.57 (2H, m), 2.88 (1H, m), 4.05 (t, 2H), 7.10 (1H, m), 7.46 (2H, m), 7.65 (1H, m), 7.69 (2H, m), 8.55 (1H, s), 9.31 (1H, bs) |

TABLE 10

Physicochemical characterization

| Ex. No. | MH+ | logP (HCOOH) | NMR (DMSO d6, 400 MHz) |
|---|---|---|---|
| 9-1 | 433 | 1.70 | 0.57 (2H, m), 0.78 (2H, m), 2.87 (1H, m), 7.06 (1H, s), 7.20 (4H, m), 7.32 (2H, m), 7.51 (1H, m), 7.73 (3H, m), 8.50 (1H, s), 9.69 (1H, bs) |
| 9-2 | 449 | 2.02 | 0.57 (2H, m), 0.77 (2H, m), 2.87 (1H, m), 7.07 (1H, s), 7.18 (2H, m), 7.31 (2H, m), 7.49 (3H, m), 7.66 (2H, m), 7.76 (1H, s), 8.51 (1H, s), 9.70 (1H, bs) |
| 9-3 | 449 | 1.76 | 0.52 (2H, m), 0.73 (2H, m), 2.81 (1H, m), 7.18 (4H, m), 7.27 (1H, m), 7.35 (1H, m), 7.42 (1H, m), 7.49 (1H, m), 7.67 (2H, m), 7.80 (1H, m), 8.48 (1H, s), 9.68 (1H, bs) |
| 9-4 | 465 | 2.05 | 0.53 (2H, m), 0.73 (2H, m), 2.81 (1H, m), 7.18 (1H, m), 7.24 (2H, m), 7.35 (1H, m), 7.44 (3H, m), 7.52 (1H, m), 7.63 (2H, m), 7.81 (1H, m), 8.49 (1H, s), 9.68 (1H, bs) |

Biological Examples

*Lucilia Cuprina* Test

Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing horse meat treated with the active compound preparation of the desired concentration are populated with *Lucilia cuprina* larvae.

After 48 hours, the activity in % is determined. 100% means that all larvae have been killed; 0% means that none of the larvae has been killed.

In this test, for example, the following compounds of the Preparation Examples exhibit an activity of ≧80% at an application rate of 100 ppm:

Ex. Nos.: 1-1, 1-21, 1-4, 1-5, 1-73, 1-74, 1-75, 1-76, 1-82, 1-83, 1-85, 1-86, 1-88, 1-100, 1-111, 1-113, 1-114, 1-116, 1-123, 1-124, 1-126, 1-133, 1-177, 1-179, 1-180, 1-181, 1-185, 1-186, 1-187, 1-188, 1-190

*Musca Domestica* Test

Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with the active compound preparation of the desired concentration are populated with adult *Musca domestica*.

After 2 days, the activity in % is determined. 100% means that all flies have been killed; 0% means that none of the flies has been killed.

In this test, for example, the following compounds of the Preparation Examples exhibit an activity of ≧80% at an application rate of 100 ppm:

Ex. Nos.: 1-1, 1-4, 1-73, 1-75, 1-88, 1-114, 1-124, 1-126, 1-177, 1-179, 1-180, 1-181, 1-185, 1-186, 1-187, 1-190

*Boophilus Microplus* Test (Injection)

Solvent: dimethyl sulphoxide

To produce a suitable preparation of active compound, 10 mg of active compound are mixed with 0.5 ml of solvent, and the concentrate is diluted with water to the desired concentration. The solution of active compound is injected into the abdomen (*Boophilus microplus*), the animals are transferred into dishes and stored in a climatized room. Activity is assessed via oviposition of fertile eggs.

After 7 days, the activity in % is determined. 100% means that none of the ticks has laid any fertile eggs.

In this test, for example, the following compounds of the Preparation Examples exhibit an activity of ≧80% at an application rate of 20 μg/animal:

Ex. Nos.: 1-5, 1-100, 1-111, 1-177, 1-187

*Myzus* Test (Spray Treatment)

Solvents:

78 parts by weight of acetone 1.5 parts by weight of dimethylformamide

Emulsifier: 0.5 part by weight of alkylaryl polyglycol ether

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with an active compound preparation of the desired concentration After 6 days, the activity in % is determined. 100% means that all aphids have been killed; 0% means that none of the aphids has been killed.

In this test, for example, the following compounds of the Preparation Examples exhibit an activity of ≧80% at an application rate of 500 ppm:

Ex. Nos.: 1-1, 1-10, 1-11, 1-114, 1-115, 1-116, 1-121, 1-123, 1-124, 1-126, 1-127, 1-129, 1-13, 1-130, 1-131, 1-132, 1-133, 1-139, 1-145, 1-146, 1-147, 1-148, 1-149, 1-150, 1-152, 1-154, 1-16, 1-174, 1-175, 1-176, 1-177, 1-178, 1-179, 1-180, 1-181, 1-183, 1-184, 1-185, 1-186, 1-187, 1-188, 1-189, 1-19, 1-190, 1-20, 1-21, 1-26, 1-27, 1-22, 1-23, 1-24, 1-25, 1-29, 1-30, 1-31, 1-32, 1-33, 1-37, 1-38, 1-4, 1-40, 1-44, 1-48, 1-5, 1-52, 1-59, 1-60, 1-7, 1-70, 1-71, 1-8, 1-9, 1-100, 1-112, 1-73, 1-85, 1-99

Phaedon Test (Spray Treatment)
Solvents:
78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After 7 days, the activity in % is determined. 100% means that all beetle larvae have been killed; 0% means that none of the beetle larvae has been killed.

In this test, for example, the following compounds of the Preparation Examples exhibit an activity of ≧80% at an application rate of 500 ppm:

Ex. Nos.: 1-1, 1-11, 1-114, 1-115, 1-116, 1-119, 1-122, 1-123, 1-124, 1-126, 1-127, 1-129, 1-13, 1-130, 1-131, 1-132, 1-133, 1-134, 1-135, 1-136, 1-137, 1-139, 1-14, 1-140, 1-141, 1-142, 1-143, 1-144, 1-149, 1-15, 1-151, 1-154, 1-156, 1-157, 1-158, 1-159, 1-16, 1-160, 1-161, 1-162, 1-163, 1-164, 1-165, 1-167, 1-169, 1-170, 1-172, 1-173, 1-174, 1-175, 1-176, 1-177, 1-178, 1-179, 1-180, 1-181, 1-183, 1-184, 1-185, 1-186, 1-187, 1-188, 1-189, 1-19, 1-190, 1-191, 1-192, 1-193, 1-194, 1-195, 1-2, 1-20, 1-21, 1-25, 1-29, 1-3, 1-30, 1-33, 1-34, 1-37, 1-38, 1-4, 1-40, 1-43, 1-44, 1-45, 1-46, 1-47, 1-48, 1-49, 1-5, 1-52, 1-56, 1-58, 1-6, 1-60, 1-61, 1-64, 1-67, 1-68, 1-69, 1-7, 1-70, 1-71, 1-83, 1-84, 1-87, 1-9, 1-111, 1-112, 1-113, 1-72, 1-73, 1-74, 1-75, 1-76, 1-78, 1-82, 1-83, 1-85, 1-86, 1-88, 1-89, 1-99

*Spodoptera Frugiperda* Test (Spray Treatment)
Solvents:
78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After 7 days, the activity in % is determined. 100% means that all caterpillars have been killed; 0% means that none of the caterpillars has been killed.

In this test, for example, the following compounds of the Preparation Examples exhibit an activity of ≧80% at an application rate of 500 ppm:

Ex. Nos.: 1-1, 1-10, 1-11, 1-114, 1-115, 1-12, 1-123, 1-124, 1-126, 1-127, 1-129, 1-13, 1-130, 1-131, 1-132, 1-133, 1-134, 1-135, 1-139, 1-14, 1-143, 1-146, 1-147, 1-149, 1-15, 1-151, 1-152, 1-155, 1-159, 1-16, 1-160, 1-164, 1-167, 1-170, 1-172, 1-173, 1-174, 1-176, 1-177, 1-183, 1-185, 1-186, 1-187, 1-188, 1-189, 1-19, 1-190, 1-191, 1-192, 1-2, 1-20, 1-21, 1-22, 1-25, 1-29, 1-3, 1-30, 1-4, 1-5, 1-6, 1-67, 1-7, 1-70, 1-71, 1-8, 1-9, 1-111, 1-72, 1-73, 1-74, 1-75, 1-76, 1-81, 1-83, 1-85, 1-86, 1-99

TABLE 9

Compounds of the formula

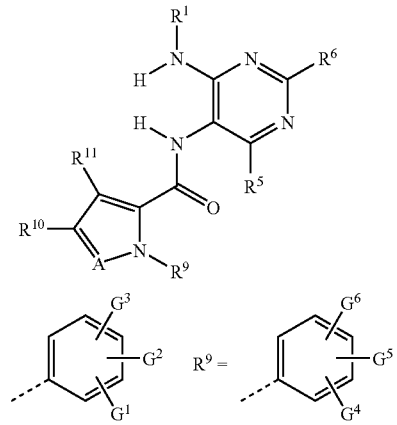

| Ex. No. | $R^1$ | $G^4$ | $G^5$ | $G^6$ | $R^{10}$ | $R^{11}$ | $G^1$ | $G^2$ | $G^3$ | $R^6$ | A |
|---|---|---|---|---|---|---|---|---|---|---|---|
| 9-1 | cyclopropyl | 4-F | H | H | H | H | 4-F | H | H | H | N |
| 9-2 | cyclopropyl | 4-Cl | H | H | H | H | 4-F | H | H | H | N |
| 9-3 | cyclopropyl | 2-Cl | H | H | H | H | 4-F | H | H | H | N |
| 9-4 | cyclopropyl | 2-Cl | H | H | H | H | 4-Cl | H | H | H | N |

*Tetranychus* Test, OP-Resistant (Spray Treatment)
Solvents:
78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) infested by all stages of the greenhouse red spider mite (*Tetranychus urticae*) are sprayed with an active compound preparation of the desired concentration.

After 6 days, the activity in % is deteimined. 100% means that all spider mites have been killed; 0% means that none of the spider mites has been killed.

In this test, for example, the following compounds of the Preparation Examples exhibit an activity of ≧80% at an application rate of 500 ppm:

Ex. Nos.: 1-116, 1-192, 1-199, 1-5, 1-83

*Boophilus Microplus*—Test (Injection)
Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (Boophilus microplus) are injected with 1 μl compound solution into the abdomen. Ticks are transferred into replica plates and incubated in a climate chamber for a period of time. Egg deposition of fertile eggs is monitored.

After 7 days mortality in % is determined. 100% means that all eggs are infertile; 0% means that all eggs are fertile.

In this test for example, the following compounds from the preparation examples showed good activity of ≧80% at application rate of 20 μg/animal:

| 1-222 | 1-225 | 1-245 | 1-274 |
| 1-224 | 1-235 | 1-254 | 1-299 |

*Lucilia Cuprina* (48h)
species: *Lucilia cuprina* 1$^{st}$ instar larvae (age 24 hrs)
Solvent: dimethyl sulfoxide 10 mg active compound are dissolve in 0.5 ml Dimethylsulfoxid. Serial dilutions are made to obtain the desired rates. Approximately 20-30 *Lucilia cuprina* 1$^{st}$ instar larvae are transferred into a test tube containing 1 cm$^3$ of minced horse meat and 0.5 ml aqueous dilution of test compound. After 48 hrs percentage of larval mortality are recorded. 100% efficacy=all larvae are killed, % efficacy=normally developed larvae after 48 hrs.

In this test for example, the following compounds from the preparation examples showed good activity of ≧80% at application rate of 100 ppm:

| 1-127 | 1-176 | 1-234 | 1-246 | 1-279 | 7-1 |
| 1-131 | 1-222 | 1-235 | 1-254 | 1-299 | 7-2 |
| 1-132 | 1-224 | 1-238 | 1-255 | 1-305 | 7-20 |
| 1-147 | 1-225 | 1-239 | 1-258 | 1-308 | |
| 1-172 | 1-230 | 1-245 | 1-274 | 1-326 | |

*Musca Domestica*—Test
Solvent: dimethyl sulfoxide

To produce a suitable preparation of active compound, 10 mg of active compound are dissolved in 0.5 ml solvent, and the concentrate is diluted with water to the desired concentration. Prior to the assay, a piece or kitchen sponge is soaked with a mixture of sugar and compound solution and placed into a container. 10 adults (*Musca domestica*) are placed into the container and closed with a perforated lid. After 2 days mortality in % is determined. 100% means that all the flies have been killed; 0% means that none of the flies have been killed.

In this test for example, the following compounds from the preparation examples showed good activity of ≧80% at application rate of 100 ppm:

| 1-147 | 1-238 | 1-246 | 1-258 | 1-258 |
| 1-172 | 1-239 | 1-254 | 1-274 | 1-274 |
| 1-234 | 1-245 | 1-255 | 1-279 | 1-279 |
| 7-2 | | | | |

In this test for example, the following compounds from the preparation examples showed good activity of ≧80% at application rate of 20 ppm:
1-127, 1-222, 1-224, 1-225, 1-230, 1-299, 7-20

*Myzus Persicae*—Test; (Spray Application)
Solvent:
78.0 parts by weight acetone
1.5 parts by weight dimethylformamide
Emulsifier: 0.5 parts by weight alkylarylpolyglcolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks infected with all instars of the green peach aphid (*Myzus persicae*), are sprayed with a preparation of the active ingredient at the desired concentration.

After 6 days mortality in % is determined. 100% means that all aphids have been killed; 0% means that none of the aphids have been killed.

In this test for example, the following compounds from the preparation examples showed good activity of ≧80% at application rate of 500 g/ha:

| 1-22  | 1-229 | 1-242 | 1-272 | 1-279 | 1-314 | 3-4  | 3-12 | 7-23 |
| 1-222 | 1-230 | 1-246 | 1-274 | 1-289 | 1-316 | 3-5  | 7-1  | 9-1  |
| 1-223 | 1-231 | 1-254 | 1-275 | 1-299 | 1-322 | 3-6  | 7-2  |      |
| 1-224 | 1-235 | 1-258 | 1-276 | 1-301 | 1-325 | 3-7  | 7-7  |      |
| 1-225 | 1-236 | 1-261 | 1-277 | 1-307 | 1-326 | 3-8  | 7-20 |      |
| 1-226 | 1-239 | 1-271 | 1-278 | 1-308 | 3-1   | 3-11 | 7-21 |      |

*Phaedon Cochleariae*—Test; (Spray Application)
Solvent:
78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinesis*) leaf-disks are sprayed with a preparation of the active ingredient of the desired concentration. Once dry, the leaf disks are infested with mustard beetle larvae (*Phaedon cochleariae*).

After 7 days mortality in % is determined. 100% means that all beetle larvae have been killed and 0% means that none of the beetle larvae have been killed.

In this test for example, the following compounds from the preparation examples showed good activity of ≧80% at application rate of 500 g/ha:

| 1-221 | 1-238 | 1-263 | 1-283 | 1-301 | 1-327 | 7-11 | 7-25 |
| 1-222 | 1-239 | 1-265 | 1-284 | 1-302 | 1-328 | 7-13 | 7-3  |
| 1-223 | 1-241 | 1-271 | 1-285 | 1-303 | 1-329 | 7-14 | 7-4  |
| 1-224 | 1-242 | 1-274 | 1-289 | 1-304 | 1-330 | 7-15 | 7-5  |
| 1-225 | 1-246 | 1-275 | 1-293 | 1-307 | 1-331 | 7-16 | 7-6  |
| 1-226 | 1-250 | 1-276 | 1-294 | 1-308 | 1-332 | 7-17 | 7-7  |
| 1-227 | 1-254 | 1-277 | 1-295 | 1-315 | 3-13  | 7-18 | 7-8  |
| 1-229 | 1-255 | 1-278 | 1-296 | 1-320 | 3-7   | 7-2  | 7-9  |
| 1-230 | 1-256 | 1-279 | 1-297 | 1-321 | 3-8   | 7-20 | 9-1  |
| 1-231 | 1-258 | 1-280 | 1-298 | 1-322 | 3-9   | 7-21 | 9-2  |
| 1-235 | 1-260 | 1-281 | 1-299 | 1-325 | 7-1   | 7-22 | 9-3  |
| 1-236 | 1-261 | 1-282 | 1-300 | 1-326 | 7-10  | 7-24 | 9-4  |

*Spodoptera Frugiperda*—Test (Spray Application)
Solvent:
78.0 parts by weight acetone
1.5 parts by weight dimethylformamide
Emulsifier: 0.5 parts by weight alkylarylpolyglcolether To produce a suitable preparation of the active compound, 1 part by weight of active compound is mixed with the stated amount of solvent and emulsifier, and the concentrate is dilutes with emulsifier-containing water to the desired concentration. Maize (*Zea mais*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means that all caterpillars have been killed and 0% means that none of the caterpillars have been killed.

In this test for example, the following compounds from the preparation examples showed good activity ≧80% at application rate of 500 g/ha:

| 1-221 | 1-231 | 1-254 | 1-271 | 1-295 | 1-308 | 1-328 | 3-7 | 7-25 |
|---|---|---|---|---|---|---|---|---|
| 1-222 | 1-235 | 1-255 | 1-272 | 1-296 | 1-314 | 1-329 | 3-9 | 7-4 |
| 1-224 | 1-236 | 1-256 | 1-274 | 1-298 | 1-315 | 1-330 | 7-19 | 7-7 |
| 1-225 | 1-238 | 1-258 | 1-276 | 1-299 | 1-316 | 1-331 | 7-2 | 7-8 |
| 1-226 | 1-239 | 1-260 | 1-277 | 1-301 | 1-321 | 3-10 | 7-20 | |
| 1-227 | 1-241 | 1-261 | 1-278 | 1-302 | 1-322 | 3-12 | 7-21 | |
| 1-228 | 1-242 | 1-262 | 1-293 | 1-303 | 1-325 | 3-13 | 7-22 | |
| 1-229 | 1-246 | 1-263 | 1-294 | 1-304 | 1-326 | 3-14 | 7-23 | |
| 1-230 | 1-250 | 1-270 | 1-294 | 1-307 | 1-327 | 3-15 | 7-24 | |

*Tetranychus Urticae*—Test; OP-Resistant (Spray Application)

Solvent:
78.0 parts by weight acetone
1.5 parts by weight dimethylformamide
Emulsifier: 0.5 parts by weight alkylarylpolyglcolether To produce a suitable preparation of active compound, 1 part by weight of active compound is mixed with the stated amount of solvent and emulsifier, and the concentrate is diluted with emulsifier-containing water to the desired concentration. French beans (*Phaseolus vulgaris*) which are heavily infested with all stages of the two spotted spidermite (*Tetranychus urticae*), are sprayed with a preparation of the active ingredient at the desired concentration.

After 6 days mortality in % is determined. 100% means that all spider mites have been killed and 0% means that none of the spider mites have been killed.

In this test for example, the following compounds from the preparation examples showed good activity ≧80% at application rate of 500 g/ha:

| 1-258 | 1-275 | 1-332 |
|---|---|---|
| 1-265 | 1-320 | 7-2 |

Unless not mentioned otherwise, the test solutions were prepared as follows:

Containing as solvent: Dimethylformamide, 3 parts by weight; and as emulsifier: Polyoxyethylene alkyl phenyl ether, 1 part by weight To prepare the test solution, 1 part by weight of an active compound is mixed with the above-mentioned amount of solvent containing the above-mentioned amount of emulsifier, and the mixture is diluted with water to the desired concentration.

Test Against Tobacco Cutworm (*Spodoptera Litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C. After 2 days and 4 days more sweet potato leaves were added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each treatment were averaged.

In the biological test example 1, the compounds Nos. 1-177, 1-190, 1-232, 1-234, 1-235, 1-236, 1-237, 1-238, 1-239, 1-240, 1-241, 1-242, 1-243, 1-244, 1-245, 1-246, 1-247, 1-248, 1-252, 1-253, 1-254, 1-257, 1-258, 1-259, 1-264, 1-265, 1-266, 1-267, 1-268, 1-269, 1-286, 1-288, 1-305, 1-310, 1-311, 1-312, 1-313, 1-314, 1-317, 1-318, 1-319, 1-324, 1-325, 1-326 and 5-2 showed an insecticidal activity of 100% at an active compound concentration of 100 ppm.

Test Against Cucurbit Leaf Beetle (*Aulacophora Femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and thus the insecticidal activity was calculated. An insecticidal activity of 100% means that all larvae were killed, whereas an insecticidal activity of 0% means that no larva was killed.

In the biological test example 2, the compounds Nos. 1-177, 1-190, 1-232, 1-233, 1-234, 1-235, 1-236,1-237, 1-238, 1-239, 1-240, 1-241, 1-242, 1-243, 1-244, 1-245, 1-246, 1-247, 1-248, 1-249, 1-251, 1-252, 1-253, 1-254, 1-256, 1-257, 1-258, 1-259, 1-260, 1-261, 1-264, 1-265, 1-266, 1-267, 1-268, 1-269, 1-270, 1-273, 1-286, 1-287, 1-288, 1-290, 1-291, 1-292, 1-305, 1-306, 1-309, 1-310, 1-311, 1-312, 1-314, 1-318, 1-319, 1-322, 1-324, 1-325, 1-326, 3-13, 3-16, 5-1, 5-2, 5-3, 5-5, 5-6 and 5-8 showed an insecticidal activity of 100% at an active compound concentration of 500 ppm.

The invention claimed is:
1. Compounds of the formula (I)

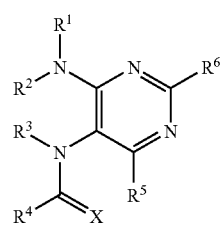

in which
$R^1$ represents a radical selected from the group consisting of $C_1$-$C_6$-alkyl, $C_2$-$C_6$-alkenyl, $C_2$-$C_6$-alkynyl, $C_1$-$C_6$-haloalkyl, cyano-$C_1$-$C_6$-alkyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_1$-$C_6$-haloalkylsulphanyl-$C_1$-$C_6$-alkyl, $C_1$-$C_6$-haloalkylsulphinyl-$C_1$-$C_6$-alkyl, $C_1$-$C_6$-haloalkylsulphonyl-$C_1$-$C_6$-alkyl, $C_3$-$C_8$cycloalkyl-$C_1$-

$C_6$-alkyl, halogenated $C_3$-$C_8$-cycloalkyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; heterocyclyl which is optionally mono- or polysubstituted by identical or different substituents selected from the group consisting of —OH, =O, —SH, =S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; and heterocyclyl-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano;

$R^2$ represents a radical selected from the group consisting of hydrogen, $C_1$-$C_6$-alkyl, $C_2$-$C_6$-alkenyl, $C_2$-$C_6$-alkynyl, $C_1$-$C_6$-haloalkyl, cyano-$C_1$-$C_6$-alkyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_1$-$C_6$-haloalkylsulphanyl-$C_1$-$C_6$-alkyl, $C_1$-$C_6$-haloalkylsulphinyl-$C_1$-$C_6$-alkyl, $C_1$-$C_6$-haloalkylsulphonyl-$C_1$-$C_6$-alkyl, $C_3$-$C_8$-cycloalkyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; heterocyclyl which is optionally mono- or polysubstituted by identical or different substituents selected from the group consisting of —OH, =O, —SH, =S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano; and heterocyclyl-$C_1$-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, mono-$C_1$-$C_6$-alkylamino, di-$C_1$-$C_6$-alkylamino, nitro and cyano;

$R^3$ represents a radical selected from the group consisting of hydrogen, $C_1$-$C_6$-alkyl, $C_2$-$C_6$-alkenyl, $C_2$-$C_6$-alkynyl, halo-$C_1$-$C_6$-alkyl, cyano-$C_1$-$C_6$-alkyl, $C_3$-$C_8$-cycloalkyl, halo-$C_3$-$C_8$-cycloalkyl, $C_3$-$C_8$-cycloalkenyl, halo-$C_3$-$C_8$-cycloalkenyl, $C_1$-$C_6$-alkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-alkylsulphanyl-$C_1$-$C_6$-alkyl, $C_1$-$C_6$-alkylsulphinyl-$C_1$-$C_6$-alkyl, $C_1$-$C_6$-alkylsulphonyl-$C_1$-$C_6$-alkyl, $C_3$-$C_8$-cycloalkyl-$C_1$-$C_6$-alkyl, phenyl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl which is optionally mono- or polysubstituted by identical or different substituents selected from the group consisting of —OH, =O, —SH, =S, —NH$_2$, halogen, C$_1$-C$_6$-alkyl, C$_1$-C$_6$-haloalkyl, C$_1$-C$_6$-alkoxy, C$_1$-C$_6$-alkylsulphanyl, C$_1$-C$_6$-alkylsulphinyl, C$_1$-C$_6$-alkylsulphonyl, mono-C$_1$-C$_6$-alkylamino, di-C$_1$-C$_6$-alkylamino, nitro and cyano; and heterocyclyl-C$_1$-C$_6$-alkyl which is optionally mono- or polysubstituted at the heterocycle by identical or different substituents selected from the group consisting of —OH, =O, —SH, =S, —NH$_2$, halogen, C$_1$-C$_6$-alkyl, C$_1$-C$_6$-haloalkyl, C$_1$-C$_6$-alkoxy, C$_1$-C$_6$-alkylsulphanyl, C$_1$-C$_6$-alkylsulphinyl, C$_1$-C$_6$-alkylsulphonyl, mono-C$_1$-C$_6$-alkylamino, di-C$_1$-C$_6$-alkylamino, nitro and cyano;

$R^4$ represents a radical selected from the group consisting of phenyl, 2-pyridyl, 3-pyridyl and pyrazolyl which are in each case optionally mono- or polysubstituted by identical or different radicals selected from the group consisting of halogen, C$_1$-C$_6$-alkyl, C$_1$-C$_6$-haloalkyl, C$_3$-C$_6$-cycloalkyl, C$_3$-C$_6$-halocycloalkyl, C$_3$-C$_6$-cycloalkyl-C$_1$-C$_6$-alkyl, C$_1$-C$_6$-alkoxy, C$_1$-C$_6$-haloalkoxy, C$_1$-C$_6$-alkoxy-C$_1$-C$_6$-alkyl, C$_1$-C$_6$-alkoxy-C$_1$-C$_6$-alkoxy, COOH, nitro, amino, cyano, C$_1$-C$_6$-alkylsulphanyl, C$_1$-C$_6$-alkylsulphinyl, C$_1$-C$_6$-alkylsulphonyl, C$_1$-C$_6$-haloalkylsulphanyl, C$_1$-C$_6$-haloalkylsulphinyl, C$_1$-C$_6$-haloalkylsulphonyl, mono-C$_1$-C$_6$-alkylamino, di-C$_1$-C$_6$-alkylamino, C$_1$-C$_6$-alkylaminocarbonyl, C$_3$-C$_6$-cycloalkylaminocarbonyl, phenyl (which for its part may be substituted by halogen), and hetaryl-C$_1$-C$_6$-alkyl (which for its part may be substituted by halogen, C$_1$-C$_6$-alkyl and C$_1$-C$_6$-haloalkyl);

$R^5$ represents a radical selected from the group consisting of hydrogen, halogen, cyano, C$_1$-C$_6$-alkyl, C$_1$-C$_6$-haloalkyl, C$_3$-C$_8$-cycloalkyl, C$_3$-C$_8$-halocycloalkyl, and also phenyl, 2-pyridyl or 3-pyridyl which are in each case optionally mono- or polysubstituted by identical or different radicals selected from the group consisting of halogen, amino, cyano, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_1$-C$_6$-alkoxy-C$_1$-C$_6$-alkyl, C$_1$-C$_6$-alkoxy-C$_1$-C$_6$-alkoxy, nitro, cyano, C$_1$-C$_6$-alkylcarbonyl, C$_1$-C$_6$-alkylcarbonylamino, C$_3$-C$_6$-cycloalkylcarbonylamino, C$_1$-C$_6$-alkylaminocarbonyl, C$_3$-C$_6$-cycloalkylaminocarbonyl C$_1$-C$_6$-alkoxycarbonyl, aminocarbonyl, C$_1$-C$_6$-alkoxyimino-C$_1$-C$_6$-alkyl, C$_1$-C$_6$-alkylsulphanyl, C$_1$-C$_6$-alkylsulphinyl, C$_1$-C$_6$-alkylsulphonyl, C$_1$-C$_6$-alkylsulphonyloxy, C$_1$-C$_6$-alkylsulphonylamino, C$_1$-C$_6$-haloalkylsulphanyl, C$_1$-C$_6$-haloalkylsulphinyl, C$_1$-C$_6$-haloalkylsulphonyl, tri-C$_1$-C$_6$-alkylsilyl, S(O)(=N—CN), S(O)(=N)R (in which R represents C$_1$-C$_6$-alkyl or C$_1$-C$_6$-haloalkyl), phenyl, phenyl-C$_1$-C$_6$-alkyl, phenyl-C$_1$-C$_6$-alkyloxy, phenyloxy, Pyrazolyl (where the phenyl groups or the pyrazolyl ring for their part may be substituted by halogen, C$_1$-C$_6$-alkyl, C$_3$-C$_8$-cycloalkyl, C$_1$-C$_6$-alkoxy, C$_1$-C$_6$-haloalkoxy, nitro, cyano, C$_1$-C$_6$-alkylsulphanyl, C$_1$-C$_6$-alkylsulphinyl, C$_1$-C$_6$-alkylsulphonyl, C$_1$-C$_6$-alkylsulphonyloxy, C$_1$-C$_6$-alkylsulphonylamino, C$_1$-C$_6$-haloalkylsulphanyl, C$_1$-C$_6$-haloalkylsulphinyl, C$_1$-C$_6$-haloalkylsulphonyl, S(O)(=N—CN), S(O)(=N)R (in which R represents C$_1$-C$_6$-alkyl or C$_1$-C$_6$-haloalkyl)), hetaryloxy-C$_1$-C$_6$-alkyl, hetaryloxy and hetaryl-C$_1$-C$_6$-alkyl, (where the hetaryl radical is in each case selected from the group consisting of pyrrolyl, imidazolyl, pyrazolyl, triazolyl, pyridyl, pyrimidinyl and tetrazolyl and may for its part be substituted by halogen, cyano, C$_1$-C$_6$-alkyl, C$_1$-C$_6$-haloalkyl, C$_3$-C$_8$-cycloalkyl, C$_3$-C$_8$-halocycloalkyl) and where two adjacent substituents together may also represent —OCH$_2$O—, —OCF$_2$O— or —OCH$_2$CH$_2$O—;

$R^6$ represents a radical selected from the group consisting of hydrogen, halogen, C$_1$-C$_6$-alkyl, C$_1$-C$_6$-haloalkyl, cyano-C$_1$-C$_6$-alkyl, C$_1$-C$_6$-alkoxy-C$_1$-C$_6$-alkyl, C$_1$-C$_6$-alkylcarbonyl, C$_1$-C$_6$-haloalkylcarbonyl, C$_3$-C$_8$-cycloalkyl, C$_3$-C$_8$-halocycloalkyl, C$_3$-C$_8$-cycloalkyl-C$_1$-C$_6$-alkyl, C$_1$-C$_6$-alkylsulphanyl, C$_1$-C$_6$-alkylsulphonyl, C$_2$-C$_6$-alkenyl, C$_2$-C$_6$-alkynyl, C$_1$-C$_6$-alkoxycarbonyl, C$_2$-C$_6$-alkenyloxycarbonyl, C$_2$-C$_6$-alkynyloxycarbonyl, C$_1$-C$_6$-alkoxycarbonyl-C$_1$-C$_6$-alkyl; phenyl, phenyl-C$_1$-C$_6$-alkyl which are in each case optionally mono- or polysubstituted at the phenyl ring by identical or different radicals selected from the group consisting of halogen, C$_1$-C$_6$-alkyl, C$_1$-C$_6$-haloalkyl, C$_1$-C$_6$-alkoxy, nitro and cyano; heterocyclyl-C$_1$-C$_6$-alkyl which is optionally mono- or polysubstituted at the heterocycle by identical or different substituents selected from the group consisting of halogen, C$_1$-C$_6$-alkyl, C$_1$-C$_6$-haloalkyl, C$_1$-C$_6$-alkoxy, nitro and cyano; heteroaryl-C$_1$-C$_6$-alkyl which is optionally mono- or polysubstituted at the heteroaromatic moiety by identical or different radicals selected from the group consisting of halogen, C$_1$-C$_6$-alkyl, C$_1$-C$_6$-haloalkyl, C$_1$-C$_6$-alkoxy, nitro and cyano; or phenylcarbonyl which is optionally mono- or polysubstituted at the phenyl ring by identical or different radicals selected from the group consisting of halogen, C$_1$-C$_6$-alkyl, C$_1$-C$_6$-haloalkyl, C$_1$-C$_6$-alkoxy, nitro and cyano, and X represents oxygen or sulphur.

2. The compound according to claim 1 in which $R^1$ represents a radical selected from the group consisting of C$_1$-C$_6$-alkyl, C$_2$-C$_6$-alkenyl, C$_2$-C$_6$-alkynyl, C$_1$-C$_6$-haloalkyl, C$_3$-C$_8$-cycloalkyl, C$_3$-C$_8$-halocycloalkyl, C$_3$-C$_8$-cycloalkenyl, C$_1$-C$_6$-alkoxy-C$_1$-C$_6$-alkyl, C$_1$-C$_6$-alkylsulphanyl-C$_1$-C$_6$-alkyl, C$_1$-C$_6$-alkylcarbonyl-C$_1$-C$_6$-alkyl, C$_1$-C$_6$-alkoxycarbonyl-C$_1$-C$_6$-alkyl, C$_3$-C$_6$-cycloalkyl-C$_1$-C$_6$-alkyl, halogenated C$_3$-C$_6$-cycloalkyl-C$_1$-C$_6$-alkyl, phenyl-C$_1$-C$_6$-alkyl which is optionally mono- or polysubstituted at the phenyl ring by identical or different substituents selected from the group consisting of halogen, C$_1$-C$_6$-alkyl, C$_1$-C$_6$-haloalkyl, C$_1$-C$_6$-alkoxy, nitro and cyano; heteroaryl which is optionally mono- or polysubstituted by identical or different substituents selected from the group consisting of —OH, —SH, —NH$_2$, halogen, C$_1$-C$_6$-alkyl, C$_1$-C$_6$-haloalkyl, C$_1$-C$_6$-alkoxy, C$_1$-C$_6$-alkylsulphanyl, C$_1$-C$_6$-alkylsulphinyl, C$_1$-C$_6$-alkylsulphonyl, mono-C$_1$-C$_6$-alkylamino, di-C$_1$-C$_6$-alkylamino, nitro and cyano; heteroaryl-C$_1$-C$_6$-alkyl which is optionally mono- or polysubstituted at the heteloaromatic moiety by identical or different substituents selected from the group consisting of —OH, —SH, —NH$_2$, halogen, C$_1$-C$_6$-alkyl, C$_1$-C$_6$-haloalkyl, C$_1$-C$_6$-alkoxy, C$_1$-C$_6$-alkylsulphanyl, C$_1$-C$_6$-alkylsulphinyl, C$_1$-C$_6$-alkylsulphonyl, mono-C$_1$-C$_6$-alkylamino, di-C$_1$-C$_6$-alkylamino, nitro and cyano; heterocyclyl-C$_1$-C$_6$-alkyl which is optionally mono- or polysubstituted at the heterocycle by identical or different substituents selected from the group consisting of —OH, =O, —SH, =S, —NH$_2$, halogen, C$_1$-C$_6$-alkyl, C$_1$-C$_6$-halo-alkyl, C$_1$-C$_6$-alkoxy, C$_1$-C$_6$-alkylsulphanyl, C$_1$-C$_6$-alkylsulphinyl, C$_1$-C$_6$-alkylsulphonyl, mono-C$_1$-C$_6$-alkylamino, di-C$_1$-C$_6$-alkylamino, nitro and cyano;

$R^2$ represents a radical selected from the group consisting of hydrogen, C$_1$-C$_6$-alkyl, C$_2$-C$_6$-alkenyl, C$_2$-C$_6$-alkynyl, C$_1$-C$_6$-haloalkyl, C$_3$-C$_8$-cycloalkyl, C$_3$-C$_8$-halocycloalkyl, C$_3$-C$_8$-cycloalkenyl, C$_1$-C$_6$-alkoxy-C$_1$-C$_6$-alkyl, C$_1$-C$_6$-alkylcarbonyl-C$_1$-C$_6$-alkyl, C$_1$-C$_6$- alkoxycarbonyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl-$C_1$-$C_6$-alkyl which is optionally mono- or polysubstituted at the heterocycle by identical or different substituents selected from the group consisting of —OH, =O, —SH, —NH$_2$, halogen, $C_1$-$C_6$-alkyl, $C_1$-$C_6$-halo-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano;

$R^3$ represents a radical selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylcarbonyl -$C_1$-$C_6$-alkyl, $C_1$-$C_6$-alkoxycarbonyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl-$C_1$-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-halo-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano;

$R^4$ represents 3-pyridyl or pyrazolyl which are in each case optionally mono- or polysubstituted by identical or different radicals selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkoyl-$C_1$-$C_6$-alkyl, $C_1$-$C_6$alkoxy, $C_1$-$C_6$-alkoxy, $C_1$-$C_6$-alkyl, $C_1$-$C_6$-alkoxy-$C_1$-$C_6$-alkoxy, COOH, nitro, amino, mono-$C_1$-$C_6$-alkylamino, di-$C_1$-$C_6$-alkylamino, $C_1$-$C_6$-alkylaminocarbonyl and $C_3$-$C_6$-cycloalkylaminocarbonyl; or $R^4$ represents pyrazolyl which is optionally substituted by halogen or $C_1$-$C_6$-alkyl, phenyl (which for its part may be substituted by halogen) or by pyrazolylmethyl (which for its part may be substituted by $C_1$-$C_6$-haloalkyl);

$R^5$ represents phenyl, 2-pyridyl or 3-pyridyl which are in each case optionally mono- or polysubstituted by identical or different radicals selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxy-$C_1$-$C_6$-alkoxy, nitro, amino, cyano, mono-$C_1$-$C_6$-alkylamino, di-$C_1$-$C_6$-alkylamino, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, hetaryloxy-$C_1$-$C_6$-alkyl, hetaryloxy and hetaryl-$C_1$-$C_6$-alkyl, where the hetaryl radical is selected from the group consisting of pyrrolyl, imidazolyl, pyrazolyl, triazolyl, pyridyl, pyrimidinyl and tetrazolyl and for its part may be substituted by substituents selected from the group consisting of halogen, cyano, $C_1$-$C_6$-alkyl, $C_1$-$C_6$-haloalkyl, $C_3$-$C_8$-cycloalkyl and $C_3$-$C_8$-halocycloalkyl; or $R^5$ represents hydrogen, halogen, $C_1$-$C_4$-alkyl or $C_3$-$C_6$-cycloalkyl, $R^6$ represents a radical selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_1$-$C_6$-alkylcarbonyl, $C_1$-$C_6$-haloalkylcarbonyl, $C_3$-$C_6$-cycloalkyl, $C_3$-$C_6$-cycloalkyl-$C_1$-$C_6$-alkyl, $C_1$-$C_6$-alkylsulphanyl, $C_2$-$C_6$-alkenyl, $C_2$-$C_6$-alkynyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkoxycarbonyl-$C_1$-$C_6$-alkyl, phenyl, phenyl-$C_1$-$C_6$-alkyl which are in each case optionally mono- or polysubstituted at the phenyl ring by identical or different radicals selected from the group consisting of halogen, $C_1$-$C_6$-alkyl, $C_1$-$C_6$-haloalkyl, $C_1$-$C_6$-alkoxy, nitro and cyano; heterocyclyl-$C_1$-$C_6$-alkyl which may optionally be mono- or polysubstituted at the heterocycle by identical or different substituents selected from the group consisting of halogen, $C_1$-$C_6$-alkyl, $C_1$-$C_6$-haloalkyl, $C_1$-$C_6$-alkoxy, nitro and cyano; and phenylcarbonyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; and X represents oxygen or sulphur.

3. A compound according to claim 1 in which $R^1$ represents a radical selected from the group consisting of $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylsulphanyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_3$-$C_6$-cycloalkyl-$C_1$-$C_6$-alkyl, halogenated $C_3$-$C_6$-cycloalkyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$- alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl-$C_1$-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-halo- alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano;

$R^2$ represents a radical selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl-$C_1$-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-halo-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano;

$R^3$ represents a radical selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $C_3$-$C_8$-halocycloalkyl, $C_3$-$C_8$-cycloalkenyl, $C_1$-$C_6$-alkoxy-$C_1$-$C_6$-alkyl, $C_1$-$C_6$-alkylcarbonyl- $C_1$-$C_6$-alkyl, $C_1$-$C_6$-alkoxycarbonyl-$C_1$-$C_6$-alkyl, phenyl-$C_1$-$C_6$-alkyl which is optionally mono- or polysubstituted at the phenyl ring by identical or different substituents selected from the group consisting of halogen, $C_1$-$C_6$-alkyl, $C_1$-$C_6$-haloalkyl, $C_1$-$C_6$-alkoxy, nitro and cyano; heteroaryl which is optionally mono- or polysubstituted by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heteroaryl-$C_1$-$C_6$-alkyl which is optionally mono- or polysubstituted at the heteroaromatic moiety by identical or different substituents selected from the group consisting of —OH, —SH, —NH$_2$, halogen, $C_1$-$C_6$-alkyl, $C_1$-$C_6$-haloalkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano; heterocyclyl-$C_1$-$C_6$-alkyl which is optionally mono- or polysubstituted at the heterocycle by identical or different substituents selected from the group consisting of —OH, =O, —SH, =S, —NH$_2$, halogen, $C_1$-$C_6$-alkyl, $C_1$-$C_6$-halo-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano;

$R^4$ represents 3-pyridyl or pyrazolyl which are in each case optionally mono- or polysubstituted by identical or different radicals selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, COOH, nitro, amino, mono-$C_1$-$C_6$-alkylamino, di-$C_1$-$C_6$-alkylamino, $C_1$-$C_6$-alkylaminocarbonyl and $C_3$-$C_6$-cycloalkylaminocarbonyl; or $R^4$ represents pyrazolyl which is optionally substituted by halogen or $C_1$-$C_6$-alkyl, phenyl (which for its part may be substituted by halogen) or by pyrazolylmethyl (which for its part may be substituted by $C_1$-$C_6$-haloalkyl);

$R^5$ represents phenyl, 2-pyridyl or 3-pyridyl which are in each case optionally mono- or polysubstituted by identical or different radicals selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxy-$C_1$-$C_6$-alkoxy, nitro, amino, cyano, mono-$C_1$-$C_6$-alkylamino, di-$C_1$-$C_6$-alkylamino, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, hetaryloxy- $C_1$-$C_6$-alkyl, hetaryloxy and hetaryl-$C_1$-$C_6$-alkyl, where the hetaryl radical is selected from the group consisting of pyrrolyl, imidazolyl, pyrazolyl, triazolyl, pyridyl, pyrimidinyl and tetrazolyl and for its part may be substituted by substituents selected from the group consisting of halogen, cyano, $C_1$-$C_6$-alkyl, $C_1$-$C_6$-haloalkyl, $C_3$-$C_8$-cycloalkyl and $C_3$-$C_8$-halocycloalkyl; or $R^5$ represents hydrogen, halogen, $C_1$-$C_4$-alkyl or $C_3$-$C_6$-cycloalkyl, $R^6$ represents a radical selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_1$-$C_6$-alkylcarbonyl, $C_1$-$C_6$-haloalkylcarbonyl, $C_3$-$C_6$-cycloalkyl, $C_3$-$C_6$-cycloalkyl-$C_1$-$C_6$-alkyl, $C_1$-$C_6$-alkylsulphanyl, $C_2$-$C_6$-alkenyl, $C_2$-$C_6$-alkynyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkoxycarbonyl-$C_1$-$C_6$-alkyl, phenyl, phenyl-$C_1$-$C_6$-alkyl which are in each case optionally mono- or polysubstituted at the phenyl ring by identical or different radicals selected from the group consisting of halogen, $C_1$-$C_6$-alkyl, $C_1$-$C_6$-haloalkyl, $C_1$-$C_6$-alkoxy, nitro and cyano; heterocyclyl-$C_1$-$C_6$-alkyl which may optionally be mono- or polysubstituted at the heterocycle by identical or different substituents selected from the group consisting of halogen, $C_1$-$C_6$-alkyl, $C_1$-$C_6$-haloalkyl, $C_1$-$C_6$-alkoxy, nitro and cyano; and phenylcarbonyl which is optionally mono- or polysubstituted at the phenyl ring by identical or different substituents selected from the group consisting of halogen, $C_1$-$C_6$-haloalkyl, $C_1$-$C_6$-alkoxy, nitro and cyano; and X represents oxygen or sulphur.

4. The compound according to claim 1 in which $R^1$ represents a radical selected from the group consisting of $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-alkylsulphanyl-$C_1$-$C_6$-alkyl, $C_1$-$C_6$-alkoxycarbonyl-$C_1$-$C_6$-alkyl, $C_3$-$C_6$-cycloalkyl-$C_1$-$C_6$-alkyl and halogenated $C_3$-$C_6$-cycloalkyl-$C_1$-$C_6$-alkyl, $R^2$ represents hydrogen, $R^3$ represents hydrogen, $R^4$ represents 3-pyridyl which is mono- or polysubstituted by radicals selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy, $C_1$-$C_6$-alkylaminocarbonyl and $C_3$-$C_6$-cycloalkylaminocarbonyl, or $R^4$ represents pyrazolyl which may be substituted by halogen, $C_1$-$C_6$-alkyl, phenyl (which for its part may be substituted by halogen) or by pyrazolylmethyl (which for its part may be substituted by $C_1$-$C_6$-haloalkyl), $R^5$ represents a radical selected from the group consisting of phenyl, 2-pyridyl and 3-pyridyl, each of which is mono- or polysubstituted by at least one radical selected from the group consisting of halogen, $C_1$-$C_6$-alkyl, $C_1$-$C_6$-haloalkyl, $C_1$-$C_6$-alkoxy, $C_1$-$C_6$-haloalkoxy, nito, cyano, $C_1$-$C_6$-alkylsulphanyl, $C_1$-$C_6$-alkylsulphinyl, $C_1$-$C_6$-alkylsulphonyl, $C_1$-$C_6$-haloalkylsulphanyl, $C_1$-$C_6$-haloalkylsulphinyl, $C_1$-$C_6$-haloalkylsulphonyl, hetaryloxy-$C_1$-$C_6$-alkyl, hetaryloxy and hetaryl-$C_1$-$C_6$-alkyl, where the hetaryl radical is selected from the group consisting of pyrrolyl, imidazolyl, pyrazolyl, triazolyl, pyridyl, pyrimidinyl and tetrazolyl and may for its turn be substituted by substituents selected from the group consisting of halogen, cyano, $C_1$-$C_6$alkyl, $C_1$-$C_6$-haloalkyl, $C_3$-$C_8$-cycloalkyl and $C_3$-$C_8$-halocycloalkyl, or $R^5$ represents a radical selected from the group consisting of hydrogen, halogen, $C_1$-$C_4$-alkyl and $C_3$-$C_6$-cycloalkyl, $R^6$ represents a radical selected from the group consisting of hydrogen, halogen, $C_1$-$C_6$-alkyl, $C_1$-$C_6$-haloalkyl, $C_3$-$C_6$-cycloalkyl, $C_1$-$C_6$-alkylsulphanyl and phenyl which may be substituted by halogen, and X represents oxygen.

5. The compound according to claim 1 in which $R^1$ represents a radical selected from the group consisting of $CH_3$, $CH_2CH_3$, $CH(CH_3)_2$, cyclopropyl, halocyclopropyl, $C(CH_3)_3$, $CH(CH_3)CH_2SCH_3$, $CH_2CH_2CH_3$, $CH(CH_3)CH_2CH_3$, $CH_2CF_3$, $CHCH_3CF_3$, and $CH(CH_3)$cyclopropyl, $R^2$ represents hydrogen, $R^3$ represents hydrogen, $R^4$ represents 3-pyridyl which is substituted in the 2-position by a substituent selected from the group consisting of F, Cl, Br, methyl, ethyl, $CF_3$, $CH_2CF_3$, $CHFCH_3$, $CHFCF_3$, cyclopropyl and cyclopropylmethyl, or $R^4$ represents pyrazolyl which may be substituted by F, Cl, methyl, ethyl or by pyrazolylmethyl which for its part may be substituted by $C_1$-$C_6$-haloalkyl, $R^5$ represents phenyl which is mono- or polysubstituted by a radical selected from the group consisting of $CH_3$, F, Cl, $CF_3$, $CF(CF_3)_2$, $OCH_3$, $OCF_3$, $NO_2$, CN, $SCF_3$, $S(O)CF_3$ and $S(O)_2CF_3$ and $CH_2$-Q, wherein Q represents a radical selected from the group consisting of

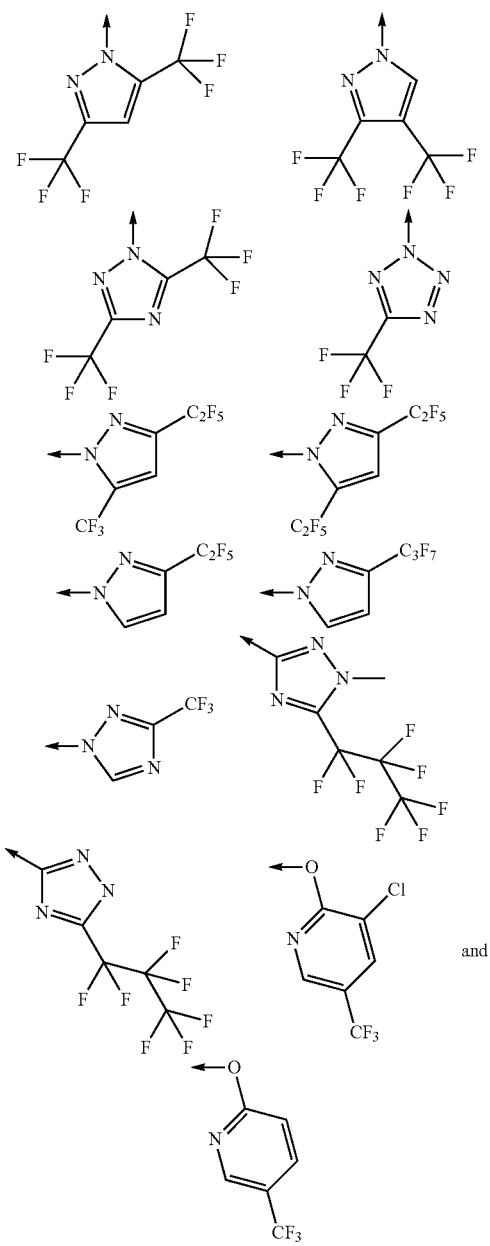

where the arrow indicates the point of attachment to the $CH_2$ group, $R^6$ represents hydrogen, and X represents oxygen.

6. A composition, characterized in that it comprises at least one compound of the formula (I) according to claim 1 and customary extenders and/or surfactants.

7. A method for controlling pests, characterized in that a compound of the formula (I) according to claim 1 or a composition according to claim 6 is allowed to act on the pests and/or their habitat.

8. The method according to claim 7, wherein said pests are insects, arachnids, helminths, nematodes or molluscs.

9. A pharmaceutical compositions comprising at least one compound according to claim 1.

* * * * *